(12) United States Patent
Yoshikawa et al.

(10) Patent No.: US 9,357,971 B2
(45) Date of Patent: Jun. 7, 2016

(54) X-RAY CT PHOTOGRAPHIC APPARATUS

(71) Applicant: J. Morita Manufacturing Corporation, Kyoto-shi, Kyoto (JP)

(72) Inventors: Hideki Yoshikawa, Kyoto (JP); Masakazu Suzuki, Kyoto (JP)

(73) Assignee: J. MORITA MANUFACTURING CORPORATION, Kyoto (JP)

(*) Notice: Subject to any disclaimer, the term of this patent is extended or adjusted under 35 U.S.C. 154(b) by 267 days.

(21) Appl. No.: 13/874,598

(22) Filed: May 1, 2013

(65) Prior Publication Data

US 2013/0294569 A1 Nov. 7, 2013

(30) Foreign Application Priority Data

May 2, 2012 (JP) .................. 2012-105318
Apr. 26, 2013 (JP) .................. 2013-094091

(51) Int. Cl.
A61B 6/03 (2006.01)
A61B 6/06 (2006.01)
A61B 6/00 (2006.01)
A61B 6/14 (2006.01)

(52) U.S. Cl.
CPC .............. *A61B 6/035* (2013.01); *A61B 6/032* (2013.01); *A61B 6/06* (2013.01); *A61B 6/14* (2013.01); *A61B 6/405* (2013.01); *A61B 6/4085* (2013.01); *A61B 6/469* (2013.01); *A61B 6/501* (2013.01)

(58) Field of Classification Search
CPC .......... A61B 6/032; A61B 6/035; A61B 6/06; A61B 6/14; A61B 6/405; A61B 6/4085; A61B 6/469; A61B 6/501

USPC ....................................... 378/38–40
See application file for complete search history.

(56) References Cited

U.S. PATENT DOCUMENTS

| | | | |
|---|---|---|---|
| 5,530,935 A * | 6/1996 | Dillen | 378/98.2 |
| 6,140,649 A * | 10/2000 | Lonn | 250/363.04 |
| 6,173,033 B1 * | 1/2001 | Klingenbeck-Regn et al. | 378/20 |
| 6,215,848 B1 * | 4/2001 | Linders et al. | 378/98.12 |
| 6,249,003 B1 * | 6/2001 | Culp | 250/363.04 |
| 6,292,534 B1 * | 9/2001 | Linders et al. | 378/98.2 |
| 6,339,636 B1 * | 1/2002 | Ogawa | 378/146 |
| 6,496,558 B2 * | 12/2002 | Graumann | 378/39 |
| 6,501,828 B1 | 12/2002 | Popescu | |

(Continued)

FOREIGN PATENT DOCUMENTS

| JP | H11-19078 A | 1/1999 |
|---|---|---|
| JP | 2003-245277 A | 9/2003 |

(Continued)

*Primary Examiner* — Allen C. Ho
(74) *Attorney, Agent, or Firm* — DLA PIPER LLP (US)

(57) ABSTRACT

An X-ray CT photographic apparatus including: a beam shaping mechanism that regulates an irradiation range of an X-ray generated from an X-ray generator and shapes the X-ray into an X-ray cone beam; and a main body controller that changes a read region, where an X-ray detection signal is read in the X-ray detector, according to the irradiation range of the X-ray cone beam. The main body controller changes the irradiation range of the X-ray cone beam to an x-axis direction during an X-ray CT photography such that only a set CT photographic region is irradiated with the X-ray cone beam according to the set CT photographic region input through a CT photographic region setting unit. The main body controller changes a read region in an X-ray detector with respect to the x-axis direction in a detection surface of the X-ray detector during the X-ray CT photography.

19 Claims, 31 Drawing Sheets

(56) References Cited

U.S. PATENT DOCUMENTS

| | | | |
|---|---|---|---|
| 6,674,837 B1 * | 1/2004 | Taskar et al. | 378/122 |
| 6,898,269 B2 * | 5/2005 | Halsmer et al. | 378/146 |
| 8,005,187 B2 * | 8/2011 | Suzuki et al. | 378/39 |
| 8,340,246 B2 * | 12/2012 | Kang et al. | 378/62 |
| 8,401,267 B2 * | 3/2013 | Nakai et al. | 382/132 |
| 8,538,110 B2 * | 9/2013 | Nakai et al. | 382/131 |
| 8,588,364 B2 * | 11/2013 | Suzuki et al. | 378/40 |
| 8,817,944 B2 * | 8/2014 | Arai et al. | 378/11 |
| 2004/0120457 A1 * | 6/2004 | Karellas et al. | 378/62 |
| 2009/0168966 A1 | 7/2009 | Suzuki et al. | |
| 2011/0013742 A1 | 1/2011 | Zaiki et al. | |
| 2011/0019798 A1 | 1/2011 | Kang et al. | |

FOREIGN PATENT DOCUMENTS

| | | |
|---|---|---|
| JP | 2008-114056 A | 5/2008 |
| JP | 2010-42121 A | 2/2010 |
| JP | 4516626 B | 8/2010 |
| JP | 2011-25012 A | 2/2011 |
| WO | WO 2007/046372 A | 4/2007 |
| WO | WO 2009/063974 A | 5/2009 |
| WO | WO 2009/141766 A | 11/2009 |

\* cited by examiner

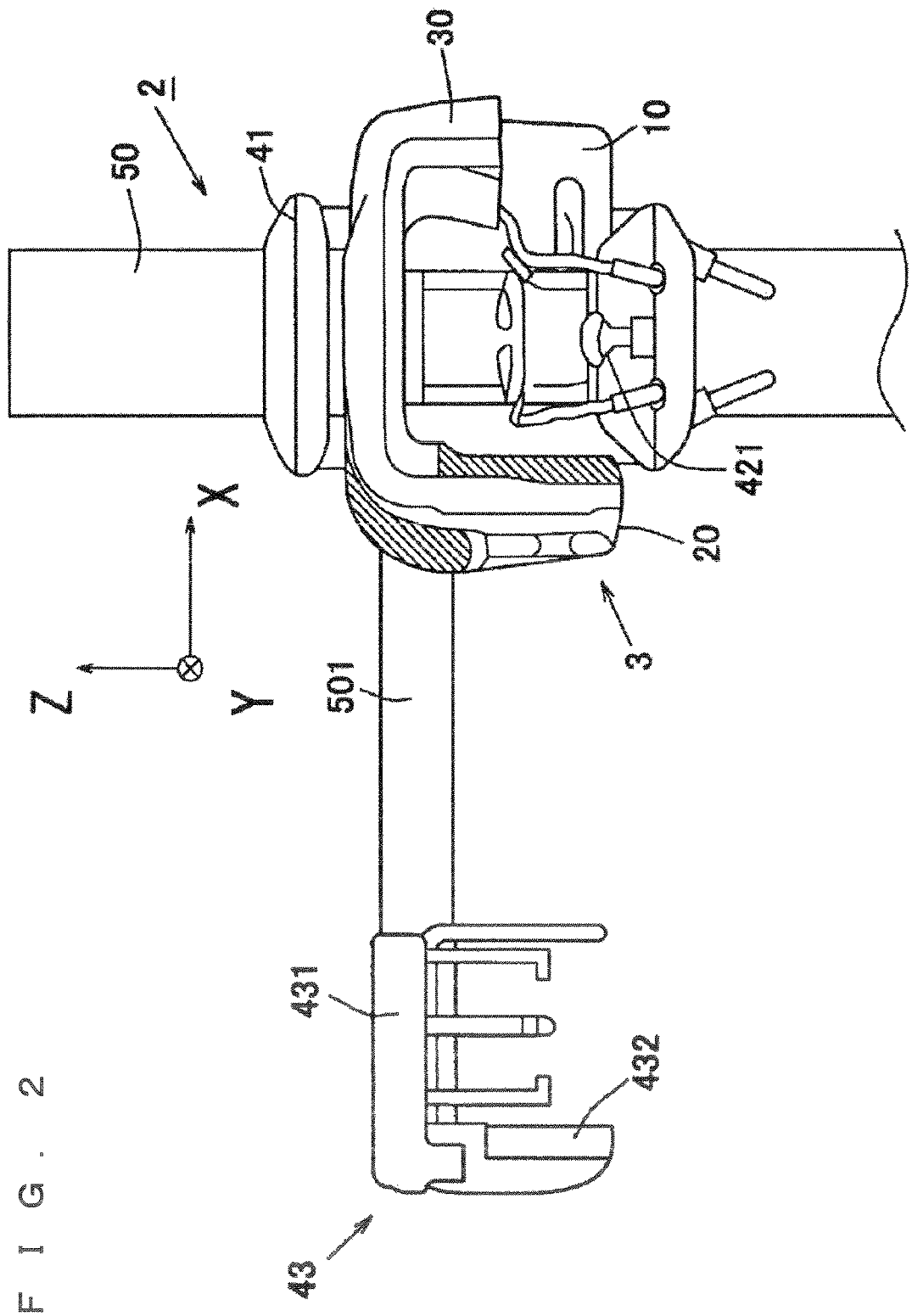

F I G . 9
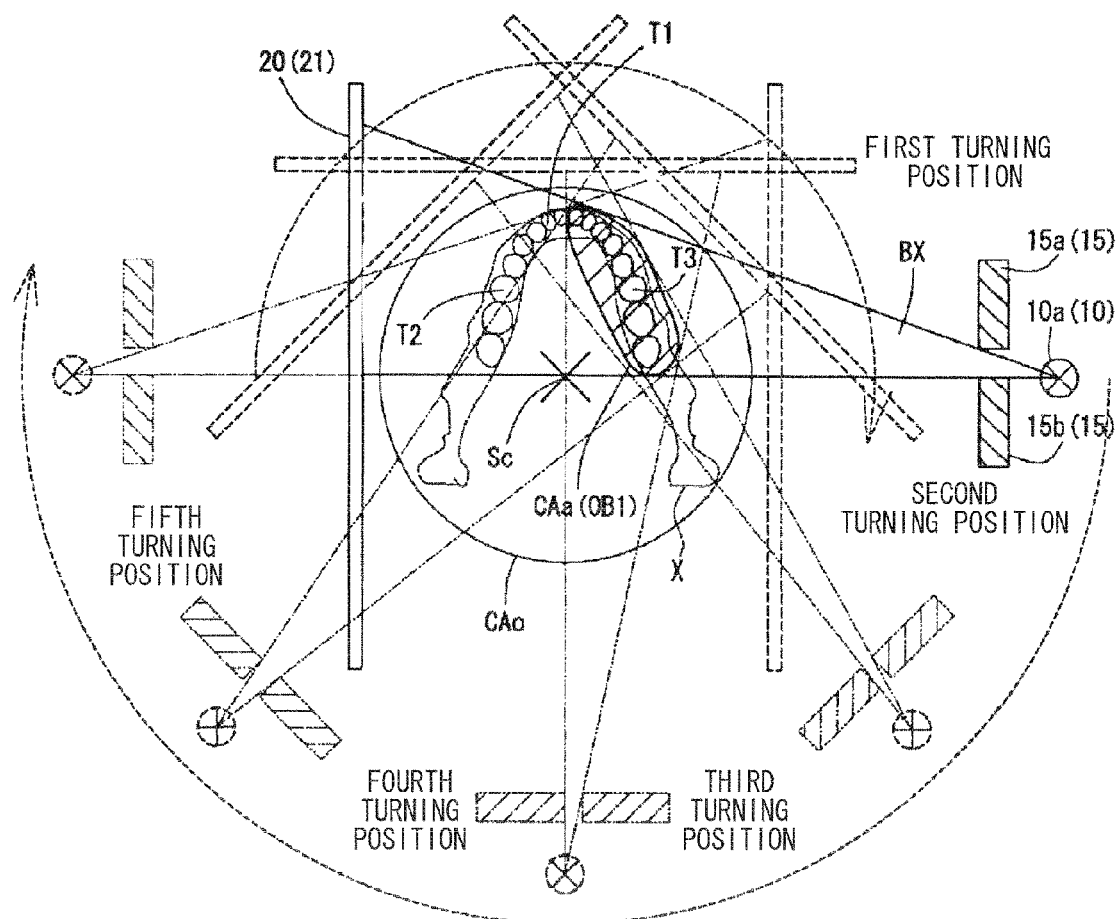

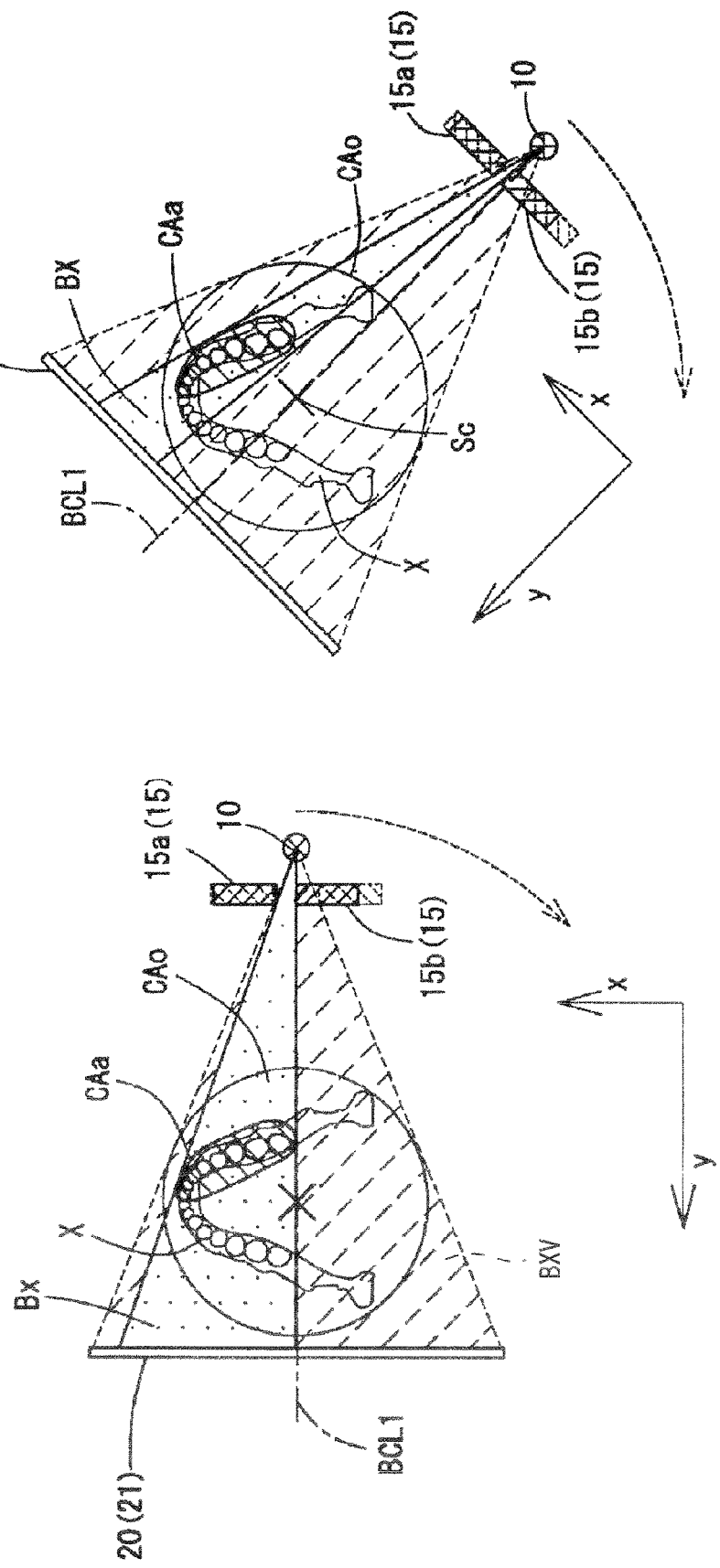

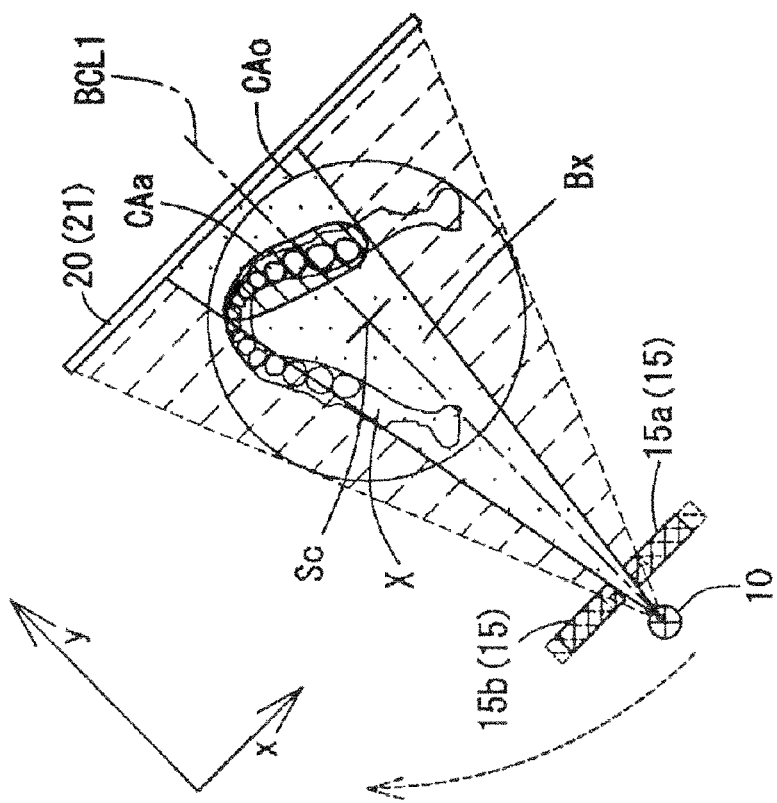
FIG. 11A THIRD TURNING POSITION
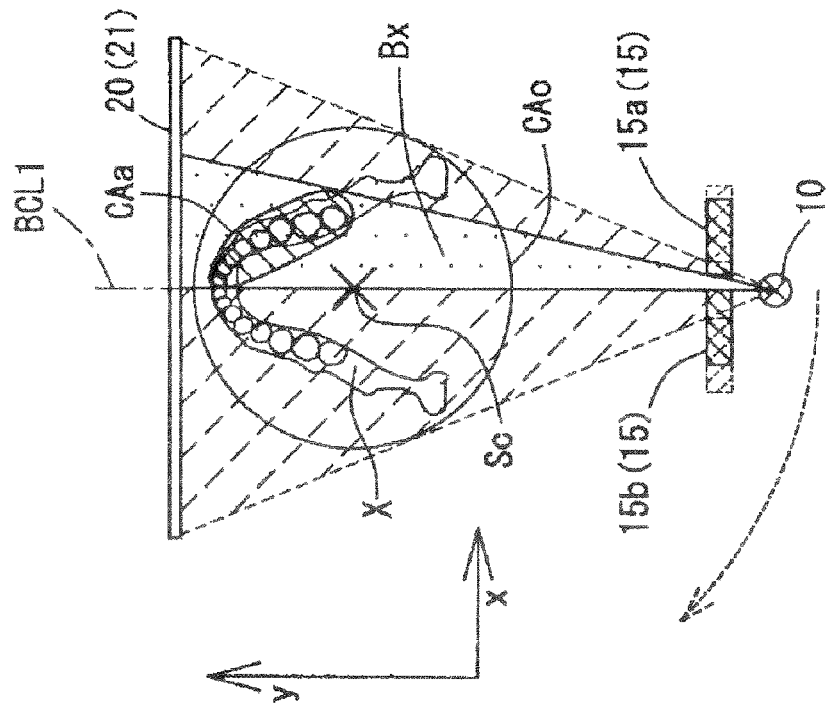
FIG. 11B FOURTH TURNING POSITION

FIFTH TURNING POSITION

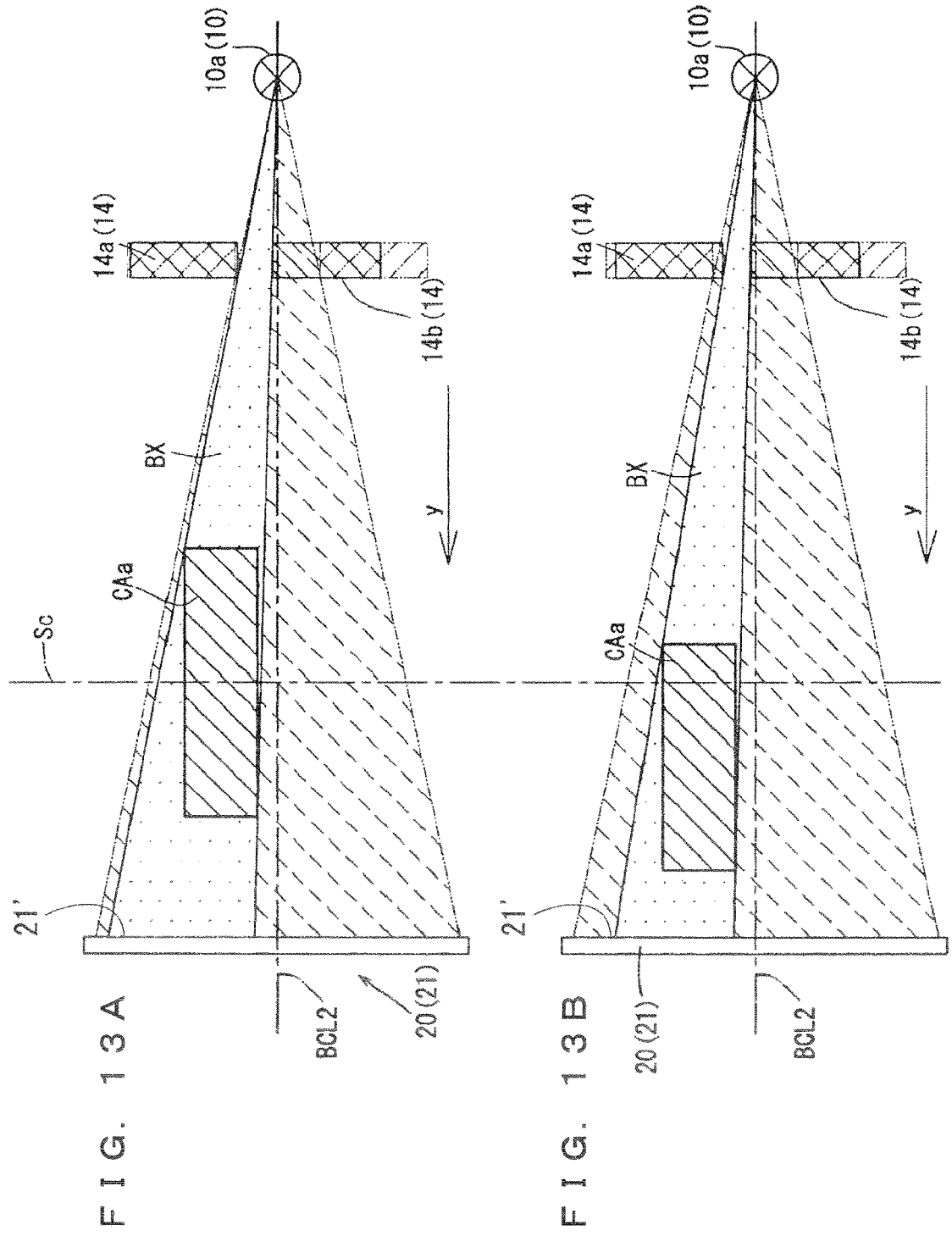

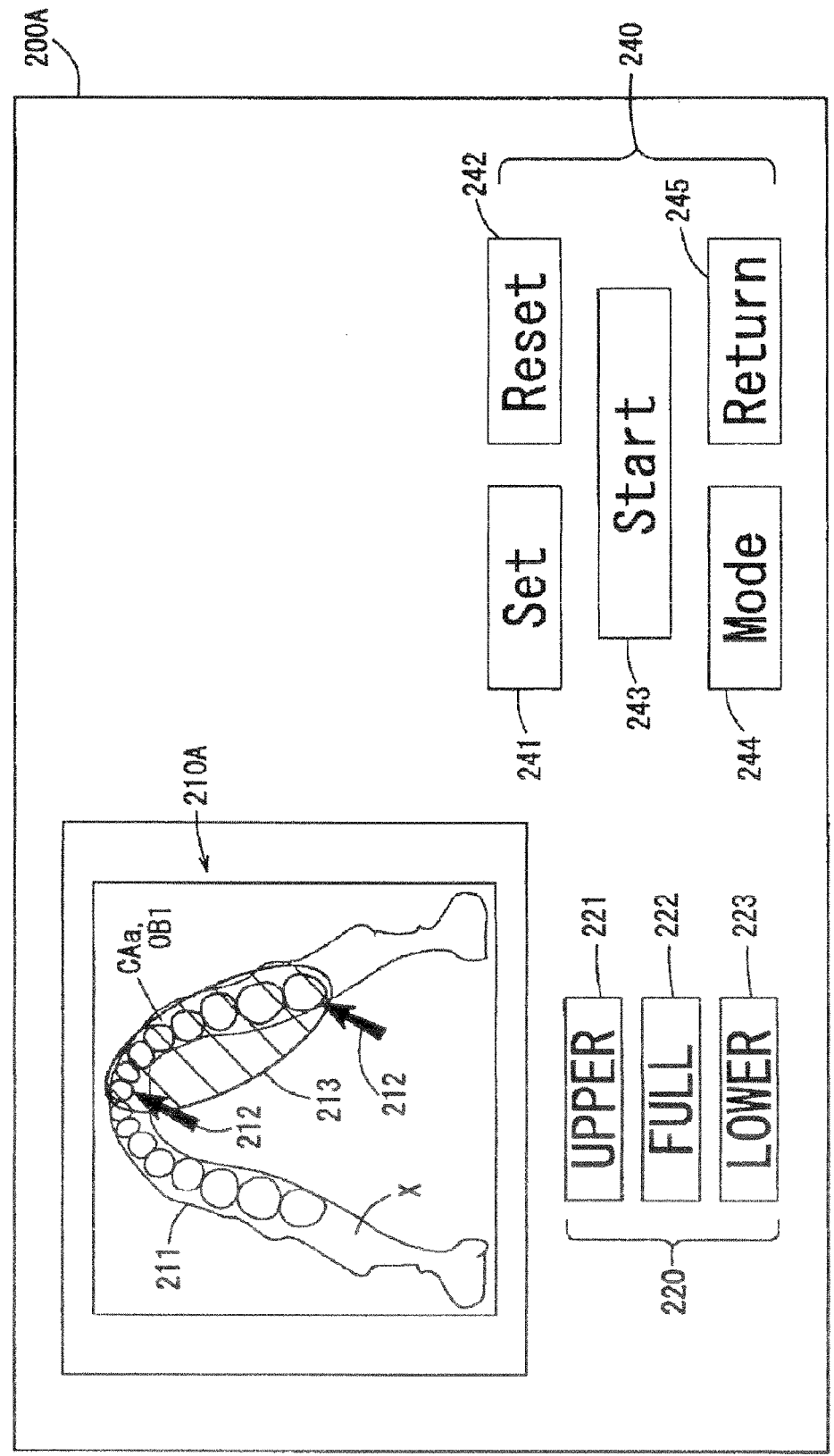

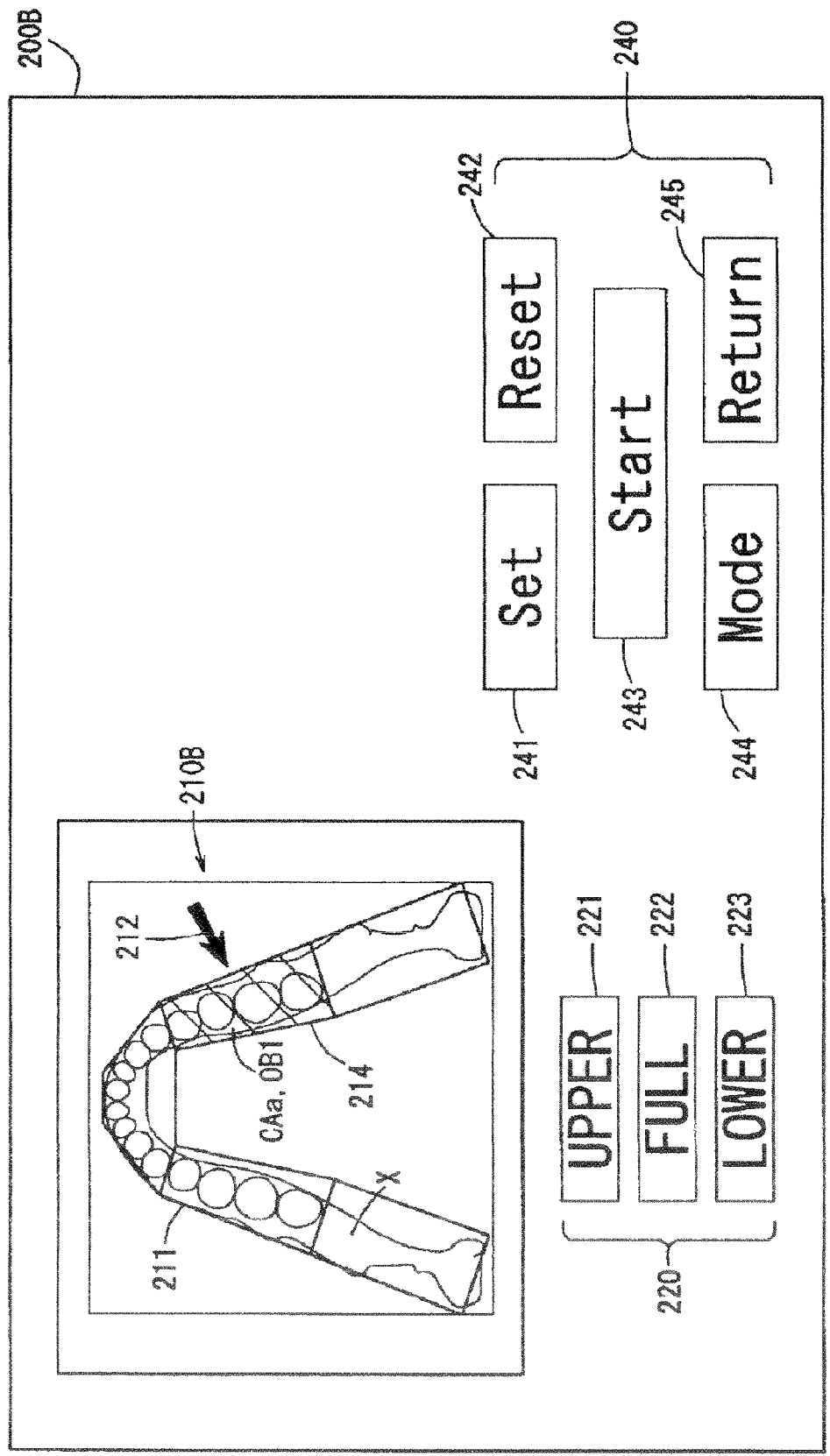

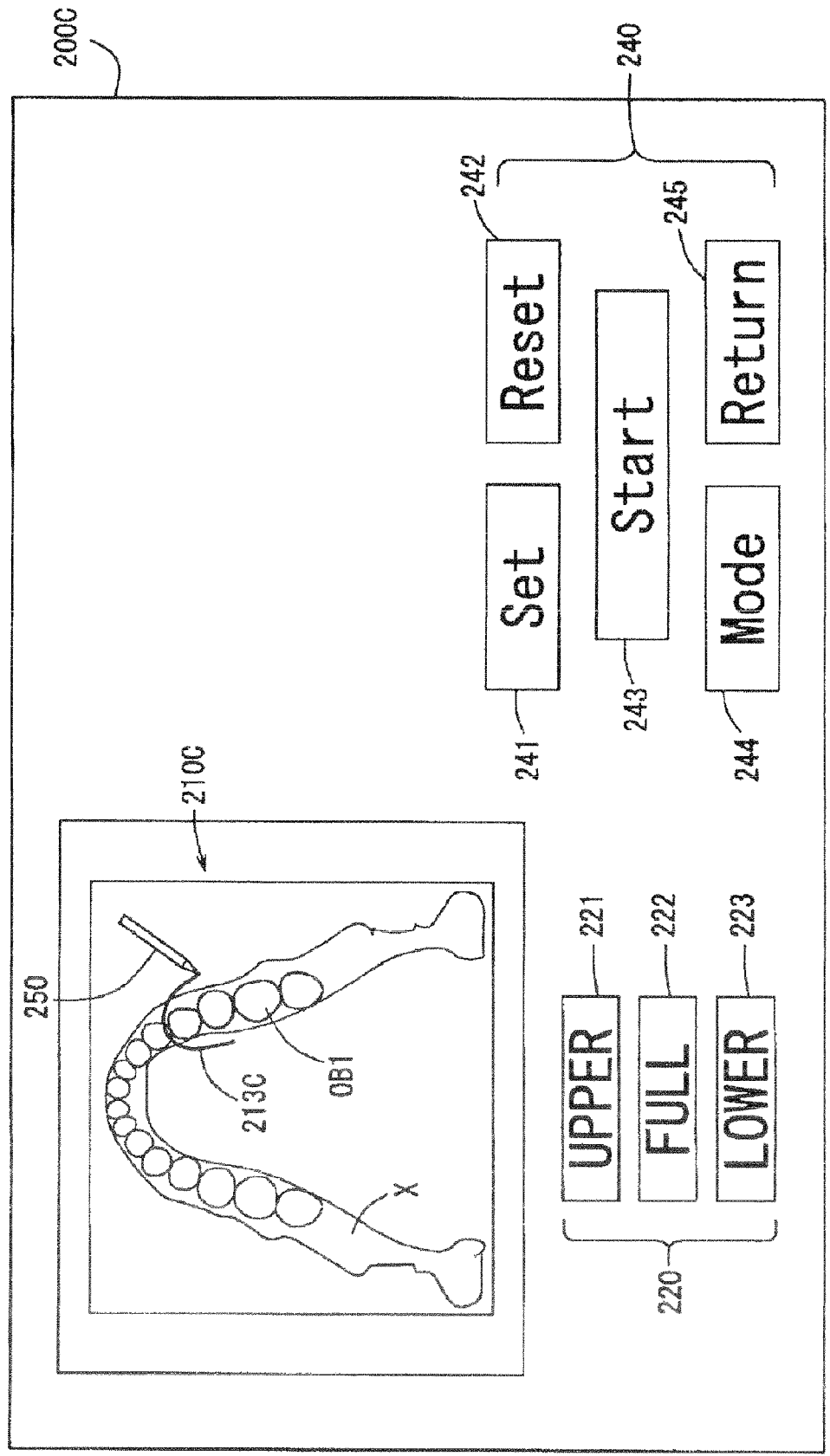

F I G . 1 8
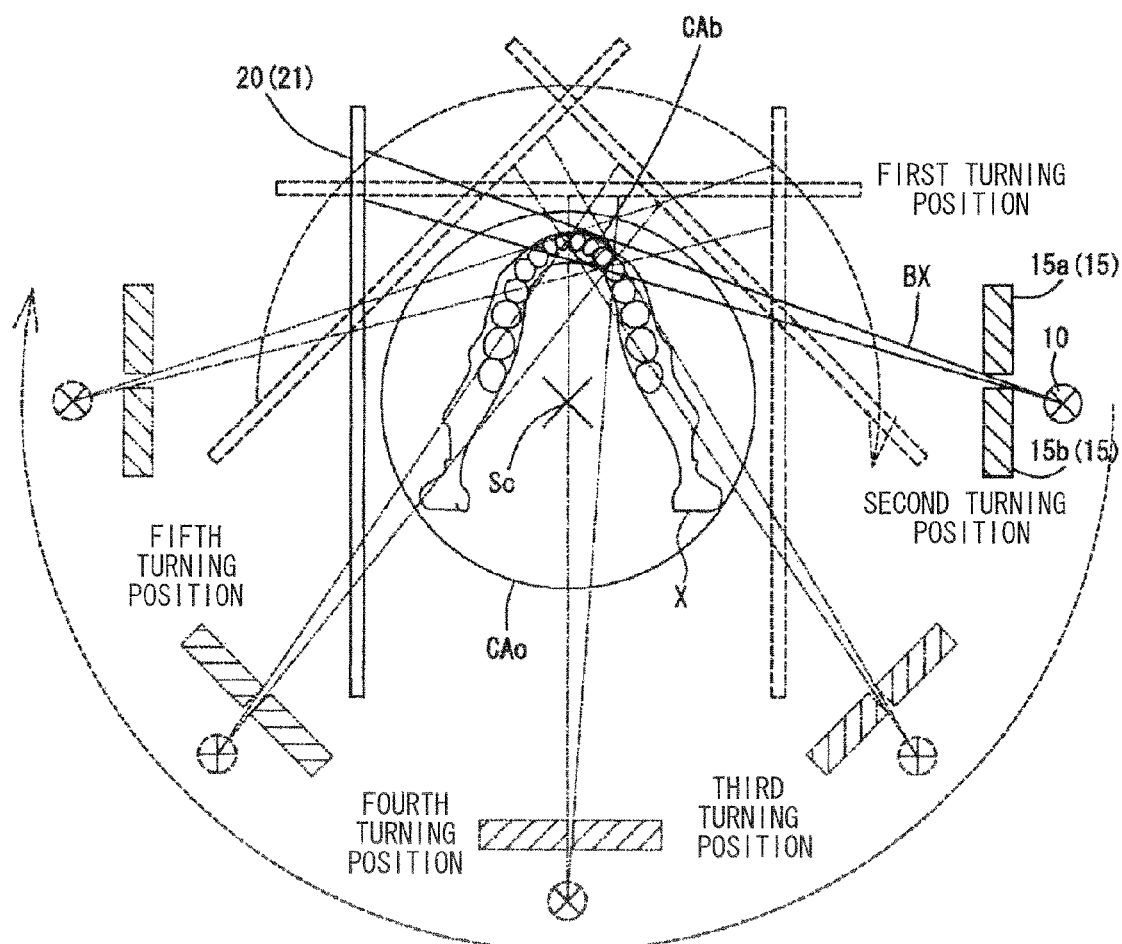

FIG. 19A
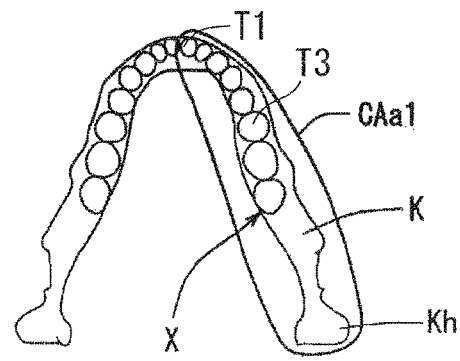
FIG. 19B
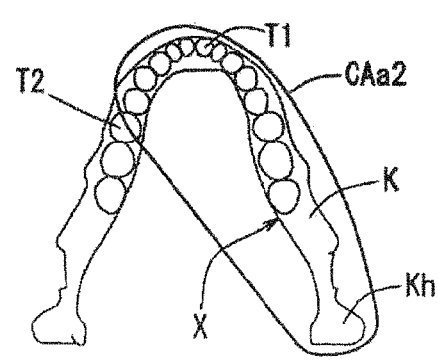
FIG. 19C
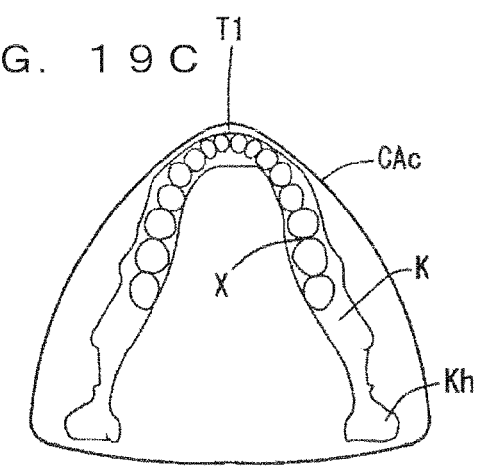
FIG. 19D
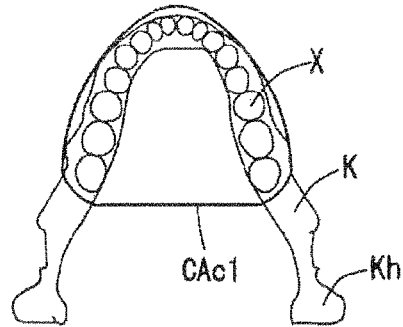
FIG. 19E
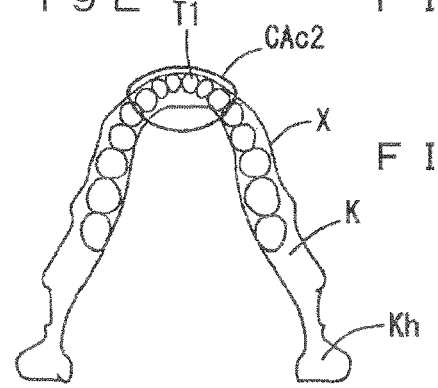
FIG. 19F
FIG. 19G
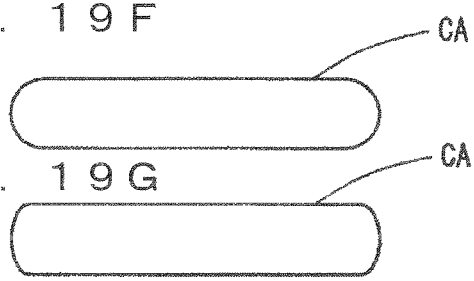

F I G . 2 2
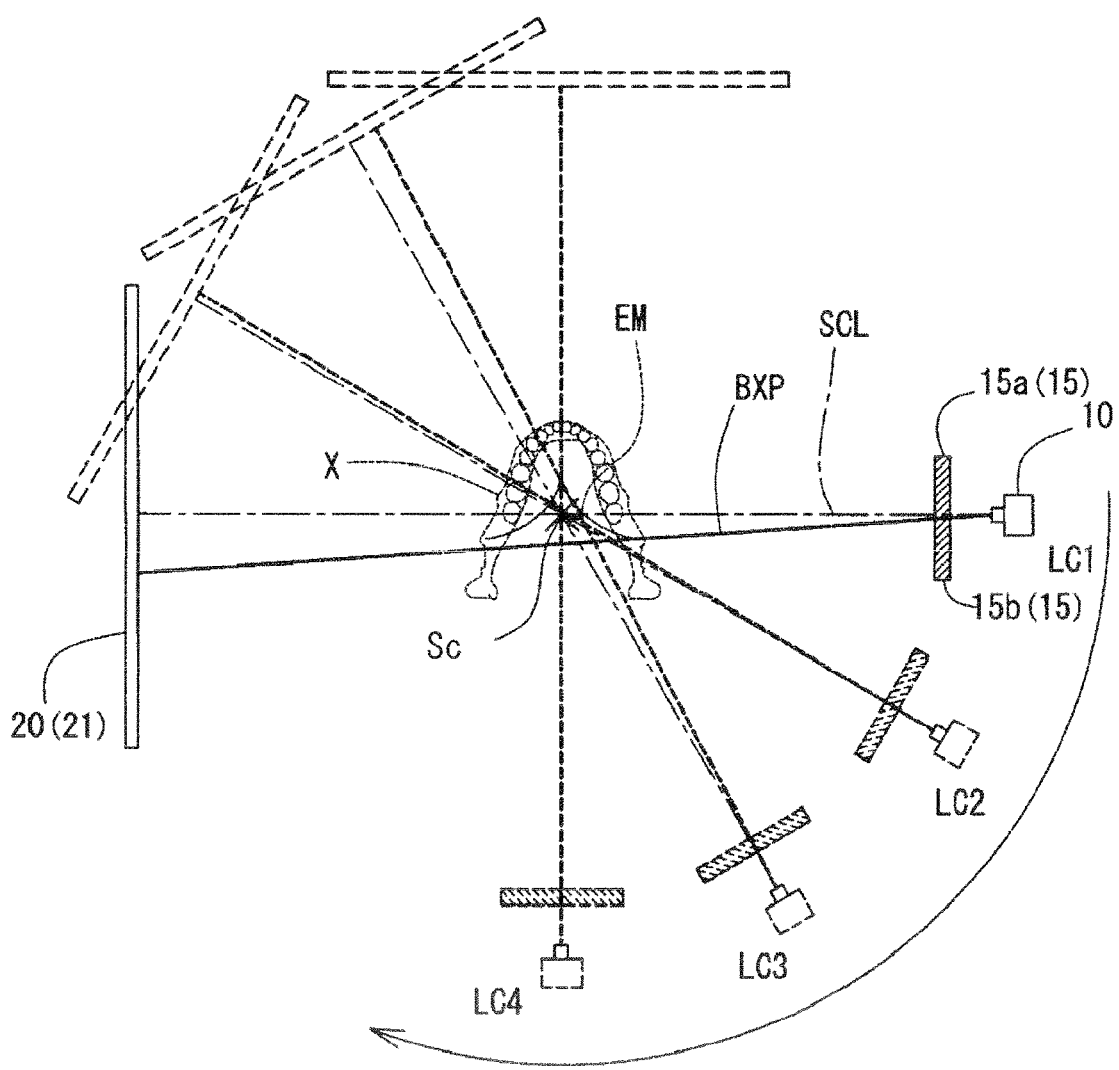

F I G. 2 4
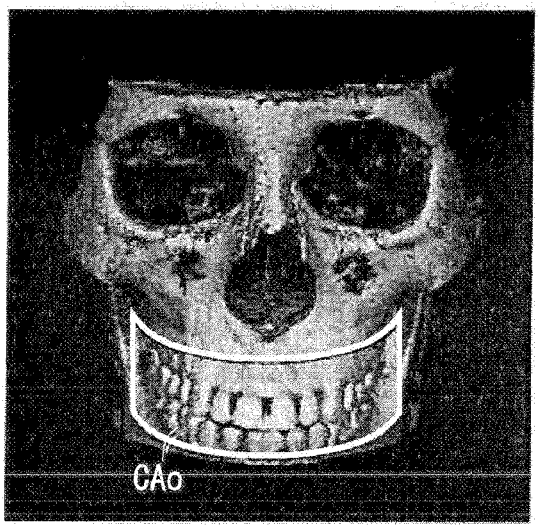
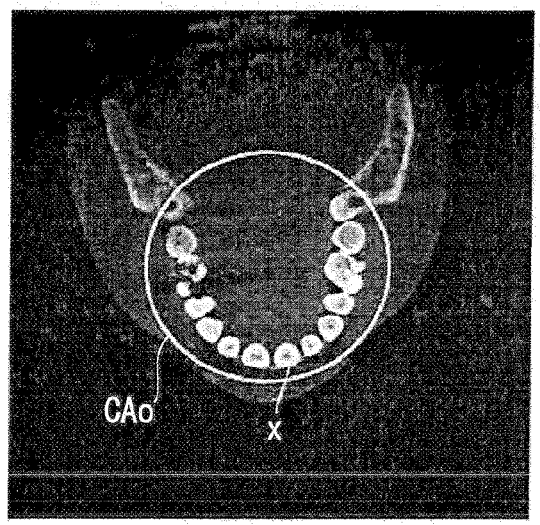

F I G . 2 5
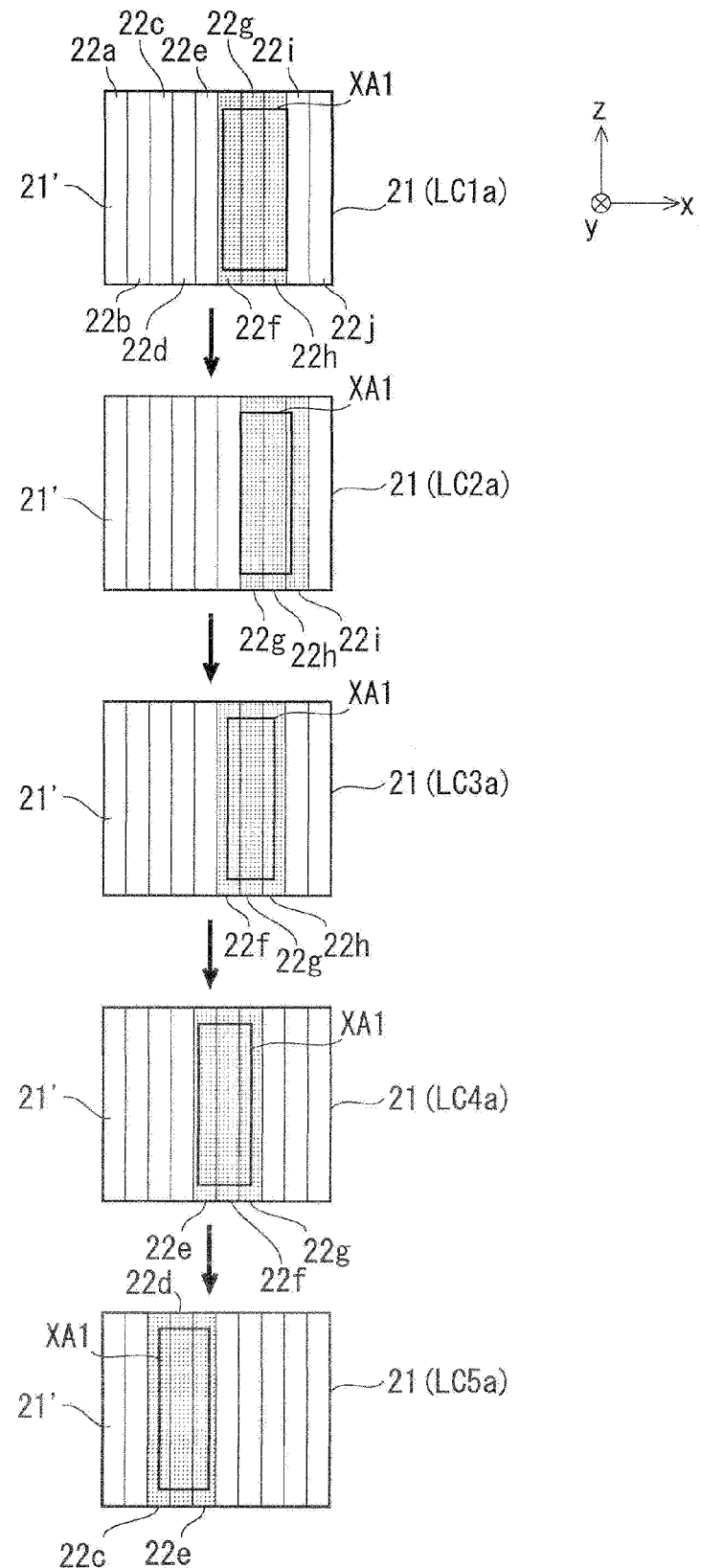

F I G . 2 6
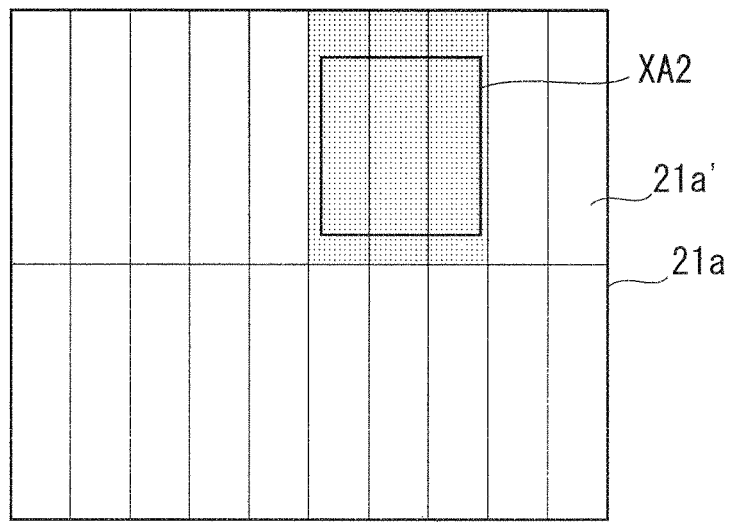

F I G . 3 0
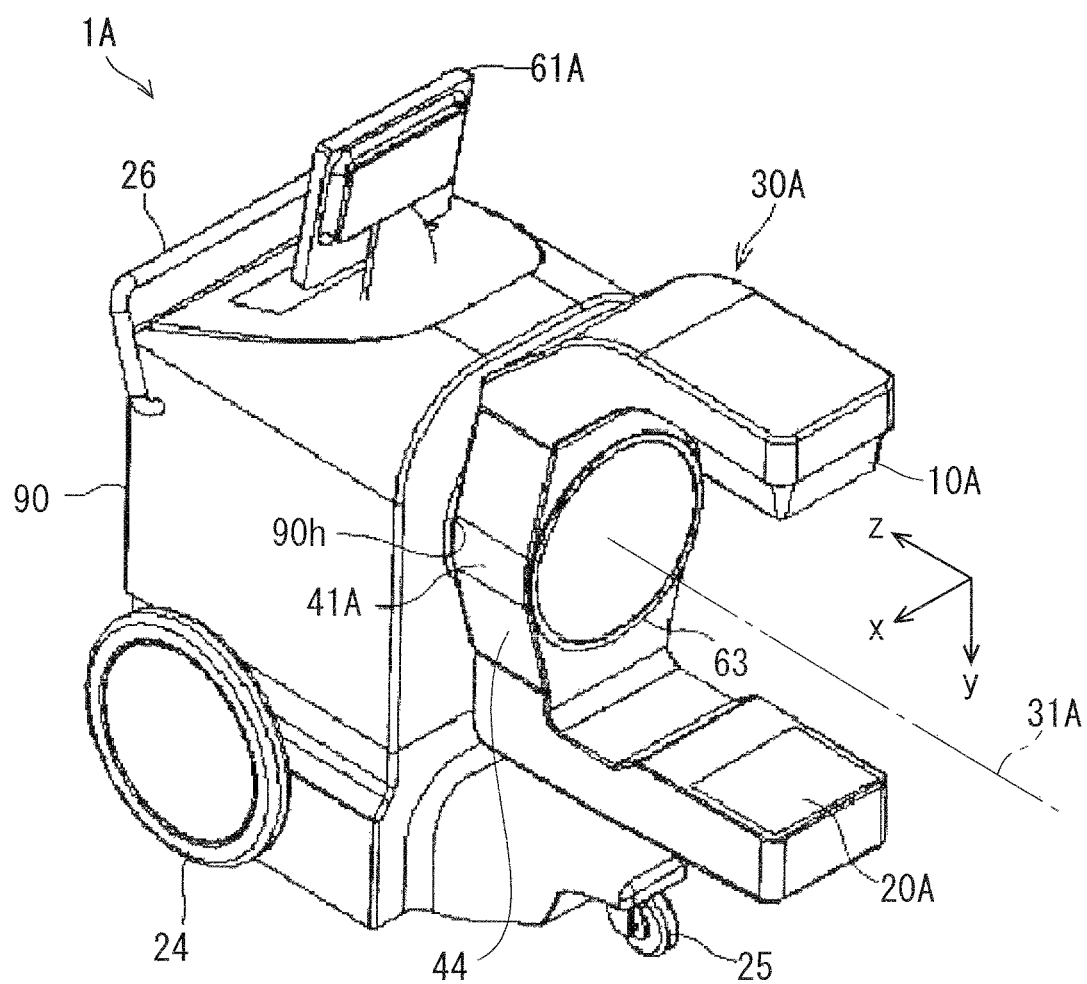

X-RAY CT PHOTOGRAPHIC APPARATUS

BACKGROUND OF THE INVENTION

1. Field of the Invention

The present invention relates to an apparatus for X-ray CT photography.

2. Description of the Background Art

Conventionally, X-ray CT photography is performed in a medical field and the like. In the X-ray CT photography, a subject is irradiated with an X-ray to collect projection data, and the obtained projection data is reconstructed on a computer to generate a CT (Computed (Computerized) Tomography) image.

In the X-ray CT photography, the subject is disposed between an X-ray generator and an X-ray detector, the X-ray generator and the X-ray detector turn about the subject, and the X-ray generator emits conical X-ray (an X-ray cone beam) to subject. The X-ray detector collects an X-ray detection result (the projection data), and three-dimensional data (volume data) is reconstructed based on the collected X-ray detection result. For example, Japanese Patent Application Laid-Open No. 2010-42121, PCT Application International Publication No. WO 2007/046372, and Japanese Patent Application Laid-Open No. 11-19078 (1999) disclose apparatuses that perform the X-ray CT photography.

Japanese Patent Application Laid-Open No. 2010-42121 discloses an X-ray CT photographic apparatus configured to perform both the X-ray CT photography and panoramic photography. In this apparatus, a detection signal is read from a whole X-ray detection surface of a planar X-ray receiver in the X-ray CT photography, and the X-ray detection signal is read in a limited way only from the point irradiated with an X-ray beam in the X-ray detection surface of a planar X-ray receiver in the panoramic photography.

PCT Application International Publication No. WO 2007/046372 discloses a medical digital X-ray photographic apparatus configured to be able to perform plural kinds of X-ray photography modes, and a read region of the X-ray detection signal of an X-ray sensor is changed in each mode.

In the X-ray CT photographic apparatus disclosed in Japanese Patent Application Laid-Open No. 11-19078 (1999), during the X-ray CT photography, a pair of channel collimators is displaced in front of an X-ray generator, and only an interest region of a subject (a patient) is irradiated with an X-ray such that a shape of CT photographic region (FOV (Field of View)) becomes a circle or an ellipse.

In the X-ray CT photographic apparatus disclosed in Japanese Patent Application Laid-Open No. 2010-42121, the X-ray detection signal is read from the whole surface of the X-ray detector during the X-ray CT photography. In performing local X-ray CT photography in which the X-ray CT photography is restricted to a local portion of the subject, although only part of the detection surface of the X-ray detector is irradiated with the X-ray, the X-ray detection signal is read from a portion that is not irradiated with the X-ray. Therefore, there is a risk of degrading transfer efficiency of the X-ray detection signal.

In the medical digital X-ray photographic apparatus disclosed in PCT Application International Publication No. WO 2007/046372, the read region of the X-ray detection signal is fixed during the X-ray CT photography. The useless X-ray detection signal is read in the case that the portion irradiated with the X-ray changes every moment in the detection surface of the X-ray detector during the X-ray CT photography. Accordingly, there is a risk of degrading the transfer efficiency of the X-ray detection signal.

In the X-ray CT photographic apparatus disclosed in Japanese Patent Application Laid-Open No. 11-19078 (1999), the portion irradiated with the X-ray changes in the detection surface of the X-ray detector by regulating an X-ray irradiation range. However, in this Japanese Patent Application Laid-Open No. 11-19078 (1999), there is no description about the read of the X-ray detection signal from the X-ray detector. Therefore, in the case that the X-ray detection signal is read from the whole detection surface, the read of the useless X-ray detection signal is generated to generate the risk of degrading the transfer efficiency of the X-ray detection signal.

SUMMARY OF THE INVENTION

The present invention is aimed at an X-ray CT photographic apparatus.

In accordance with an aspect of the present invention, an X-ray CT photographic apparatus includes: an X-ray generator that generates an X-ray; an X-ray regulating unit that regulates an irradiation range of the X-ray generated from the X-ray generator and shapes the X-ray into an X-ray cone beam; an X-ray regulating controller that controls the irradiation range of the X-ray by controlling the X-ray regulating unit; an X-ray detector that detects the X-ray cone beam transmitted through a subject on a detection surface; a read region controller that changes a read region, where an X-ray detection signal of the X-ray cone beam is read in the X-ray detector, according to the irradiation range of the X-ray cone beam; a support body that supports the X-ray generator and the X-ray detector while the X-ray generator and the X-ray detector are opposed to each other with the subject therebetween; a support body turning drive unit that turns the support body about a turning shaft and turns the X-ray generator and the X-ray detector about the subject during X-ray photography; and a CT photographic region setting unit that receives and sets a setting manipulation of a CT photographic region being a target of an X-ray CT photography in the subject, wherein, assuming that a z-axis direction is an axis direction of the turning shaft, that an x-axis direction and a y-axis direction are two directions orthogonal to each other on a two-dimensional plane orthogonal to the z-axis direction, and that a y-axis direction is a direction from the X-ray generator toward the X-ray detector in the x-axis direction and y-axis direction, the X-ray regulating controller changes the irradiation range of the X-ray cone beam to the x-axis direction during the X-ray CT photography such that only the set CT photographic region is irradiated with the X-ray cone beam according to the set CT photographic region input through the CT photographic region setting unit, and the read region controller changes the read region with respect to the x-axis direction in the detection surface during the X-ray CT photography.

According to the X-ray CT photographic apparatus of the aspect described above, the irradiation range of the X-ray cone beam is controlled with respect to the x-axis direction during the X-ray CT photography such that the set CT photographic region is irradiated with the X-ray cone beam. Therefore, an X-ray exposure dose of the subject can be reduced. During the X-ray CT photography, the read region of the X-ray detection signal in the X-ray detector is changed to the x-axis direction according to the X-ray cone beam. Therefore, the X-ray detection signal can efficiently be transferred.

Preferably, the X-ray regulating controller changes the irradiation range of the X-ray cone beam to the z-axis direction according to the set CT photographic region input through the CT photographic region setting unit before the X-ray CT photography, and the read region controller changes the read region with respect to the z-axis direction of the detection surface.

The irradiation range of the X-ray cone beam and the read region in the X-ray detector can be adjusted with respect to the z-axis direction.

Preferably, the CT photographic region setting unit displays an image relating to the subject on a display unit as a region assigning image, and receives a setting input of the set CT photographic region on the region assigning image.

The operator properly and easily sets the intended CT photographic region because the CT photographic region can be assigned on the image of the subject.

Preferably, the CT photographic region setting unit displays the region assigning image and a setting region image indicating the set CT photographic region while the region assigning image and the setting region image overlap with each other.

Whether the CT photographic region is properly set can be checked.

Preferably, the region assigning image includes a dental arch image that expresses a dental arch region.

The operator properly and easily sets the CT photographic region in the X-ray CT photography of the dental arch region.

Preferably, the dental arch image includes a curved line that expresses the curved dental arch region, and the CT photographic region setting unit receives an assignment manipulation to assign one end and the other end of the CT photographic region on the curved line.

The operator properly and easily sets the CT photographic region along the curved line of the dental arch region.

Preferably, the CT photographic region setting unit causes a user to select one of an upper jaw and a lower jaw of the subject as a setting target of the set CT photographic region.

The CT photographic region can be selectively set to one of the upper jaw and the lower jaw.

Preferably, the X-ray regulating unit includes an X-ray shield member that regulates a shielding amount of the X-ray, which is generated from the X-ray generator, according to the set CT photographic region.

The desired X-ray cone beam can be formed by adjusting the shielding amount.

Preferably, the X-ray CT photographic apparatus further includes a first support body retention unit that retains the support body while the axis direction of the turning shaft is fixed to a vertical direction.

The X-ray CT photography can be performed by turning the X-ray generator and the X-ray detection unit about the turning shaft along the vertical direction.

Preferably, the X-ray CT photographic apparatus further includes a second support body retention unit that retains the support body while the axis direction of the turning shaft is fixed to a horizontal direction.

The X-ray CT photography can be performed by turning the X-ray generator and the X-ray detection unit about the turning shaft along the horizontal direction.

Preferably, when viewed from the axis direction of the turning shaft, the set CT photographic region is set so as to become a circular shape.

Preferably, when viewed from the axis direction of the turning shaft, the set CT photographic region is set so as to become a substantially long-circle shape in which a longer direction extends along the dental arch region.

Preferably, when viewed from the axis direction of the turning shaft, the set CT photographic region is set so as to become a substantially semicircular shape or a substantially triangular shape, which connects an outer periphery of the dental arch region while a vertex portion is located near an anterior tooth.

The operator easily sets the CT photographic region such that the X-ray exposure dose of the subject is reduced while the interest region is included.

Preferably, the X-ray CT photographic apparatus further includes a photography mode switching unit that switches between a whole region CT photography mode in which the X-ray CT photography is performed in a whole region of the detection surface and a partial region CT photography mode in which the X-ray CT photography is performed in a partial region of the whole region of the detection surface, wherein, during the X-ray CT photography in the whole region CT photography mode, the X-ray regulating controller sets the irradiation range of the X-ray cone beam to the whole region of the detection surface, and the read region controller sets the whole region of the detection surface to the read region, and, during the X-ray CT photography in the partial region CT photography mode, the X-ray regulating controller changes the irradiation range of the X-ray cone beam to the x-axis direction such that only the set CT photographic region is irradiated with the X-ray cone beam, and the read region controller changes the read region in the detection surface to the x-axis direction.

The X-ray CT photography in which the read region is the whole region of the detection surface of the X-ray detector and the X-ray CT photography in which the detection surface is partially used while the read region is changed in the x-axis direction can be performed while switched to each other.

Preferably, the subject includes a dental arch, the X-ray regulating unit forms the X-ray in an X-ray slit beam that extends in the axis direction of the turning shaft, while the support body turning drive unit turns the support body, the X-ray regulating controller changes the irradiation range of the X-ray slit beam to the x-axis direction to perform panoramic photography such that the X-ray slit beam forms an envelope to irradiate the irradiation range of the X-ray slit beam therewith, and the read region controller changes the read region to the x-axis direction in the detection surface while correlating the read region with the irradiation range of the X-ray slit beam.

Not only the X-ray CT photography but also the panoramic photography can be performed.

Preferably, the read region controller changes a frame rate, at which data is read from the read region, according to a turning angle about the turning shaft of the support unit.

Image quality can be improved by raising the frame rate. Additionally, the X-ray detection signal can efficiently be transferred from the X-ray detector by lowering the frame rate.

Preferably, the read region controller includes a frame rate setting unit that changes a frame rate, at which data is read from the read region, according to a size of the CT photographic region, a kind of a photographic target area, a photographing purpose, or a position of the photographic target area.

The frame rate setting unit can set the frame rate according to the size of the CT photographic region, the kind of the photographic target area, the photographing purpose, or the position of the photographic target area.

As seen from the above, an object of the present invention is to provide a technology of efficiently transferring the X-ray detection signal from the X-ray detector.

The above described and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a partial front view of the X-ray CT photographic apparatus on which a cephalostat is mounted;

FIG. 9 is a schematic plan view illustrating loci of an X-ray generator, the transverse shield plate, and an X-ray detector when X-ray CT photography of an oval CT photographic region CAa is performed;

FIGS. 10 (FIGS. 10A and 10B), 11 (FIGS. 11A and 11B) and 12 (FIGS. 12A and 12B) are schematic plan views illustrating the X-ray generator, the transverse shield plate, and the X-ray detector when the X-ray CT photography of the oval CT photographic region CAa is performed;

FIG. 13 (FIGS. 13A and 13B) is an explanatory view of an X-ray cone beam in which an irradiation range is regulated with respect to a longitudinal direction;

FIGS. 14 to 17 are views illustrating another CT photographic region setting screen;

FIG. 18 is a schematic plan view illustrating loci of the X-ray generator, the transverse shield plate, and the X-ray detector when the X-ray CT photography of an elliptical CT photographic region CAb is performed;

FIG. 19 (FIGS. 19A through 19G) is a view illustrating a CT photographic region CA having another shape;

FIG. 22 is a schematic plan view illustrating a situation in which panoramic photography is performed;

FIG. 24 is an explanatory view of conventional CT photography in which the perfect-circle CT photographic region is used as the CT photographic region CA;

FIG. 25 is a view illustrating a situation in which a read region is changed in a detection surface of the X-ray detector;

FIG. 26 is a view illustrating a detection surface of another X-ray detector;

FIG. 30 is an overall perspective view of an X-ray CT photographic apparatus according to a second preferred embodiment.

DESCRIPTION OF THE PREFERRED EMBODIMENTS

Hereinafter, a preferred embodiment of the present invention will be described with reference to the accompanying drawings. In the accompanying drawings, for the sake convenience, sometimes the size or the number of pieces of each unit is magnified or simplified as needed.

1. First Preferred Embodiment

Figure 1:
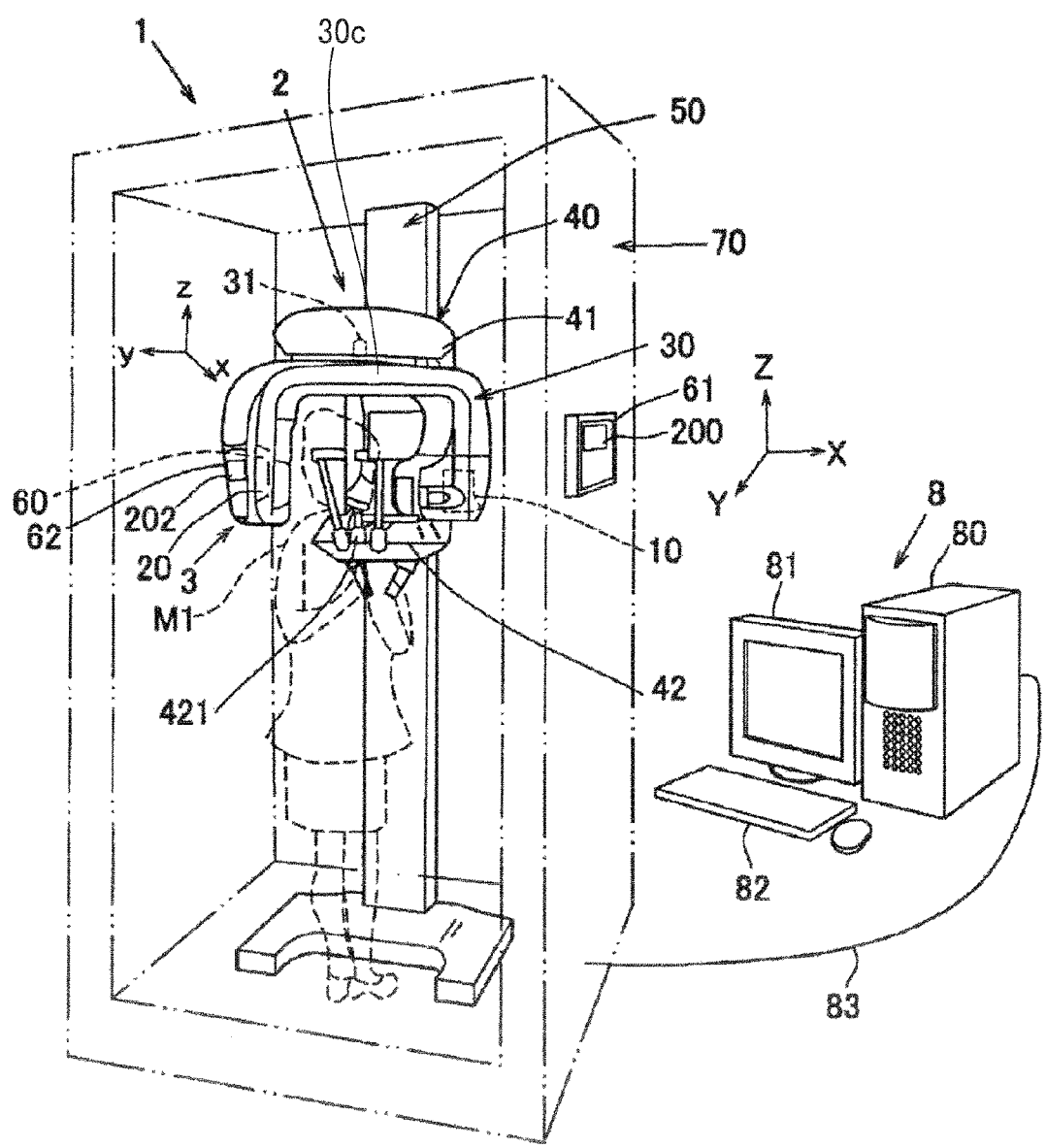
FIG. 1 is a schematic perspective view of an X-ray CT photographic apparatus according to a first preferred embodiment of the present invention.
Figure 3:
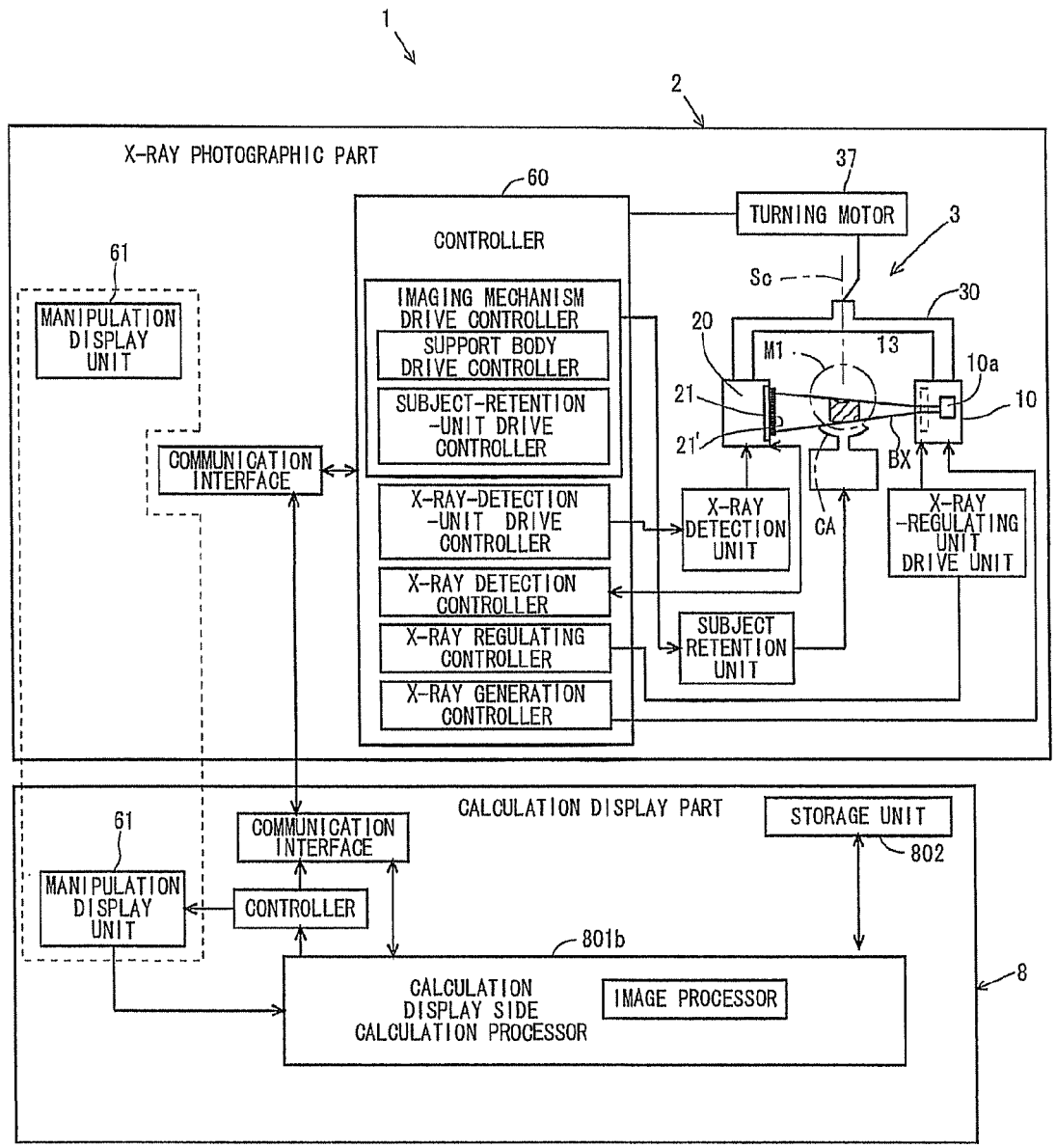
FIG. 3 is a block diagram of a configuration of the X-ray CT photographic apparatus.
Figure 4:
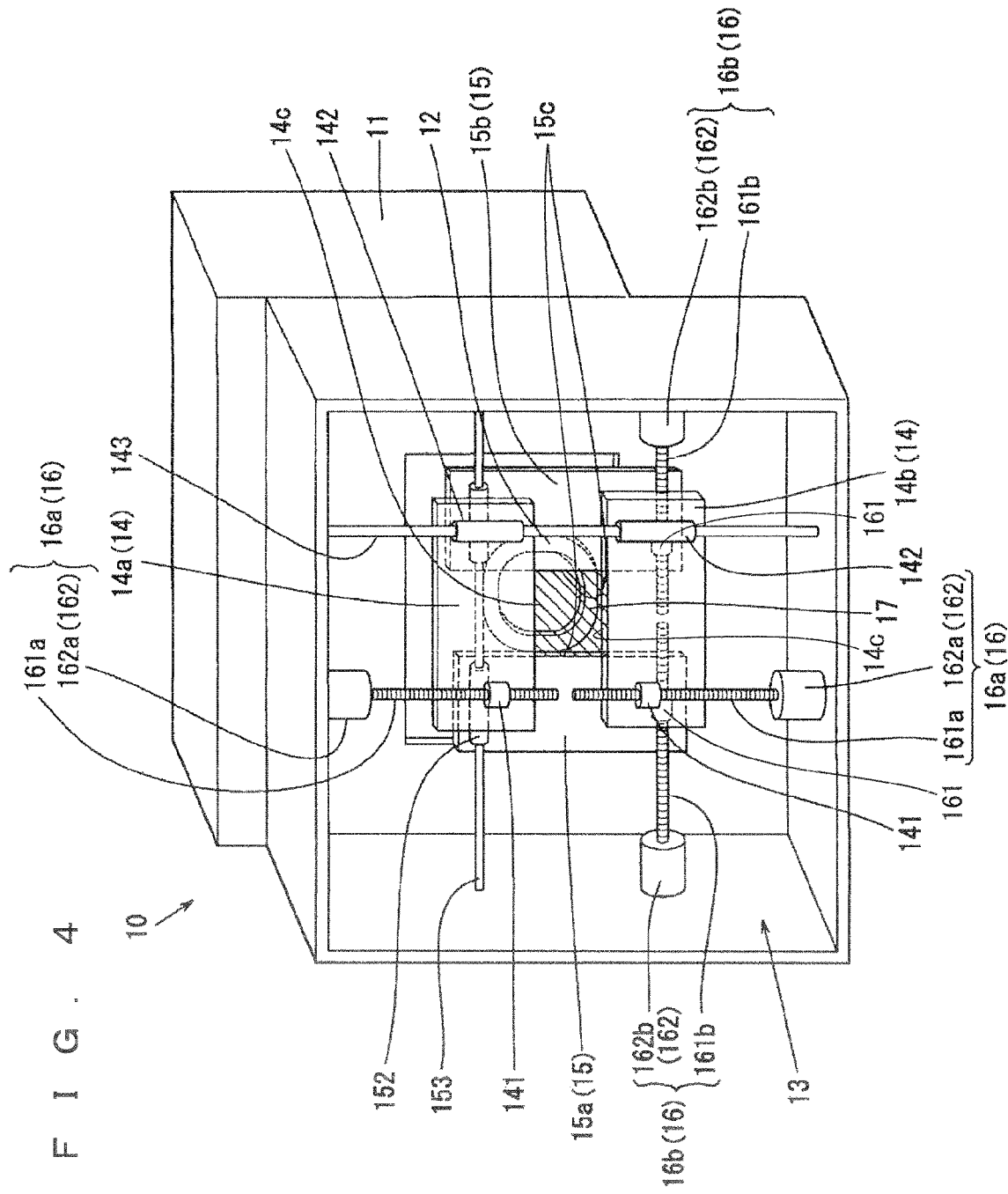
FIG. 4 is a schematic perspective view of a beam shaping n.

FIG. 1 is a schematic perspective view of an X-ray CT photographic apparatus 1 according to a first preferred embodiment of the present invention. FIG. 2 is a partial front view of the X-ray CT photographic apparatus 1 on which a cephalostat 43 is mounted. FIG. 3 is a block diagram illustrating a configuration of the X-ray CT photographic apparatus 1. FIG. 4 is a schematic perspective view of a beam shaping mechanism 13 (the X-ray regulating unit).

Figure 5:
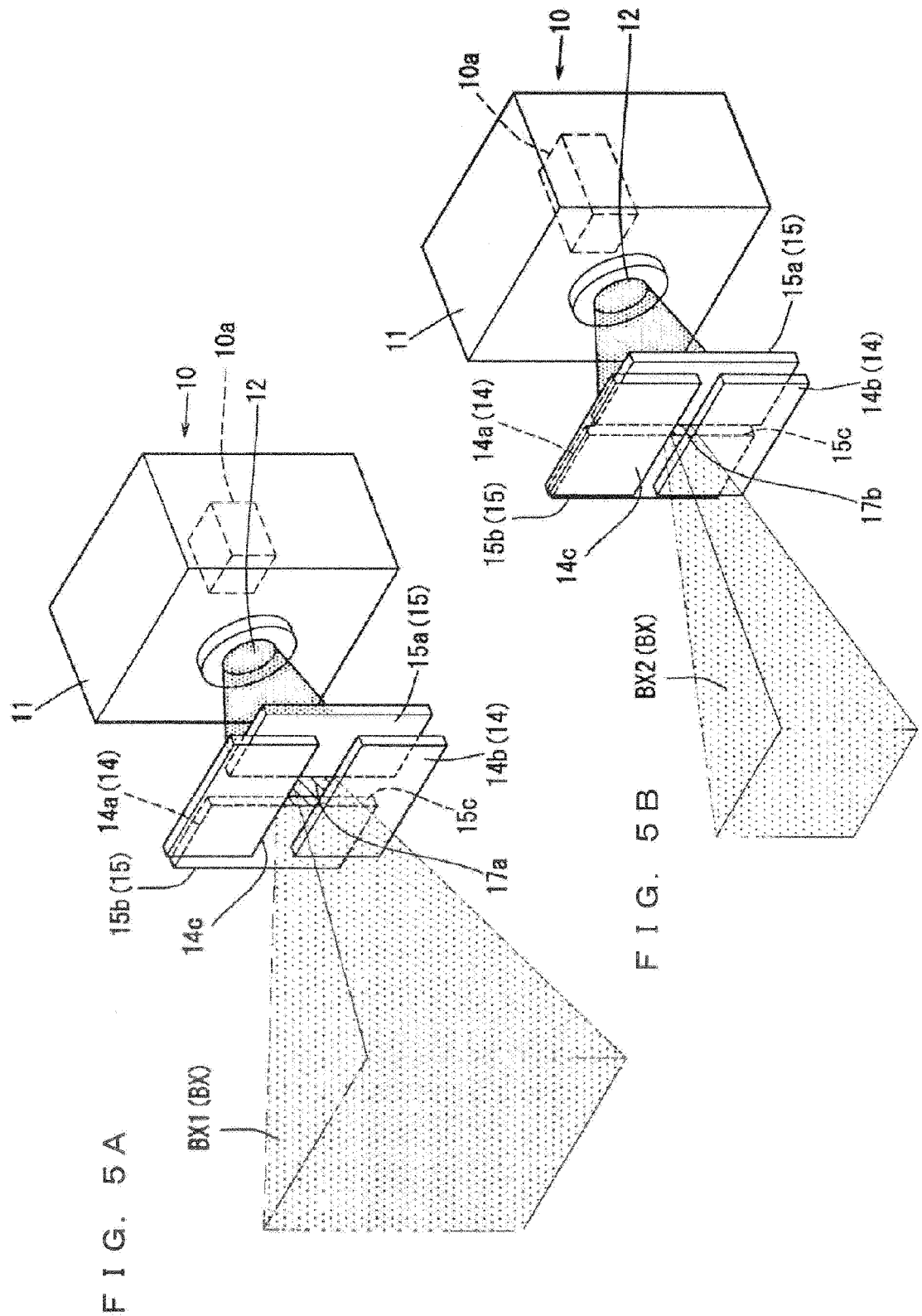
FIG. 5 (FIGS. 5A and 5B) is a schematic perspective view of an X-ray generator that emits an X-ray cone beam in which an irradiation range is regulated.

FIG. 5 (FIGS. 5A and 5B) is a schematic perspective view of an X-ray generation unit 10 that emits an X-ray cone beam BX in which an irradiation range is regulated. Particularly, FIG. 5A is a schematic perspective view of the X-ray generation unit 10 that emits an X-ray cone beam BX1 for large irradiation field CT, and FIG. 5B is a schematic perspective view of the X-ray generation unit 10 that emits an X-ray cone beam BX2 for small irradiation field CT.

Figure 6:
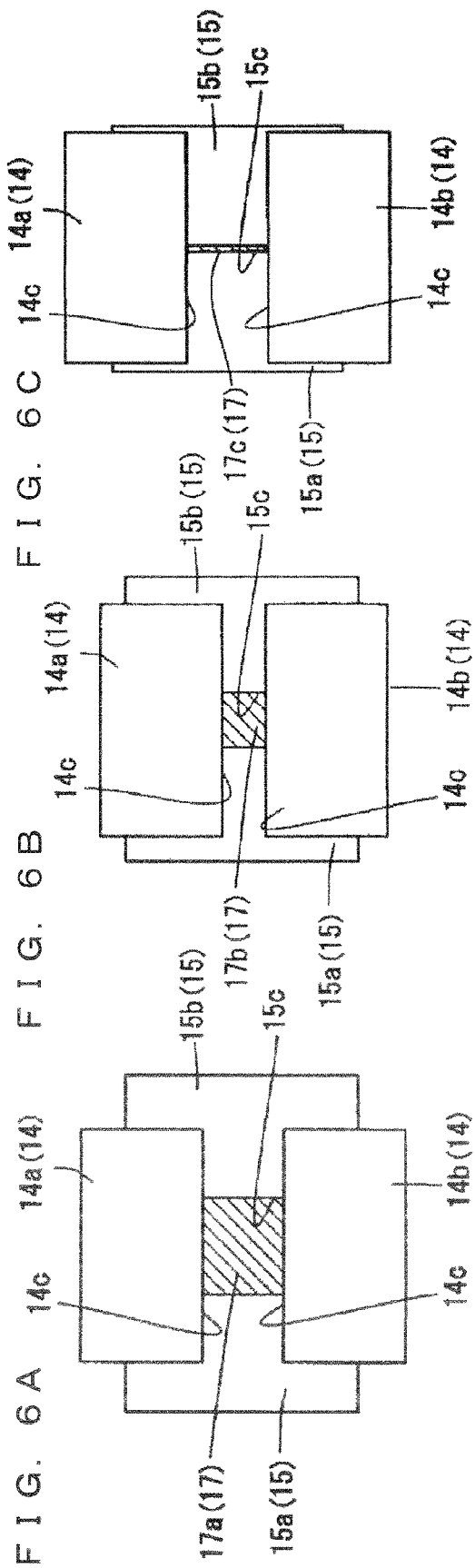
FIGS. 6 (FIGS. 6A through 6C) and 7 (FIGS. 7A through 7C) are explanatory views of positioning of a longitudinal shield plate and a transverse shield plate.

FIG. 6 (FIGS. 6A through 6C) is an explanatory view of positioning of a longitudinal shield plate 14 and a transverse shield plate 15. Particularly, FIG. 6A is a front view illustrating the positioning of the longitudinal shield plate 14 and the transverse shield plate 15 when an irradiation direction (or the irradiation range) of the X-ray cone beam BX is regulated for the large irradiation field CT. FIG. 6B is a front view illustrating the positioning of the longitudinal shield plate 14 and the transverse shield plate 15 when the irradiation range of the X-ray cone beam BX is regulated for the small irradiation field CT. FIG. 6C is a front view illustrating the positioning of the longitudinal shield plate 14 and the transverse shield plate 15 when the X-ray irradiation range is formed into an X-ray slit beam BXP (see FIG. 22) and regulated for panoramic photography.

Figure 7:
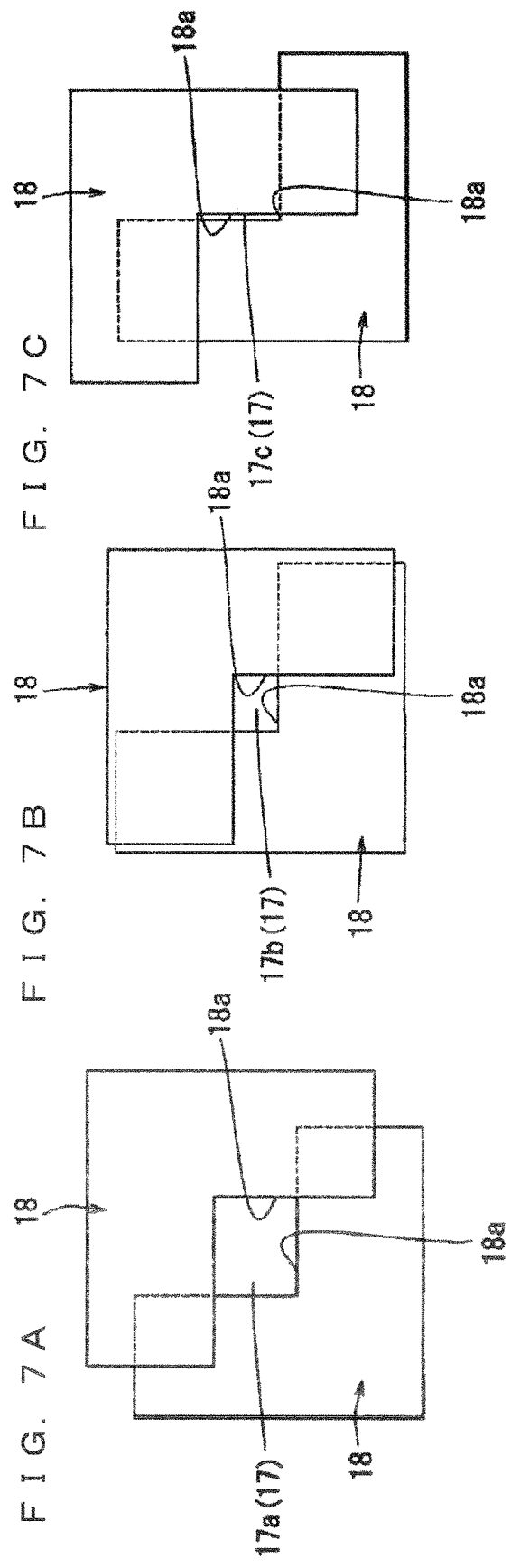

FIG. 7 (FIGS. 7A through 7C) is an explanatory view of the positioning of the longitudinal shield plate 14 and the transverse shield plate 15. FIGS. 7A, 7B, and 7C illustrate the case in which a state similar to that in FIGS. 6A, 6B, and 6C is performed by an L-shape shield plate 18.

The X-ray CT photographic apparatus 1 is roughly divided into three components: a manipulation display unit 61, a main body 2, and an information processing device 8. The manipulation display unit 61 sets an oval CT photographic region CAa (see FIG. 9) in which an interest region has an oval shape, and the manipulation display unit 61 acts as a display means. The main body 2 collects a projection data group by performing X-ray CT photography to the oval CT photographic region CAa set by the manipulation display unit 61. The information processing device 8 generates various images by processing the projection data group collected by the main body 2.

A main body controller 60 of the main body 2, a controller of the information processing device 8, and a calculation processor 801*b* (see FIG. 3) perform X-ray photography according to a program IMP (not illustrated) for the X-ray photography including the X-ray CT photography. In the program IMP, an image display step S100, an overlapping display step S110, a setting manipulation receiving step S120, and an X-ray regulating step S130 are performed in this order.

Preferably, the main body 2 is accommodated in a hollow, longitudinally long, rectangular solid X-ray protection chamber 70 in a site of the X-ray photography. The main body 2, the manipulation display unit 61 mounted on a wall surface of the X-ray protection chamber 70, and the information processing device 8 disposed outside the X-ray protection chamber 70 are connected to one another using a connection cable 83.

The main body 2 includes the X-ray generation unit 10 that emits the X-ray cone beam BX or X-ray slit beam BXP, which is constructed by an X-ray bundle, toward a subject M1 and an X-ray detection unit 20 that detects the X-ray beam, which is transmitted through the subject M1 after emitted from the X-ray generation unit 10. The main body 2 also includes a turning arm 30 that is of a support body supporting the X-ray generation unit 10 and X-ray detection unit 20, a support post 50 that extends vertically, a lifting unit 40 that can vertically be lifted with respect to the support post 50 while suspending the turning arm 30, and the main body controller 60. The X-ray generation unit 10, the X-ray detection unit 20, and a beam shaping mechanism 13 disposed on the side of the X-ray detection unit 20 with respect to the X-ray generation unit 10 constitute an imaging mechanism 3.

The X-ray generation unit 10 and the X-ray detection unit 20 are suspended from and fixed to both end portions of a turning unit 30*c* of the turning arm 30, respectively. The X-ray generation unit 10 and the X-ray detection unit 20 are supported so as to be opposed to each other. The turning arm 30 is suspended from and fixed to the lifting unit 40 with a vertically extending turning shaft 31 interposed therebetween.

The turning arm 30 has a substantially inverted U-shape when viewed from the front side, and the turning arm 30 turns with the turning shaft 31 provided in an upper end portion of a turning unit 30*c* as a turning center Sc (see FIG. 9). In the first preferred embodiment, the lifting unit 40 includes an upper frame 41 that extends toward the front side from an upper portion of the lifting unit 40 when viewed from the front side, and the turning center Sc is fixed to the upper frame 41.

The turning arm 30 of the first preferred embodiment is formed into the U-shape. Alternatively, the turning arm 30 may be formed into another shape. For example, an annular member that is rotatably fitted in an outer circumferential portion of a columnar-shaped member with a ball bearing interposed therebetween may be used as the turning arm. In this case, the X-ray generation unit 10 and the X-ray detection unit 20 are attached to the annular member so as to be opposed to each other with the subject M1 therebetween.

Hereinafter, a direction (in the first preferred embodiment, a vertical direction namely, a longitudinal direction) parallel to an axis direction of the turning shaft 31 is referred to as a "Z-axis direction", a direction intersecting the Z-axis direction is referred to as an "X-axis direction", and a direction intersecting the X-axis direction and Z-axis direction is referred to as a "Y-axis direction" (XYZ orthogonal coordinate system). The X-axis direction and the Y-axis direction may arbitrarily be defined. However, in the first preferred embodiment, when a test person who is of the subject M1 is positioned in the X-ray CT photographic apparatus 1 to face the support post 50 in correct position, a side-to-side direction of the test person is defined as the X-axis direction, and a front-back direction of the test person is defined as the Y-axis direction. In the first preferred embodiment, it is assumed that the X-axis direction, the Y-axis direction, and the Z-axis direction are orthogonal to one another. Hereinafter, sometimes the Z-axis direction is referred to as the vertical direction, and a direction on a plane defined by a two-dimensional direction of the X-axis direction and Y-axis direction is referred to as a horizontal direction. The X-axis direction and the Y-axis direction are two directions orthogonal to each other on a two-dimensional plane orthogonal to the Z-axis direction.

On the other hand, as to a three-dimensional coordinate on the turning arm 30, a direction in which the X-ray generation unit 10 and the X-ray detection unit 20 are opposed to each other is referred to as a "y-axis direction", a horizontal direction orthogonal to the y-axis direction is referred to as an "x-axis direction" and a vertical direction orthogonal to the x-axis direction and y-axis direction is referred to as a "z-axis direction" (xyz orthogonal coordinate system). In the first preferred embodiment and following preferred embodiments, the z-axis direction and the Z-axis direction are parallel to each other. The turning arm 30 of the first preferred embodiment turns with the turning shaft 31 extending in the vertical direction as a rotating axis. Accordingly, the xyz orthogonal coordinate system rotates about the Z-axis (equals the z-axis) with respect to the XYZ orthogonal coordinate system. The x-axis direction and the y-axis direction are two directions orthogonal to each other on a two-dimensional plane orthogonal to the z-axis direction.

When the X-ray generation unit 10 and X-ray detection unit 20 in FIG. 1 are viewed from above, the direction from the X-ray generation unit 10 toward the X-ray detection unit 20 is referred to as a (+y) direction, a horizontal right-hand direction (in FIG. 1, the left-hand direction when the X-ray generation unit 10 is viewed from the side of the X-ray detection unit 20) orthogonal to the (+y) direction is referred to as a (+x) direction, and an upward direction of the vertical direction is referred to as a (+z) direction.

The lifting unit 40 includes the upper frame 41 (the first support body retention unit) and a lower frame 42, and engages the support post 50 that is vertically provided along the vertical direction. The turning shaft 31 is attached to the upper frame 41 that acts as the support body retention unit. The lifting unit 40 moves in the vertical direction along the support post 50, whereby the turning arm 30 moves up and down.

As to the structure that turns the turning arm 30, the turning unit 30*c* of the turning arm 30 may be provided while being able to turn with respect to the turning shaft 31 fixed to the upper frame 41, and the turning arm 30 may turn with respect to the turning shaft 31. Alternatively, the turning unit 30*c* of the turning arm 30 may be fixed to the turning shaft 31, which is provided while being able to turn with respect to the upper frame 41, and the turning arm 30 may be turned by turning the turning shaft 31.

For the former structure described above, for example, a torque of the turning motor 37 is employed so that it acts on the rotation of the turning arm 30, to which the turning motor 37 is fixed, using a power transmission mechanism (not illustrated) such as a belt and a pulley. For example, the turning motor 37 (the support body turning drive unit) is fixed to the inside of the turning arm 30, and a circular belt is entrained about both the pulley fixed to the rotating shaft of the turning motor 37 and the turning shaft 31, which allows the torque of the turning motor 37 to act on the rotation of the turning arm 30 to which the turning motor 37 is fixed. In this case, a bearing member such as a bearing may be interposed between the turning shaft 31 and the turning unit 30c.

Alternatively, the turning motor 37 that turns the turning arm 30 about the turning shaft 31 may be provided in the upper frame 41, and the transmission mechanism (not illustrated), which includes a belt, a pulley, and a rotating shaft may transmit the torque of the turning motor to the turning arm 30 to turn the turning arm 30 through the turning shaft 31.

Like the latter structure described above, the turning unit 30c of the turning arm 30 may be fixed to the turning shaft 31, which is provided while being able to turn with respect to the upper frame 41, and the turning arm 30 may be turned by turning the turning shaft 31. In this case, the turning motor 37 is fixed to the inside of the upper frame 41, and the torque of the turning motor 37 acts on the rotation of the turning shaft 31 using the transmission mechanism (not illustrated) such as a roller. In this structure, the bearing member may be interposed between the turning shaft 31 and the upper frame 41.

In the first preferred embodiment, the turning shaft 31 is configured to extend along the vertical direction. Alternatively, the turning shaft 31 can be obliquely disposed with an arbitrary angle with respect to the vertical direction.

A bearing (not illustrated) is interposed between the turning shaft 31 and the turning arm 30. Therefore, the turning arm 30 can rotate smoothly with respect to the turning shaft 31. The turning shaft 31, the transmission mechanism that includes the bearing, the belt, the pulley, and the rotating shaft, and the turning motor 37 make an example of the turning mechanism that turns the turning arm 30. In the first preferred embodiment, the turning arm 30 turns with respect to the turning shaft 31 that is fixed to a fixed position so as not to rotate. However, as described above, the turning arm 30 may be turned by rotating the turning shaft 31 fixed to the turning arm 30 with respect to the upper frame 41. In this case, the bearing that rotatably supports the turning shaft 31 is formed on the side of the upper frame 41.

A subject fixing unit 421 including an ear rod and a chin rest is provided in the lower frame 42. The ear rod fixes the subject M1 (in the first preferred embodiment, the head of a human body) from both sides, and the chin rest fixes the jaw of the subject M1.

The turning arm 30 is disposed in a proper position by lifting and lowering the lifting unit 40 according to the height of the subject M1. At this point, the subject M1 is fixed to the subject fixing unit 421. In FIG. 1, the subject fixing unit 421 retains the subject M1 such that the body axis of the subject M1 becomes substantially the same direction as the axis direction of the turning shaft 31.

The main body controller 60 is a controller that controls the operation of each configuration of the main body 2. For example, the main body controller 60 acts as an X-ray regulating controller and a drive controller. As illustrated in FIG. 1, the main body controller 60 is disposed in the X-ray detection unit 20.

A manipulation display unit 62 is attached to a surface outside the main body controller 60, namely, on the side in the +Y direction of the X-ray detection unit 20. The manipulation display unit 62 is constructed by buttons that are used to input various instructions or a touch panel that displays various pieces of information.

The manipulation display unit 61 is attached to an outside surface of the wall of the X-ray protection chamber 70 that accommodates the main body 2 therein. The manipulation display unit 61 is connected to the main body controller 60, and constructed by buttons that are used to input various instructions or a touch panel that displays various pieces of information.

The operator (for example, a practitioner) may manipulate the main body 2 using the manipulation display unit 62, or manipulate the main body 2 using the manipulation display unit 61. The manipulation display unit 62 may differ from the manipulation display unit 61 in a manipulation content or a display content, or part or whole of the manipulation content or display content may be common to the manipulation display unit 62 and the manipulation display unit 61.

In the case that the X-ray protection chamber 70 is eliminated, the manipulation display unit 61 may be also eliminated. One of the manipulation display unit 62 and the manipulation display unit 61 may be eliminated. The display and manipulation performed by the manipulation display unit 61 are described below. However, the display and manipulation performed by the manipulation display unit 61 may be replaced with the display and manipulation performed by the manipulation display unit 62.

The manipulation display unit 61 is also used to assign a position of a photographic region of a biological organ or the like. There are various modes in the X-ray photography, and the mode may be selected by the manipulation of the manipulation display unit 61.

Figure 8:
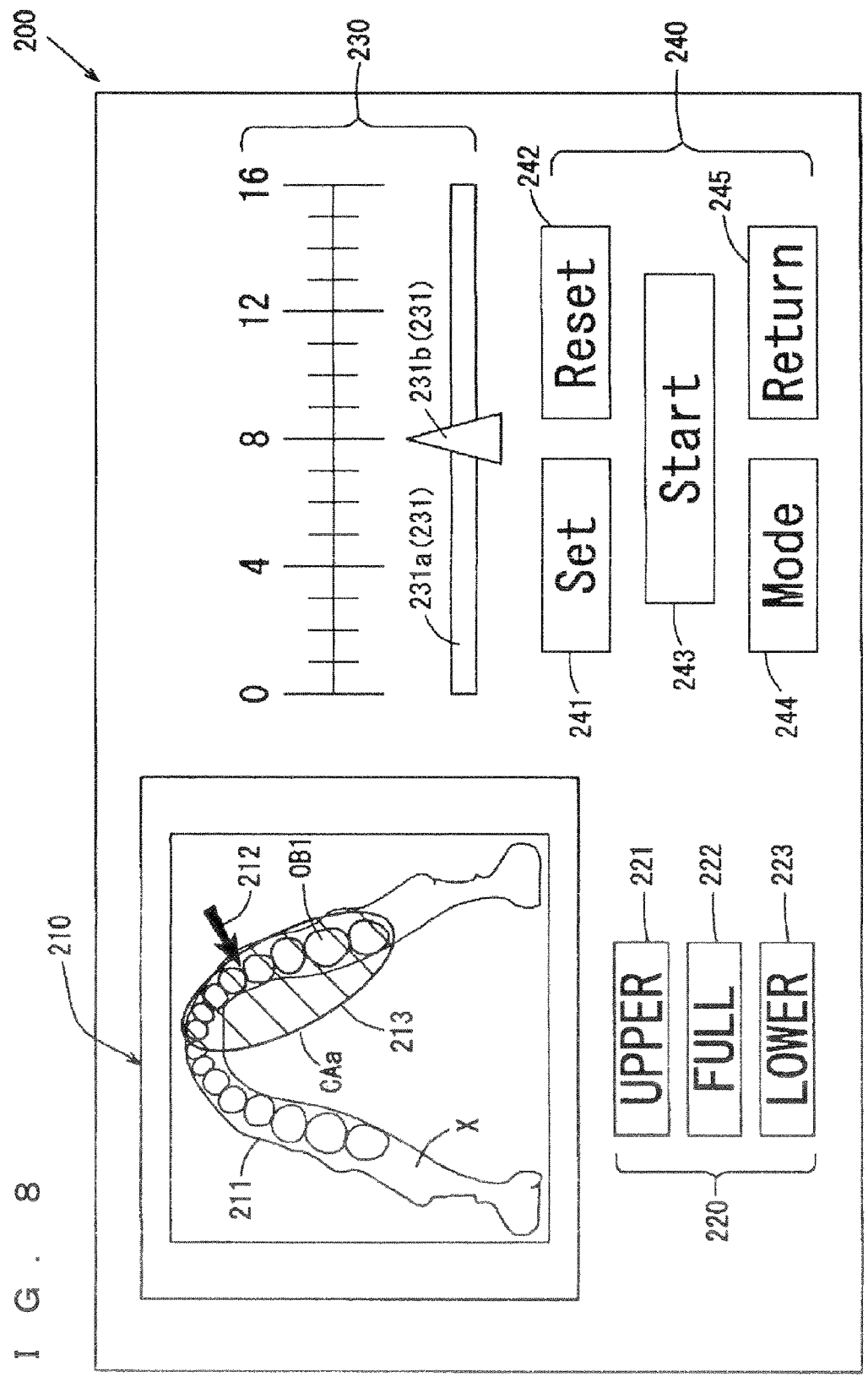
FIG. 8 is a view illustrating an example of a CT photographic region setting screen.

FIG. 8 is a view illustrating an example of a CT photographic region setting screen 200. The CT photographic region setting screen 200 in FIG. 8 is displayed on the manipulation display unit 61 in order to set the oval CT photographic region CAa. The oval CT photographic region CAa is an example of the set CT photographic region. In the case that the CT photographic region setting screen 200 is displayed on the manipulation display unit 62, a CT photographic region setting screen 202 (see FIG. 1) similarly to the CT photographic region setting screen 200 is displayed on the manipulation display unit 62.

The CT photographic region setting screen 200 that acts as a CT photographic region setting means (the CT photographic region setting unit) includes an image display unit 210 that displays a dental arch image 211 and an upper-and-lower-jaw selection unit 220, a selection range setting unit 230, and a condition setting unit 240. The image display unit 210 displays the dental arch image 211 expressing a shape in which a curved dental arch region is expressed by a curved line. The CT photographic region setting screen 200 in FIG. 8 is an oval mode setting screen in which the oval CT photographic region CAa having the oval shape along the arch-like curved line constituting the dental arch is set with respect to a dental arch region X.

An assigning cursor (a pointer) 212 and a CT photographic region line 213 (the setting region image) are displayed on the image display unit 210 while the assigning cursor 212 and the CT photographic region line 213 each overlap the displayed dental arch image 211 (overlapping display step S110). The assigning cursor 212 assigns the center in a longer direction of the oval CT photographic region CAa that is set with respect to the displayed dental arch image 211 (the image display step S100). The CT photographic region line 213 is an oval, which is assigned by an selection range setting unit 230 with respect to the center assigned by the assigning cursor 212 according to the number of teeth surrounded by the oval CT photographic region CAa, and is a setting region image indicating the set CT photographic region. The dental arch image 211 is an image expressing a jawbone (in the first preferred embodiment, the jaw) viewed from the body axis direction.

In the CT photographic region setting screen 200 in FIG. 8, the dental arch is viewed from the axis direction of the turning shaft 31. The oval shape of the oval CT photographic region CAa is also viewed from the axis direction of the turning shaft 31.

Strictly, the set CT photographic region (in the example in FIG. 8, the oval CT photographic region CAa) displayed by the photographic region line 213 is distinguished from a CT photographic region on an actual three-dimensional space. Preferably, the set CT photographic region on the display is set so as to substantially correspond to the CT photographic region on the actual three-dimensional space. However, in order that the operator (the practitioner) easily recognizes the set CT photographic region on the display, the set CT photographic region on the display may be displayed while slightly deformed with respect to the CT photographic region on the actual three-dimensional space.

The upper-and-lower-jaw selection unit 220 includes an upper button 221 that sets the oval CT photographic region CAa to an upper jaw, a full button 222 that sets the oval CT photographic region CAa to both upper and lower jaws, and a lower button 223 that sets the oval CT photographic region CAa to the lower jaw.

The selection range setting unit 230 includes a scale 231a in which the number of teeth is set in steps of one tooth and a slide setting unit 231 that assigns the desired number of teeth. The slide setting unit 231 includes scale 231a and a slider 231b that slides on the scale 231a.

The condition setting unit 240 includes a set button 241, a reset button 242, a start button 243, a mode button 244, and a return button 245. The set button 241 is manipulated to determine an assignment content of the oval CT photographic region CAa, which is set through the image display unit 210, the upper-and-lower-jaw selection unit 220, and the selection range setting unit 230 (the setting manipulation receiving step S120). The reset button 242 is manipulated to reset the assignment content of the oval CT photographic region CAa, which is set through the image display unit 210, the upper-and-lower-jaw selection unit 220, and the selection range setting unit 230.

The start button 243 is manipulated to issue an instruction to start the X-ray CT photography of the oval CT photographic region CAa based on the assignment content determined by the set button 241. The mode button 244 is manipulated to select various modes. In the first preferred embodiment, the mode button 244 is manipulated to switch the setting mode between an oval mode and a perfect-circle mode. The oval CT photographic region CAa suitable to assign the region including the plural teeth is set in the oval mode, and a perfect-circle CT photographic region CAd having a perfect-circle shape with respect to the local photographic object in the dental arch region X is set in the perfect-circle mode. In the case that the X-ray CT photographic apparatus 1 can perform the panoramic photography, the X-ray CT photography mode and the panoramic mode can be switched using the mode button 244. The panoramic mode is a mode in which the panoramic photography (panoramic X-ray photography) is performed, and a panoramic image is a panoramic X-ray image. In other words, the mode button 244 acts as a photography mode switching unit that switches the photography mode performed by the X-ray CT photographic apparatus 1 between the X-ray CT photography in which the various shapes are set to the CT photographic region and the panoramic photography.

The return button 245 is manipulated to return to the initial screen (not illustrated). In the first preferred embodiment, the manipulation display unit 61 is constructed by the touch panel, and the setting manipulation of the oval CT photographic region CAa is received by manipulating the assigning cursor 212 displayed on the CT photographic region setting screen 200. Alternatively, the manipulation display unit 61 may be constructed by a liquid crystal screen, and the setting manipulation of the CT photographic region CA may be received using a pointing device such as a mouse or a manipulation button provided near the manipulation display unit 61.

In the first preferred embodiment, the CT photographic region setting screen 200 is displayed on the manipulation display unit 61 to receive the setting manipulation of the CT photographic region CA. Alternatively, the CT photographic region setting screen 200 may be displayed on a display unit 81 of the information processing device 8 described later, and the setting manipulation of the CT photographic region CA may be received on the information processing device 8.

For example, the information processing device 8 includes the information processing main body 80, the display unit 81 that is constructed by a display device such as a liquid crystal monitor, and a manipulation unit 82 that is constructed by a keyboard and a mouse. The operator (the practitioner or the like) can input various instructions to the information processing device 8 through the manipulation unit 82. The display unit 81 may be constructed by the touch panel. In this case, the display unit 81 may include some of or all the functions of the manipulation unit 82. The display unit 81 and the manipulation unit 82 are the elements constituting the manipulation display unit 61 on the information processing device side.

For example, the information processing main body 80 is constructed by a computer or a workstation. The information processing main body 80 transmits and receives various pieces of data to and from the main body 2 through the connection cable 83 that is of the communication cable. Alternatively, the main body 2 and the information processing main body 80 may conduct data communication with each other by wireless communication.

The information processing device 8 processes projection data acquired by the main body 2, and reconstructs three-dimensional data (volume data) expressed by a voxel. For example, assuming that a specific plane is set in the three-dimensional data, the tomographic image can be reconstructed in the specific plane.

As illustrated in FIG. 2, the cephalostat 43 may be mounted on the X-ray CT photographic apparatus 1. For example, the cephalostat 43 can be attached to an arm 501 that extends horizontally from the middle of the lifting unit 40. The cephalostat 43 includes a fixture 431 that fixes the head of a subject to a fixed position and a cephalo photographing X-ray detector 432. For example, a cephalostat disclosed in Japanese Patent Application Laid-Open No. 2003-245277 or that of similar kinds may be used as the cephalostat 43.

<Beam Shaping by Beam Shaping Mechanism 13>

The beam shaping mechanism 13, which regulates the irradiation range of the X-ray generated by the X-ray generation unit 10 by shielding and forms the X-ray cone beam BX spread into a truncated-pyramid shape toward the X-ray detection unit 20, will be described below with reference to FIGS. 4 to 7.

In the turning arm 30, the X-ray generation unit 10 that is disposed while being opposed to the X-ray detection unit 20 includes an X-ray generator 10a constructed by an X-ray tube accommodated in a housing 11. An outgoing port 12 that permits transmission of the X-ray generated in the X-ray tube is provided in a front surface of the housing 11. The beam shaping mechanism 13 is disposed in front of the outgoing port 12 (on the front side in FIG. 4, and in the y-axis direction with respect to the X-ray generation unit 10).

The beam shaping mechanism 13 includes the longitudinal shield plate 14 that is moved in the longitudinal direction (the z-axis direction) to shield the X-ray irradiation direction, and the transverse shield plate 15 that is moved in the transverse direction (the x-axis direction) to shield the X-ray irradiation direction, and a shield plate moving mechanism 16 that moves the longitudinal shield plate 14 and the transverse shield plate 15. The main body controller 60 (the X-ray regulating controller) controls the beam shaping mechanism 13. The longitudinal shield plate 14 and the transverse shield plate 15 are an example of the X-ray shield member that is used to regulate a shielding amount of the X-ray generated from the X-ray generator 10*a*.

The longitudinal shield plate 14 includes a transversely-long-plate-like upper-side longitudinal shield plate 14*a* and a long-plate-like lower-side longitudinal shield plate 14*b*, which are disposed in the upper and lower sides (a +z side and a −z side) of the outgoing port 12 when viewed from the front side, respectively. The transverse shield plate 15 includes a transverse-long-plate-like left-hand transverse shield plate 15*a* and a transverse-long-plate-like right-hand transverse shield plate 15*b*, which are disposed in the left and right sides (a −x side and a +x side) of the outgoing port 12 when viewed from the front side, respectively. In FIG. 4, the transverse shield plate 15 is disposed on the side (a −y side) of the housing 11 of the longitudinal shield plate 14. Alternatively, the longitudinal shield plate 14 may be disposed on the side of the housing 11 of the transverse shield plate 15.

The shield plate moving mechanism 16 includes a pair of shield plate longitudinally moving mechanisms 16*a* that moves the upper-side longitudinal shield plate 14*a* and the lower-side longitudinal shield plate 14*b* in the longitudinal direction and a pair of shield plate transversely moving mechanisms 16*b* that moves the left-hand transverse shield plate 15*a* and the right-hand transverse shield plate 15*b* in the transverse direction.

The shield plate longitudinally moving mechanism 16*a* includes a nut member 141 that is attached to each of the upper-side longitudinal shield plates 14*a* and the lower-side longitudinal shield plate 14*b*, a longitudinal screw shaft 161*a* that extends in the longitudinal direction while engaging the nut member 141, and a positioning motor 162*a* (162) that normally and reversely rotates the screw shaft 161*a*. The screw shaft 161*a* is normally and reversely rotated by driving the positioning motor 162*a*, whereby the nut member 141 moves up and down along the longitudinal direction. Therefore, the upper-side longitudinal shield plate 14*a* and the lower-side longitudinal shield plate 14*b* move separately in the longitudinal direction. Based on the control of the main body controller 60, the shield plate longitudinally moving mechanism 16*a* adjusts the shielding amount in the longitudinal direction of the X-ray beam emitted from the X-ray generator 10*a* using the upper-side longitudinal shield plate 14*a* and the lower-side longitudinal shield plate 14*b*. The shield plate longitudinally moving mechanism 16*a* is an example of a longitudinal irradiation position controller that adjusts X-ray beam spread (the irradiation range) in the longitudinal direction to control the irradiation direction (a direction in which a center line of the irradiation range extends).

A regulating cylindrical body 142 is attached to each of the upper-side longitudinal shield plate 14*a* and the lower-side longitudinal shield plate 14*b*. A through-hole is made in the regulating cylindrical body 142 so as to pierce the regulating cylindrical body 142 along the longitudinal direction. A regulating shaft 143 extending in the longitudinal direction is fitted in the regulating cylindrical body 142, and the regulating shaft 143 regulates the longitudinal movement of the regulating cylindrical body 142. Therefore, the upper-side longitudinal shield plate 14*a* and the lower-side longitudinal shield plate 14*b* move in the longitudinal direction while not being inclined.

The shield plate transversely moving mechanism 16*b* includes a nut member 161 that is attached to each of the left-hand transverse shield plate 15*a* and the right-hand transverse shield plate 15*b*, a transverse screw shaft 161*b* that extends in the transverse direction while engaging the nut member 161, and a positioning motor 162*b* (162) that normally and reversely rotates the screw shaft 161*b*. The screw shaft 161*b* is normally and reversely rotated by driving the positioning motor 162*b*, whereby the nut member 161 moves to left and right along the transverse direction. Therefore, the left-hand transverse shield plate 15*a* and the right-hand transverse shield plate 15*b* are moved separately in the transverse direction. Based on the control of the main body controller 60, the shield plate transversely moving mechanism 16*b* adjusts the shielding amount in the transverse direction of the X-ray beam emitted from the X-ray generator 10*a* using the left-hand transverse shield plate 15*a* and the transverse shield plate 15*b*. The shield plate transversely moving mechanism 16*b* is an example of a transverse irradiation position controller that adjusts the irradiation range in the transverse direction of the X-ray beam to control the irradiation direction.

A regulating cylindrical body 152 is attached to each of the left-hand transverse shield plate 15*a* and the right-hand transverse shield plate 15*b*. A through-hole is made in the regulating cylindrical body 152 so as to pierce the regulating cylindrical body 152 along the transverse direction. A regulating shaft 153 extending in the longitudinal direction is fitted in the regulating cylindrical body 152, and the regulating shaft 153 regulates the transverse movement of the regulating cylindrical body 152. Therefore, the left-hand transverse shield plate 15*a* and the right-hand transverse shield plate 15*b* are moved in the transverse direction while not being inclined.

In the first preferred embodiment, the beam shaping mechanism 13 includes the longitudinal shield plate 14, the transverse shield plate 15, and the shield plate moving mechanism 16, and the beam shaping mechanism 13 is disposed in front of the outgoing port 12 of the X-ray generation unit 10. Therefore, the irradiation range of the X-ray generated by the X-ray generation unit 10 is regulated by the shielding to form the X-ray cone beam BX spread in to the truncated-pyramid shape toward the X-ray detection unit 20.

Particularly, the shield plate longitudinally moving mechanism 16*a* adjusts an interval between opposed edge portions 14*c* and 14*c* in the upper-side longitudinal shield plate 14*a* and the lower-side longitudinal shield plate 14*b*, and the shield plate transversely moving mechanism 16*b* adjusts an interval between opposed edge portions 15*c* and 15*c* in the left-hand transverse shield plate 15*a* and the right-hand transverse shield plate 15*b*. An opening 17, which has a quadrangular shape when viewed from the front side, is formed by the opposed edge portions 14*c* and 14*c* and the opposed edge portions 15*c* and 15*c* in order to form the X-ray cone beam BX having the desired shape.

For example, as illustrated in FIGS. 5A and 6A, the intervals between the opposed edge portions 14*c* and 14*c* is widely adjusted, and the intervals between the opposed edge portions 15*c* and 15*c* is widely adjusted, thereby obtaining a square large irradiation field opening 17*a*, which has the relatively large opening 17 when viewed from the front side. The X-ray transmitted through the large irradiation field opening 17*a* has a square shape in section and becomes the X-ray cone beam BX1 for large irradiation field CT spread into the square truncated-pyramid shape toward the X-ray detection unit 20.

On the other hand, as illustrated in FIGS. 5B and 6B, the intervals between the opposed edge portions 14*c* and 14*c* is narrowly adjusted, and the intervals between the opposed edge portions 15*c* and 15*c* is narrowly adjusted, thereby obtaining a square small irradiation field opening 17b, which has the relatively small opening 17 when viewed from the front side. The X-ray transmitted through the small irradiation field opening 17b has the square shape in section and becomes X-ray cone beam BX2 for small irradiation field CT spread into the square truncated-pyramid shape toward the X-ray detection unit 20.

As illustrated in FIG. 6C, the interval between the opposed edge portions 14c and 14c is widely adjusted, and the intervals between the opposed edge portions 15c and 15c is narrowly adjusted, thereby obtaining a rectangular panoramic photography opening 17c, which has the longitudinally long opening 17 when viewed from the front side. The section of the X-ray transmitted through the panoramic photography opening 17c becomes the X-ray slit beam BXP spread into the longitudinally long truncated-pyramid shape toward the X-ray detection unit 20.

In the beam shaping mechanism 13, the shield plate moving mechanism 16 moves the longitudinal shield plate 14 and transverse shield plate 15, each of which is constructed by the two plate members, and the opening 17 is formed in order to emit the desired X-ray cone beam BX. The beam shaping mechanism 13 is not limited to the configuration of the first preferred embodiment. For example, as illustrated in FIG. 7, L-shape shield plates 18 and 18 that have an L-shape when viewed from the front side may symmetrically be disposed about the center of the opening 17. In this case, the opening 17 is formed by edge portions 18a and 18a constituting interior angles of the L-shape shield plates 18 and 18.

For example, both the shield plate longitudinally moving mechanism 16a and the shield plate transversely moving mechanism 16b are provided to move the L-shape shield plates 18 in the longitudinal direction and the transverse direction, which allows the shape of the opening 17 to be adjusted.

For example, a longitudinally moving mechanism similar to the shield plate longitudinally moving mechanism 16a is provided on a base stage (not illustrated), which is displaced in the transverse direction by a transversely moving mechanism similar to the shield plate transversely moving mechanism 16b, and the L-shape shield plate 18 is displaced in the longitudinal direction by the longitudinally moving mechanism. Each L-shape shield plate 18 can be moved in the longitudinal direction or the transverse direction by the transversely moving mechanism, the base stage, and the longitudinally moving mechanism.

The X-ray detection unit 20 includes an X-ray detector 21 having a detection surface 21' for detecting the X-ray, and the X-ray cone beam BX is assuredly projected to the detection surface 21'.

In the X-ray CT photographic apparatus 1, as illustrated in FIG. 3, the beam shaping mechanism 13, the turning motor 37, the X-ray generation unit 10, and the X-ray detection unit 20 are connected to the main body controller 60. The beam shaping mechanism 13, the turning motor 37, the X-ray generation unit 10, and the X-ray detection unit 20 are driven according to a predetermined program, whereby the X-ray CT photography can be appropriately performed to the oval CT photographic region CAa set to the photographic object.

A situation in which the X-ray CT photographic apparatus 1 performs the X-ray CT photography to a right-hand dentition photographic object OB1 (a range surrounded by the CT photographic region line 213 in FIG. 8) of the subject M1 will be described below. Hereinafter, a range from an anterior tooth group T1 to a right-hand molar group T3 is referred to as the right-hand dentition photographic object OB1 in the dental arch of the upper jaw constructed by anterior-tooth-side teeth (the anterior tooth group T1) including the anterior tooth, left-hand-molar-side teeth (a left-hand molar group T2) including a left-hand molar, and right-hand-molar-side teeth (the right-hand molar group T3) including a right-hand molar. In order to perform the X-ray CT photography of the right-hand dentition photographic object OB1 in the upper jaw, it is assumed that the right-hand dentition photographic object OB1 is set to the oval CT photographic region CAa along the right-hand curved line in the dental arch region X when viewed from the axis direction of the turning shaft 31.

A lower jawbone having a head of lower jaw is illustrated in FIG. 8 and the like. However, even if the CT photographic region CA is set to the upper jaw, the position of the tooth can be easily understood as long as the shape of the lower jawbone is displayed. Therefore, the image of the lower jawbone may be used. Accordingly, only the dental arch image 211 illustrating the lower jawbone may be displayed on the image display unit 210. The dental arch image 211 illustrating the upper jawbone and the dental arch image 211 illustrating the lower jawbone may be displayed while being able to be switched. In the case that the CT photographic region CA is set to both the upper jaw and the lower jaw, the image of the lower jawbone may be used, or the image of the upper jaw and the image of the lower jaw may be switched. The dental arch image 211 is an example of the region assigning image of the subject M1.

Using the assigning cursor 212, the center in the longer direction of the oval CT photographic region CAa is assigned with respect to the dental arch image 211 displayed on the image display unit 210 of the CT photographic region setting screen 200. The slider 231b of the selection range setting unit 230 is slid to the right and left to set the number of teeth included in the oval CT photographic region CAa.

For example, in the case that the number of teeth assigned by the slide setting unit 231 is an odd number, a specific tooth that becomes the center in the longer direction is assigned as the center in the longer direction of the oval CT photographic region CAa by the assigning cursor 212.

For example, when teeth TH1, TH2, and TH3 (not illustrated) are arrayed in this order, the tooth TH2 is the center in the longer direction of the oval CT photographic region CAa, and the teeth TH1, TH2, and TH3 are set to the CT photographic target. In this case, the tooth TH2 is assigned by the assigning cursor 212, and the teeth TH1, TH2, and TH3 are assigned by the slide setting unit 231. Therefore, the oval CT photographic region CAa is set to the teeth TH1, TH2, and TH3.

A long diameter of the oval CT photographic region CAa is defined by the assignment manipulation, and a short diameter is automatically defined according to the assignment manipulation of the long diameter. At this point, a geometric calculation may be performed in each case, or the short diameter corresponding to the long diameter may be previously determined in a table. In either case, the oval shape of the oval CT photographic region CAa is determined such that the photographing can be performed by the photographic system including the X-ray generator 10a, the X-ray detector 21, and the beam shaping mechanism 13, and such that only the target tooth is set to the CT photographic target along the dental arch while the waste is minimized as much as possible.

In the case that the number of teeth assigned by the slide setting unit 231 is an even number, a spot between the two teeth located near the center in the longer direction is assigned as the center in the longer direction of the oval CT photographic region CAa by the assigning cursor 212.

For example, teeth TH1, TH2, TH3, TH4, and TH5 are arrayed in this order, and the teeth TH1 to TH4 are the interest region. In this case, the spot between the teeth TH2 and TH3 is assigned by the assigning cursor 212, and the teeth TH1 to TH4 are assigned by the slide setting unit 231. Therefore, the oval CT photographic region CAa is set so as to include the teeth TH1 to TH4.

It is not always necessary that the spot between the teeth TH2 and TH3 be assigned by the assigning cursor 212. For example, the tooth located near the center of the interest region may be assigned similarly to the case that the number of assigned teeth is the odd number. In this case, the oval CT photographic region CAa can arbitrarily be determined as the actual range.

For example, the tooth TH3 is defined as the center in the longer direction, and the four teeth are assigned by the slide setting unit 231. In this case, while a central portion of each of the teeth TH1 and TH5 becomes a boundary region, the oval CT photographic region CAa may be set so as to stride across a half region of the tooth TH1, the whole regions of the teeth TH2 to TH4, and a half region of the tooth TH5.

It is also conceivable that, by slightly adjusting the center position in the longer direction of the oval CT photographic region CAa, the oval CT photographic region CAa is set to the teeth TH1 to TH4 on the anterior tooth side, the oval CT photographic region CAa is set to the teeth TH2 to TH5 on the back tooth side, the oval CT photographic region CAa is set to all the teeth TH1 to TH5 by rounding up the number of teeth from 4 to 5, or the oval CT photographic region CAa is set to the teeth TH2 to TH4 by cutting down the number of teeth from 4 to 3.

The assignment information (positional information on the center in the longer direction of the oval CT photographic region CAa and information on the number of teeth included in the oval CT photographic region CAa) input on the CT photographic region setting screen 200 is transmitted to the information processing device 8. The information processing device 8 that receives the assignment information transmits the information on the oval CT photographic region line 213, which is previously set according to the center position and the number of teeth, to the manipulation display unit 61. The manipulation display unit 61 that receives the information on the CT photographic region line 213 displays the dental arch image 211 and the CT photographic region line 213 based on the received information on the image display unit 210 of the CT photographic region setting screen 200 while the dental arch image 211 and the CT photographic region line 213 overlap with each other.

The operator (for example, the practitioner) who checks the CT photographic region setting screen 200 checks if the CT photographic region line 213 is set to the desired position and range with respect to the dental arch image 211. At this point, when the set button 241 is pressed, the CT photographic region line 213 is fixed as the oval CT photographic region CAa and transmitted to the information processing device 8. When the start button 243 is pressed, as described later, the X-ray CT photographic apparatus 1 starts the X-ray CT photography of the right-hand dentition photographic object OB1 based on the fixed oval CT photographic region CAa.

On the other hand, when the reset button 242 is pressed, the assignment manipulation, performed through the image display unit 210, the upper-and-lower-jaw selection unit 220, and the selection range setting unit 230, is cancelled, and the screen returns to a pre-assignment default (initial state) screen. An undo button and a redo button and the like (not illustrated), which returns the screen to a preceding manipulation state or advances the screen to the subsequent manipulation state, may be prepared on the CT photographic region setting screen 200.

The X-ray CT photographic apparatus 1 performs the X-ray CT photography of the right-hand dentition photographic object OB1 such that, while the subject M1 is in the predetermined position of the X-ray CT photographic apparatus 1 (see FIG. 1), the turning arm 30 turns by at least 180 degrees with the turning shaft 31 as the turning center Sc from the initial position (the first turning position), in which the X-ray generation unit 10 is disposed on the side of the right-hand molar group T3 while the X-ray detection unit 20 is disposed on the side of the left-hand molar group T2 as illustrated in FIG. 9 (the X-ray regulating step S130).

The X-ray CT photography can be performed at the turning angle of only 180 degrees. However, preferably the projection data of the X-ray cone beam BX is obtained in each direction of at least 180 degrees with respect to each place in the CT photographic region.

Preferably, the X-ray CT photography is performed at a turning angle (=180 degrees+fan angle) in which a spread angle (a fan angle) of the X-ray cone beam BX is added to 180 degrees when viewed from the axis direction of the turning shaft 31. Image quality of the CT image can be improved by setting the turning angle to at least 360 degrees. Preferably, the X-ray CT photography is performed at the turning angle of 360 degrees in order that, while the image quality of the CT image is improved, a CT photographic time is shortened to reduce the X-ray exposure dose.

A range including slight increase and decrease in angle to an extent in which the actual difference is not generated from the viewpoint of image reconstruction is assumed in the turning angles (180 degrees, 180 degrees+fan angle, and 360 degrees).

The X-ray CT photographic apparatus 1 detects the detection signal for predetermined times with the X-ray detection unit 20 while rotating the turning arm 30 with the turning shaft 31 as the turning center Sc to turn the X-ray cone beam BX. More specifically, the main body controller 60 monitors the turning motor 37, and collects the detection signal acquired by the X-ray detector 21 as the projection data every time the turning arm 30 turning about the turning shaft 31 rotates by a predetermined angle.

The subject M1 may always be irradiated with the X-ray cone beam BX while the turning arm 30 turns, or the subject M1 may intermittently be irradiated with the X-ray cone beam BX in timing in which the X-ray detection unit 20 detects the X-ray. In the latter case, the subject M1 is intermittently irradiated with the X-ray, so that the X-ray exposure dose of the subject M1 can be reduced.

The collected projection data group is sequentially transmitted to the information processing device 8 and stored in the storage unit 802. The collected projection data group is processed by the calculation processor 801b, and reconstructed into three-dimensional data. The reconstruction calculation processing performed by the calculation processor 801b includes predetermined preprocessing, filter processing, and back projection processing. Various image processing technologies including a peripheral technology can be applied to these pieces of calculation processing.

FIG. 9 is a schematic plan view illustrating loci of the X-ray generator 10a, the transverse shield plate 15, and the X-ray detector 21 in the X-ray CT photography of the oval CT photographic region CAa. In FIG. 9, the X-ray generator 10a, the transverse shield plate 15, and the X-ray detector 21 are indicated by solid lines when located at a first turning position, and the X-ray generator 10a, the transverse shield plate 15, and the X-ray detector 21 are indicated by broken lines when located at second to fifth turning positions.

Figure 12B:
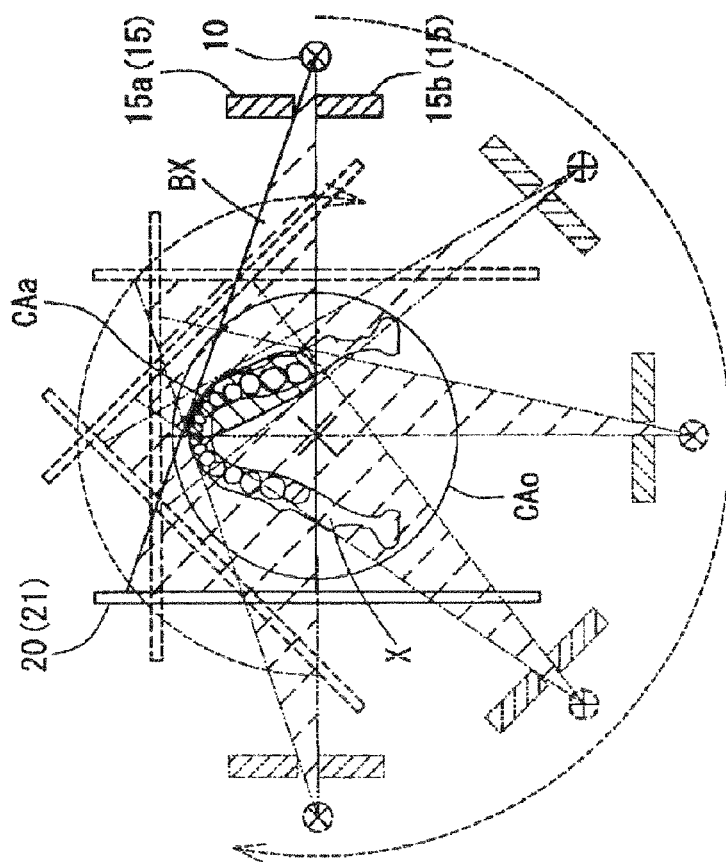
Figure 12A:
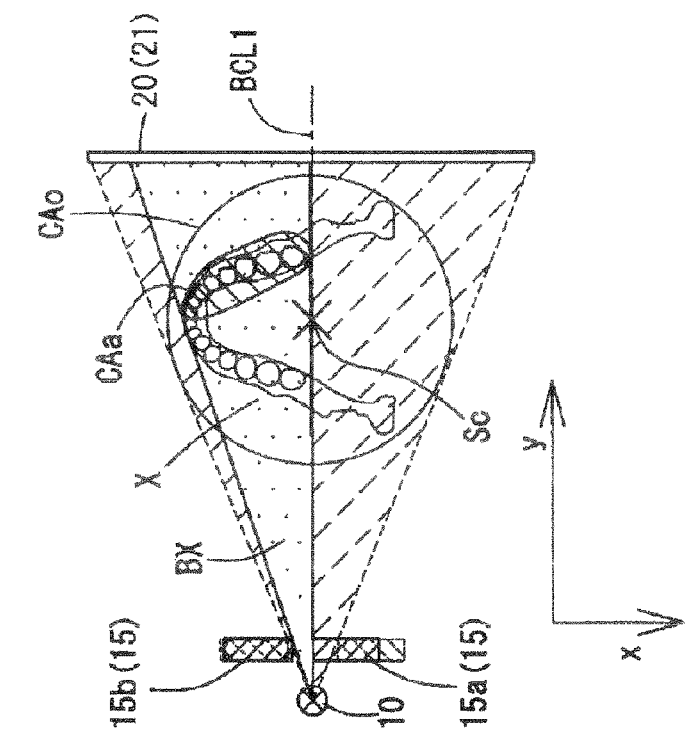

FIGS. 10 to 12 are schematic plan views illustrating the X-ray generator 10a, the transverse shield plate 15, and the X-ray detector 21 when the X-ray CT photography of the oval CT photographic region CAa is performed. More specifically, FIG. 10A is a schematic plan view of the X-ray generator 10a, the transverse shield plate 15, and the X-ray detector 21 when the turning arm 30 is located at the initial position (the first turning position). FIG. 10B is a schematic plan view of the X-ray generator 10a, the transverse shield plate 15, and the X-ray detector 21 when the turning arm 30 is located at the second turning position. FIG. 11A is a schematic plan view of the X-ray generator 10a, the transverse shield plate 15, and the X-ray detector 21 when the turning arm 30 is located at the third turning position. FIG. 11B is a schematic plan view of the X-ray generator 10a, the transverse shield plate 15, and the X-ray detector 21 when the turning arm 30 is located at the fourth turning position. FIG. 12A is a schematic plan view of the X-ray generator 10a, the transverse shield plate 15, and the X-ray detector 21 when the turning arm 30 is located at the fifth turning position. FIG. 12B is a schematic plan view illustrating a situation in which the turning arm 30 turns from the first turning position to the fifth turning position.

The turning positions of the turning arm 30 are illustrated at each predetermined angle in FIGS. 9 to 12 in order to easily describe a status of the X-ray CT photography. In other words, the turning arm 30 does not stop but continuously turns during the CT photography. The first turning position in FIG. 9A and the fifth turning position (the position where the turning arm 30 turns by 180 degrees from the first turning position) in FIG. 12A have a contrast relationship with respect to a contrast axis (not illustrated) passing through the turning center Sc.

At this point, it is assumed that the X-ray cone beam BX during the non-regulation is an X-ray cone beam BXV. It is also assumed that the columnar-shaped cylindrical CT photographic region CAo, which includes the whole dental arch region X and has the perfect-circle shape when viewed from the z-axis direction, is the CT photographic region of the conventional X-ray CT photography, and that the X-ray CT photography can be performed by irradiating the CT photographic region CAo with the X-ray cone beam BXV.

In the conventional X-ray CT photography, as illustrated in FIGS. 10A to 12A, during the CT photography, the whole CT photographic region CAo is always irradiated with the X-ray cone beam BXV about the turning center Sc. On the other hand, in the case that the X-ray CT photography is performed to the oval CT photographic region CAa, as illustrated in FIGS. 9 to 12, the irradiation range in the horizontal direction of the X-ray cone beam BX is narrowed according to the shape of the oval CT photographic region CAa so as to be narrower than the X-ray cone beam BXV.

As illustrated in FIGS. 9 to 12, in the turning arm 30 that turns about the turning center Sc from the first turning position, the center (the center of the X-ray cone beam BXV and a turning direction reference irradiation center line BCL1) of the X-ray cone beam BX emitted from the X-ray generation unit 10 along the y-axis direction always passes through the turning center Sc toward the X-ray detection unit 20. However, the oval CT photographic region CAa including the right-hand dentition photographic object OB1 is biased onto the +x side with respect to the turning center Sc in a certain turning angle range of the turning arm 30, and the oval CT photographic region CAa is biased onto the −x side with respect to the turning center Sc in another turning angle range of the turning arm 30. Therefore, the beam shaping mechanism 13 adjusts the irradiation range in the horizontal direction of the X-ray cone beam BX emitted from the X-ray generation unit 10.

In the case that the X-ray CT photography is performed to the oval CT photographic region CAa in FIG. 9A and the like, a bias amount with respect to the turning center Sc of the transverse end portion in the oval CT photographic region CAa changes with the advance of the turning of the turning arm 30 when viewed from the side of the X-ray generation unit 10. The beam shaping mechanism 13 adjusts the irradiation direction in the horizontal direction of the X-ray cone beam BX according to the change of the bias amount.

Sometimes a transverse width of the oval CT photographic region CAa including the right-hand dentition photographic object OB1 is narrowed with respect to the X-ray cone beam BX when the transverse spread is not regulated. Therefore, during the X-ray CT photography, the beam shaping mechanism 13 adjusts the transverse spread of the X-ray cone beam BX such that the transverse spread is narrowed according to the width of the oval CT photographic region CAa.

Specifically, the shield plate transversely moving mechanism 16b adjusts the transverse position of the transverse shield plate 15 (the left-hand transverse shield plate 15a and the right-hand transverse shield plate 15b) with respect to the outgoing port 12 according to the turning angle, whereby the transverse spread of the X-ray cone beam BX is narrowed according to the width of the oval CT photographic region CAa. The center of the opening 17 is biased onto the −x side or the +x side with respect to the outgoing port 12, whereby the irradiation direction of the X-ray cone beam BX is adjusted according to the oval CT photographic region CAa. Therefore, in FIGS. 10A, 10B, 11A, 11B, and 12A, the X-ray irradiation is regulated in the portion hatched by diagonal lines, so that the X-ray exposure dose of the subject M1 can be reduced.

More particularly, as illustrated in FIG. 10A, in the case that the turning arm 30 is located in the first turning position where the oval CT photographic region CAa is irradiated with the X-ray cone beam BX in the direction substantially orthogonal to the longer direction of the oval CT photographic region CAa, the left-hand transverse shield plate 15a is slightly displaced onto the −x side and the right-hand transverse shield plate 15b is largely displaced onto the +x side. Therefore, the width of the opening 17 is formed into about a half of the large irradiation field opening 17a in FIG. 6A. As a result, the irradiation direction of the X-ray cone beam BX is biased onto the +x side to an extent in which the boundary line on the −x side of the X-ray cone beam BX is matched with the turning direction reference irradiation center line BCL1. The X-ray cone beam BX is emitted such that the boundary line of the X-ray cone beam BX comes into contact with the oval CT photographic region CAa.

In the case of the conventional X-ray CT photography in which the X-ray is not regulated, the X-ray CT photography is performed to a circular CT photographic region CAo including the whole dental arch region X. Compared with the X-ray CT photography of the first preferred embodiment with the conventional X-ray CT photography, the X-ray exposure dose of the subject M1 can be reduced in the region (the outside of the oval CT photographic region CAa) indicated by the oblique hatching in FIG. 10A.

In the case that the turning arm 30 is located in the second turning position in FIG. 10B, the irradiation direction of the X-ray cone beam BX becomes substantially parallel to the longer direction of the oval CT photographic region CAa. At this point, the left-hand transverse shield plate 15a is displaced onto the −x side from the state in FIG. 10A, and the right-hand transverse shield plate 15b is further disposed onto the +x side. Therefore, the opening 17 in FIG. 10A is further narrowed to about a half width. The irradiation direction of the X-ray cone beam BX is further biased onto the +x side from the turning direction reference irradiation center line BCL1. The X-ray cone beam BX is emitted such that the boundary line of the X-ray cone beam BX comes into contact with the oval CT photographic region CAa. Accordingly, the irradiation range of the X-ray is further regulated compared with the state in FIG. 10A, so that the X-ray exposure dose of the subject M1 can be reduced.

In the case that the turning arm 30 is located in the third turning position in FIG. 11A, the irradiation direction of the X-ray cone beam BX substantially intersects the longer direction of the oval CT photographic region CAa. At this point, although the left-hand transverse shield plate 15a is further displaced onto the −x side from the state in FIG. 10B, the right-hand transverse shield plate 15b is returned to the position in FIG. 10A. Therefore, the width of the opening 17 is narrowed to about two-thirds of the state in FIG. 10A. Because the irradiation direction is returned onto the −x side compared with the irradiation direction of the X-ray cone beam BX in FIG. 10B, the irradiation direction of the X-ray cone beam BX is biased to the extent in which the boundary line on the −x side of the X-ray cone beam BX is matched with the turning direction reference irradiation center line BCL1 similarly to FIG. 10A. The X-ray cone beam BX is emitted such that the boundary line of the X-ray cone beam BX comes into contact with the oval CT photographic region CAa.

In the state in FIG. 11A, the range where the subject M1 is irradiated with the X-ray increases compared with the state in FIG. 10B. However, the X-ray exposure dose can be increased to the minimum necessity.

In the case that the turning arm 30 is located in the fourth turning position in FIG. 11B, an intersection angle of the irradiation direction of the X-ray cone beam BX and the longer direction of the oval CT photographic region CAa is larger than the third turning position. At this point, the left-hand transverse shield plate 15a and the right-hand transverse shield plate 15b are moved onto the −x side from the state in FIG. 11A to form the opening 17 having the width similar to that of the state in FIG. 10A. The X-ray cone beam BX is emitted such that the boundary line of the X-ray cone beam BX comes into contact with the oval CT photographic region CAa. Therefore, the X-ray exposure dose of the subject M1 outside the oval CT photographic region CAa can be reduced to the state similar to the initial state in FIG. 10A.

As described above, the fifth turning position in FIG. 12A has the contrast relationship with the first turning position with the straight line (not illustrated) passing through the turning center Sc as the contrast axis. For this reason, the opening 17 similar to that of the state in FIG. 10A is formed in the case that the turning arm 30 is located in the fifth turning position. Compared with the state in FIG. 11B, the irradiation direction of the X-ray cone beam BX is biased onto the −x side. The X-ray cone beam BX is emitted such that the boundary line of the X-ray cone beam BX comes into contact with the oval CT photographic region CAa. Accordingly, the X-ray exposure dose of the subject M1 outside the oval CT photographic region CAa can be reduced to the extent similar to that of the initial state in FIG. 10A.

As described above, the position of the oval CT photographic region CAa changes according to the turning position (the turning angle) of the turning arm 30 with respect to the turning direction reference irradiation center line BCL1 of the X-ray cone beam BX emitted from the X-ray generation unit 10 toward the X-ray detection unit 20. In other words, the shield plate transversely moving mechanism 16b adjusts the transverse positions of the left-hand transverse shield plate 15a and right-hand transverse shield plate 15b with respect to the outgoing port 12 according to the turning angle of the turning arm 30. With respect to the outgoing port 12, the opening 17 is properly biased onto the +x side or the −x side in the direction from the X-ray generation unit 10 toward the X-ray detection unit 20. Therefore, the irradiation range and irradiation direction of the X-ray cone beam BX are adjusted according to the oval CT photographic region CAa set by the operator. Thus change of the irradiation range of X-ray cone beam BX to the x-axis direction is controlled during said X-ray CT photography so that only the set CT photographic region is irradiated with the X-ray cone beam BX about x-axis direction.

It is easily understood that the X-ray exposure dose of the oval CT photographic region CAa is extremely low compared with the case that the perfect-circle CT photographic region is set to the whole region of the right-hand dentition photographic object OB1.

As described above, the X-ray CT photography may be performed at the turning angle (=180 degrees+fan angle) in which the spread angle (the fan angle) of the X-ray cone beam BX is added to 180 degrees when viewed from the axis direction of the turning shaft 31. The specific configuration will be described below.

FIG. 9 illustrates an example in which the CT photography is performed by turning the turning arm by 180 degrees from the first turning position to the fifth turning position. The projection data of 180 degrees or more can be obtained at any point in the oval CT photographic region CAa by slightly widening the turning range from 180 degrees.

At this point, the spread of the X-ray cone beam BX becomes the fan shape, when viewed from the z-axis direction, and the X-ray cone beam BX has a portion constituting a side on the +x side and a portion constituting a side on the −x side. Because the X-ray cone beam BX in FIG. 9 has the truncated-pyramid shape, the portion constituting the side on the +x side and the portion constituting the side on the −x side form a plane. Hereinafter, the portion constituting the side on the +x side (a left-hand side surface when the X-ray generator 10a is viewed from the front side) is referred to as a +x end, and the portion constituting the side on the −x side (a right-hand side surface when the X-ray generator 10a is viewed from the front side) is referred to as a −x end.

The example in FIG. 9 is deformed, the turning of the turning arm 30 is started from the first turning position, and the turning of the turning arm 30 is further continued beyond the fifth turning position while the X-ray irradiation is performed. The X-ray irradiation of the oval CT photographic region CAa is ended after the turning arm 30 is turned to the position in which the −x end of the X-ray cone beam BX overlaps with the +x end of the X-ray cone beam BX in the first turning position. Therefore, the projection data of 180 degrees or more can be obtained at any point in the oval CT photographic region CAa.

More preferably, when the turning of the turning arm 30 progresses to come close to the ending position of the X-ray irradiation of the oval CT photographic region CAa, the −x end of the X-ray cone beam BX and the +x end of the X-ray cone beam BX in the first turning position overlap with each other. The point where the projection data of 180 degrees is obtained in the oval CT photographic region CAa is generated from this time point. Accordingly, the right-hand transverse shield plate 15b is displaced from this time point so as to come close to the left-hand transverse shield plate 15a with the progress of the turning of the turning arm 30, and the point where the projection data of 180 degrees is obtained may not be irradiated with the X-ray. Thus, the projection data of just 180 degrees can be obtained at any point in the oval CT photographic region CAa, and the X-ray exposure dose of the subject M1 can be reduced as much as possible while the good projection data suitable to the reconstruction is obtained. At this point, the read region of the detection surface 21' of the X-ray detector 21 can be reduced according to the X-ray shielding amount of the right-hand transverse shield plate 15b.

The control that obtains the projection data of just 180 degrees may be performed at the stage at which the turning of the turning arm 30 is ended as described above or the stage at which the turning of the turning arm 30 is started. In this case, for example, with the progress of the turning of the turning arm 30, the right-hand transverse shield plate 15b may be separated from the left-hand transverse shield plate 15a. The X-ray beam may be regulated at both the stage at which the turning of the turning arm 30 is started and the stage at which the turning of the turning arm 30 is ended.

The longitudinal spread of the X-ray cone beam BX is also regulated according to the oval CT photographic region CAa. For example, in the case that the oval CT photographic region CAa is set to the tooth of the upper jaw, the oval CT photographic region CAa is irradiated with the X-ray cone beam BX such that upper and lower portions of the X-ray cone beam BX come into contact with the oval CT photographic region CAa including the tooth of the upper jaw during the X-ray CT photography.

FIG. 13 is an explanatory view of the X-ray cone beam BX in which the irradiation range is regulated with respect to the longitudinal direction. FIG. 13 is a view in which the X-ray generator 10a, the X-ray cone beam BX, and the X-ray detection unit 20 (specifically, the X-ray detector 21) are viewed from the −x-direction toward the +x-direction. In FIG. 13, the X-ray CT photography target such as the tooth of the upper jaw exists on the upper-side (the +z side) with respect to the X-ray generation unit 10.

In FIG. 13, the oval CT photographic region CAa including the right-hand dentition photographic object OB1 is biased in the longitudinal direction with respect to the center line (a vertical direction reference irradiation center line BCL2) of the X-ray cone beam BX that is horizontally emitted from the X-ray generation unit 10 toward the X-ray detection unit 20 during non-regulation. Therefore, the beam shaping mechanism 13 adjusts the irradiation range in the vertical direction of the X-ray cone beam BX emitted from the X-ray generation unit 10, thereby adjusting the irradiation direction of the X-ray cone beam BX.

In FIG. 13, the vertical direction reference irradiation center line BCL2 is substantially perpendicularly incident to the X-ray detector 21. Alternatively, the X-ray detector 21 may be disposed at a level lower than that of the X-ray generator 10a. In this case, in the case that the X-ray detector 21 is disposed at a level relatively higher than that of the X-ray generator 10a like the panoramic photography, the irradiation direction of the X-ray cone beam BX is emitted upward with respect to the horizontal plane.

As illustrated in FIG. 13, the height in the longitudinal direction of the oval CT photographic region CAa including the right-hand dentition photographic object OB1 is less than a width of the X-ray cone beam BX in which the longitudinal spread is not regulated. Therefore, the beam shaping mechanism 13 adjusts the longitudinal spread of the X-ray cone beam BX such that the longitudinal spread is narrowed according to the height of the oval CT photographic region CAa.

Particularly, the shield plate longitudinally moving mechanism 16a adjusts the longitudinal positions of the upper-side longitudinal shield plate 14a and lower-side longitudinal shield plate 14b the with respect to the outgoing port 12. Therefore, the opening 17 is biased onto the +z side with respect to the outgoing port 12, and as a result, the irradiation range in the longitudinal direction of the X-ray cone beam BX is narrowed according to the oval CT photographic region CAa to change the irradiation direction.

As illustrated in FIG. 13B, the position of the oval CT photographic region CAa with respect to the vertical direction reference irradiation center line BCL2 changes relatively according to the turning position (the turning angle) of the turning arm 30. More specifically, according to the turning position of the turning arm 30, the longitudinal positions of the upper-side longitudinal shield plate 14a and lower-side longitudinal shield plate 14b are adjusted with respect to the outgoing port 12. Therefore, the opening 17 is biased onto the +z side with respect to the outgoing port 12, and as a result, the irradiation direction of the X-ray cone beam BX is changed upward according to the oval CT photographic region CAa.

In FIG. 13B, the position at the upper right corner position of the oval CT photographic region CAa is located on the side closer to the turning center Sc than the oval CT photographic region CAa in FIG. 13A. For this reason, the level at an upper end of the X-ray cone beam BX is lowered onto the lower side (the −z side). Similarly, the level at a lower end of the X-ray cone beam BX is lowered onto the lower side.

As described above, the irradiation range in the longitudinal direction of the X-ray cone beam BX is adjusted according to the width in the height direction of the oval CT photographic region CAa, which allows the X-ray exposure dose of the subject M1 to be reduced outside the oval CT photographic region CAa.

Alternatively, an elevation angle (or a depression angle) in the irradiation direction of the X-ray cone beam BX may be changed with respect to the horizontal plane by changing the positions of the upper-side longitudinal shield plate 14a and lower-side longitudinal shield plate 14b according to the turning position (the turning angle) of the turning arm 30. In this case, the irradiation range of the X-ray cone beam BX is changed in the z-axis direction during the X-ray CT photography.

In the first preferred embodiment, in order to set the oval CT photographic region CAa, the neighborhood of the center of the oval CT photographic region CAa is assigned on the image display unit 210 by the assigning cursor 212, and the number of teeth including the oval CT photographic region CAa is assigned using the selection range setting unit 230. However, the method for assigning the CT photographic region CA is not limited to the first preferred embodiment. Other methods for setting the CT photographic region CA will be described below with reference to FIGS. 14 to 17.

FIG. 14 is a view illustrating another CT photographic region setting screen 200A. Like the CT photographic region setting screen 200 in FIG. 8, the CT photographic region setting screen 200A includes an image display unit 210A, the upper-and-lower-jaw selection unit 220, and the condition setting unit 240. However, the selection range setting unit 230 is eliminated in the CT photographic region setting screen 200A. The functions of the upper-and-lower-jaw selection unit 220 and condition setting unit 240 in the CT photographic region setting screen 200A are similar to those of the upper-and-lower-jaw selection unit 220 and condition setting unit 240 in the CT photographic region setting screen 200.

Like the image display unit 210 in the CT photographic region setting screen 200, the dental arch image 211 and the assigning cursor 212 are displayed on the image display unit 210A. In the CT photographic region setting screen 200 in FIG. 8, the neighborhood of the center in the longer direction of the oval CT photographic region CAa is assigned by the assigning cursor 212 in order to set the CT photographic region line 213. On the other hand, in the CT photographic region setting screen 200A in FIG. 14, two points (a starting point and an ending point) that are of both end portions in the longer direction of the oval CT photographic region CAa are assigned by the assigning cursor 212. One of the starting point and the ending point corresponds to one end, and the other corresponds to the other end.

FIG. 14 illustrates the two assigning cursors 212 for the sake of convenience. However, actually the assigning cursor 212 is moved to assign the tooth of the ending point after the tooth of the starting point is assigned by the assigning cursor 212. Alternatively, after the tooth of the starting point is assigned, the assigning cursor 212 is fixed to the starting point, and the tooth of the ending point may be assigned by the newly emerging assigning cursor 212.

The position of the starting point or ending point may be changed in the case that the assignment is mistakenly performed. The oval CT photographic region CAa may be assigned in units of teeth such as the tooth of the starting point and the tooth of the ending point. Alternatively, a certain range is displayed as the CT photographic region line 213 at an initial stage, both end portions in the longer direction of the CT photographic region line 213 are selected by the assigning cursor 212, and the CT photographic region line 213 may be deformed or moved by a drag manipulation to change the range of the CT photographic region line 213.

The input assignment information (the information on the teeth of the starting point and ending point assigned by the assigning cursor 212) is transmitted to the information processing device 8. The information processing device 8 that receives the assignment information transmits the information on the oval CT photographic region line 213 to the manipulation display unit 61 according to a combination of the tooth of the starting point and the tooth of the ending point. The 16 teeth are arrayed in total in the dental arch region X, 120 ways are conceivable as the combination of 2 teeth selected from the 16 teeth. Accordingly, the 120-way oval CT photographic region line 213 is previously set, which allows the information processing device 8 to deal with any combination of 2 teeth.

The only single tooth (the vertically arrayed two teeth in the case that both the upper jaw and the lower jaw are included in the CT photographic region CA) may be set as the oval CT photographic region CAa. In this case, the total of 136 ways of the CT photographic region lines 213 may be previously registered.

In the case that the only single tooth becomes the photographic target, for example, the CT photographic region line 213 may be set to a substantially perfect circle in which the lengths in the longer direction and shorter direction are substantially equal to each other.

Alternatively, a wisdom tooth may not be selected by the assigning cursor 212 because only the place that frequently becomes an implant placement target is set to the X-ray CT photography target. Irrespective of the number of teeth, the range simply surrounded by the CT photographic region line 213 may be directly set to the oval CT photographic region CAa.

At least one of the regions of the jawbone may become the CT photographic region. Only the tooth does not become the CT photography target, but the jaw joint may be included in the CT photographic region. In this case, the CT photography can be performed to only the jaw joint or the region including the jaw joint and another tooth.

The manipulation display unit 61 that receives the information on the CT photographic region line 213 from the information processing device 8 displays the dental arch image 211 and the CT photographic region line 213 on the image display unit 210A while the dental arch image 211 and the CT photographic region line 213 overlap with each other. Because the processing flow after the overlapping display is similar to that in FIG. 8, the description is omitted.

FIG. 15 is a view illustrating another CT photographic region setting screen 200B. Like the CT photographic region setting screen 200A in FIG. 14, the CT photographic region setting screen 200B includes an image display unit 210B, the upper-and-lower-jaw selection unit 220, and the condition setting unit 240. The functions of the upper-and-lower-jaw selection unit 220 and condition setting unit 240 in the CT photographic region setting screen 200B are similar to those of the upper-and-lower-jaw selection unit 220 and condition setting unit 240 in the CT photographic region setting screen 200.

Like the image display unit 210 of the CT photographic region setting screen 200, the dental arch image 211 and the assigning cursor 212 are displayed on the image display unit 210B. Additionally, in the CT photographic region setting screen 200B, plural (in this case, five) divided areas 214 into which the dental arch region X is divided are displayed while overlapping with the dental arch image 211 on the image display unit 210B. In the CT photographic region setting screen 200B, the specific divided area 214 is assigned from the plural divided areas 214 through the assigning cursor 212.

For example, in the case that the right-hand dentition photographic object OB1 becomes the target region of the X-ray CT photography, the divided area 214 including the right-hand dentition photographic object OB1 is assigned on the image display unit 210B by the assigning cursor 212. The input assignment information (the information indicating the specific divided area 214) is transmitted to the information processing device 8. The information processing device 8 that receives the assignment information transmits the information on the previously-set oval CT photographic region CAa corresponding to the divided area 214 to the main body 2 of the X-ray CT photographic apparatus 1. The main body 2 performs the X-ray CT photography of the oval CT photographic region CAa.

In the CT photographic region setting screen 200B in FIG. 15, the total of five divided areas 214, namely, a portion mainly including the anterior tooth group T1, a portion mainly including the left-hand molar group T2, a portion mainly including the right-hand molar group T3, and right and left jaw point portions are set with respect to the dental arch image 211. However, the dividing pattern of the divided areas 214 is not limited to the example of FIG. 15. Various dividing patterns are previously stored, and the specific dividing pattern may be called in response to the manipulation of a switching button (not illustrated) used to switch the dividing pattern.

The boundary line of the divided area 214 is selected by the assigning cursor 212, and the boundary line may be deformed or moved by the drag manipulation and the like to deform or move the divided area 214. The X-ray CT photography processing flow after the selection and assignment of the divided area 214 is substantially similar to that of the processing flow after the setting of the CT photographic region line 213 in the image display unit 210 of FIG. 8.

FIG. 16 is a view illustrating another CT photographic region setting screen 200C. Like the CT photographic region setting screen 200A in FIG. 14, the CT photographic region setting screen 200C includes an image display unit 210C, the upper-and-lower-jaw selection unit 220, and the condition setting unit 240. The functions of the upper-and-lower-jaw selection unit 220 and condition setting unit 240 in the CT photographic region setting screen 200C are similar to those of the upper-and-lower-jaw selection unit 220 and condition setting unit 240 in the CT photographic region setting screen 200 of FIG. 8.

The dental arch image 211 is displayed on the image display unit 210C. In the CT photographic region setting screen 200, the neighborhood of the center in the longer direction of the CT photographic region CA is assigned by the assigning cursor 212 in order to set the CT photographic region line 213. On the other hand, in the CT photographic region setting screen 200C, an oval closed curve (a handwritten CT photographic region line 213C) including the interest region (for example, the right-hand dentition photographic object OB1) is drawn with a drawing pen 250, thereby assigning the oval CT photographic region CAa.

The information (the assignment information) indicating the position and size of the handwritten CT photographic region line 213C, which is drawn and input on the image display unit 210C through the drawing pen 250, is transmitted to the information processing device 8. The information processing device 8 that receives the assignment information transmits the information on the oval CT photographic region CAa, which is close to the handwritten CT photographic region line 213C in the previously-prepared oval CT photographic regions CAa, to the main body 2 of the X-ray CT photographic apparatus 1. The main body 2 performs the X-ray CT photography based on the information on the received oval CT photographic region CAa.

In the previously-prepared oval CT photographic region CAa, not only the information on the oval CT photographic region CAa close to the handwritten CT photographic region line 213C may be selected, but also the handwritten CT photographic region line 213C may directly become the CT photographic region. In this case, line shifting caused by the hand writing can be automatically corrected to some extent.

Because the CT photographic region CA becomes a closed region defined by the curved line that is convex toward the outside of the diameter, the oval CT photographic region CAa formed only by the curved line, which is close to the handwritten CT photographic region line 213C and is convex toward the outside of the diameter, is selected even if a portion that is concave toward the inside of the diameter is partially included in the handwritten CT photographic region line 213C. The portion that is concave toward the inside of the diameter in the handwritten CT photographic region line 213C may be automatically corrected so as to become the portion that is convex toward the outside of the diameter.

Figure 17:
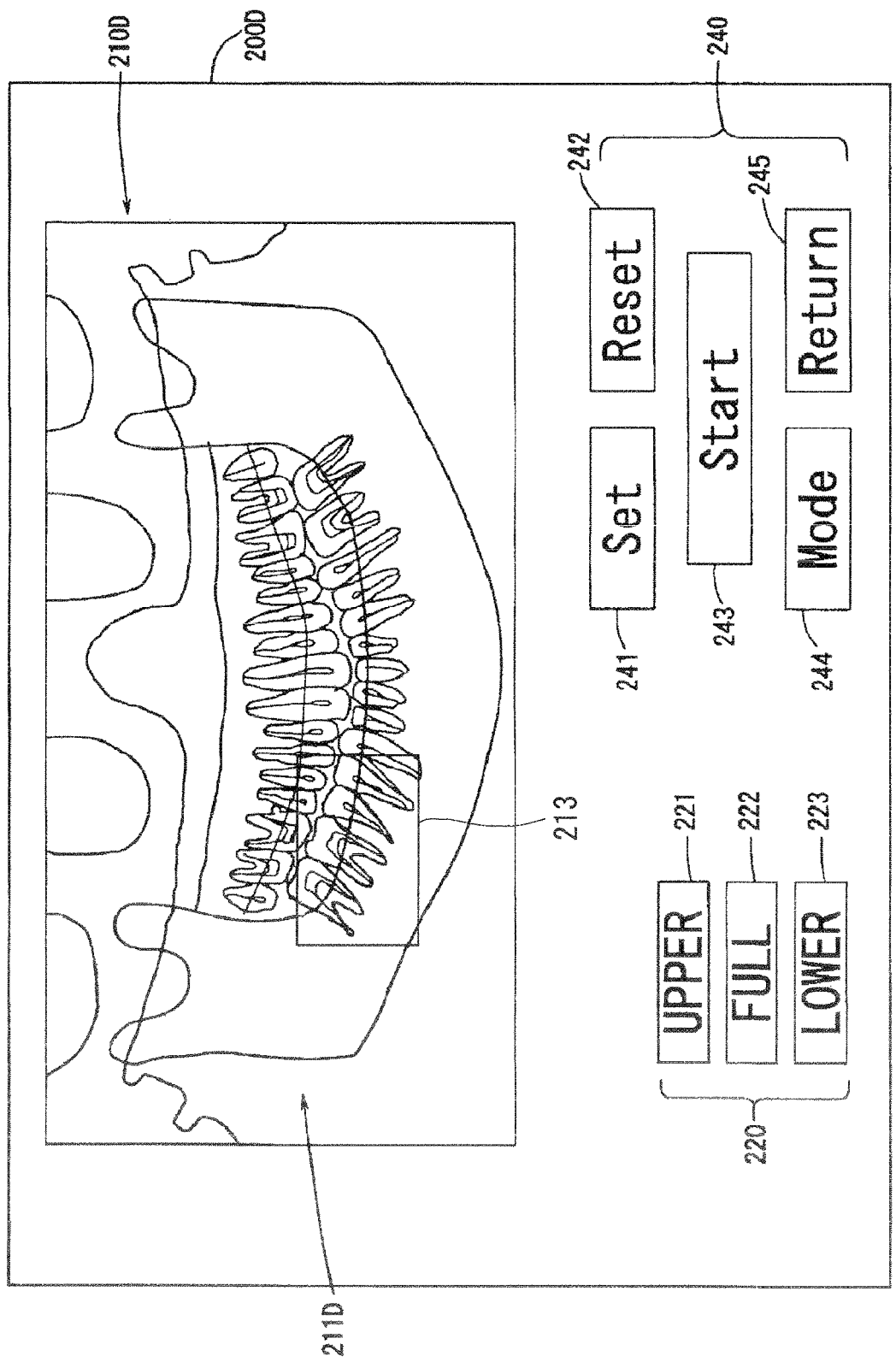

FIG. 17 is a view illustrating another CT photographic region setting screen 200D. Like the CT photographic region setting screen 200A in FIG. 14, the CT photographic region setting screen 200D includes an image display unit 210D, the upper-and-lower-jaw selection unit 220, and the condition setting unit 240. The functions of the upper-and-lower-jaw selection unit 220 and condition setting unit 240 in the CT photographic region setting screen 200D are similar to those of the upper-and-lower-jaw selection unit 220 and condition setting unit 240 in the CT photographic region setting screen 200 of FIG. 14. One of the feature points of the CT photographic region setting screen 200D in FIG. 17 is that the image (a panoramic image 211D) is displayed when the dental arch is viewed from the y-axis direction.

The panoramic image 211D, in which the panoramic photography is previously performed to the dental arch region X of the subject M1 using the X-ray, is displayed on the image display unit 210D instead of the dental arch image 211. In the image display unit 210D, the CT photographic region CA is set on the panoramic image 211D. In FIG. 17, the CT photographic region line 213 is set first. Although not illustrated, the CT photographic region line 213 is assigned using the assigning cursor 212 or the drawing pen 250.

The assignment information, which is input with respect to the panoramic image 211D on the image display unit 210D in order to assign the oval CT photographic region CAa, is transmitted to the information processing device 8. The information processing device 8 transmits the information on the CT photographic region line 213 corresponding to the received assignment information to the manipulation display unit 61.

The manipulation display unit 61 that receives the information on the CT photographic region line 213 displays the panoramic image 211D and the CT photographic region line 213 based on the received information on the image display unit 210D of the CT photographic region setting screen 200D while the panoramic image 211D and the CT photographic region line 213 overlap with each other. The processing flow after the overlapping display is similar to that of the CT photographic region setting screen 200.

The three-dimensional positional information on the panoramic tomographic position of the subject M1 fixed to the subject fixing unit 421 can easily be specified by the calculation processing of the calculation processor 801b from the positional relationship between the subject fixing unit 421 and the set panoramic tomographic position. Accordingly, the three-dimensional coordinate of the position assigned on the panoramic image 211D is acquired by the calculation.

The panoramic image 211D is not limited to the panoramic image acquired by the X-ray CT photographic apparatus 1, and the panoramic image 211D may be a panoramic image acquired by another photographic apparatus. In this case, the three-dimensional coordinate of the position assigned on the panoramic image 211D can be acquired by the calculation as long as the positional information on the panoramic tomography is already known in performing the panoramic photography. The panoramic image 211D is not necessarily the photographed image that is acquired by performing the panoramic photography of the subject M1. For example, a panoramic tomographic image of the jaw of a standard skeleton or an illustration of the photographed panoramic image may be used as the panoramic image 211D.

The CT photographic region CA (the oval CT photographic region CAa) corresponding to the interest region can be properly set using the CT photographic region setting screens 200, 200A, 200B, 200C, and 200D. The target object except the right-hand dentition photographic object OB1 may be naturally set to the CT photographic region CA.

FIG. 18 is a schematic plan view illustrating loci of the X-ray generation unit 10, the transverse shield plate 15, and the X-ray detection unit 20 when the X-ray CT photography of the elliptical CT photographic region CAb including the photographic object OB is performed. In FIG. 18, the plural teeth of the anterior tooth group T1 are set to the photographic object OB, and the small irradiation field X-ray CT photography is performed to the elliptical CT photographic region CAb that is smaller than the oval CT photographic region CAa. As illustrated in FIG. 18, the left-hand transverse shield plate 15a and the right-hand transverse shield plate 15b are moved in the transverse direction according to the elliptical CT photographic region CAb, thereby adjusting the irradiation range of the X-ray cone beam BX. Therefore, the X-ray exposure dose of the subject M1 is reduced outside the elliptical CT photographic region CAb.

FIG. 19 is a view illustrating a CT photographic region CA having another shape. The CT photographic region CA in FIG. 19A is an oval CT photographic region CAa1 that includes the right side of the anterior tooth group T1, the right-hand molar group T3, and a position Kh near the right end of a jawbone K in the dental arch region X. The CT photographic region CA in FIG. 19B is an oval CT photographic region CAa2 that includes the oval CT photographic region CAa1 and part of the left-hand molar group T2.

The CT photographic region CA in FIG. 19C is a substantially triangular CT photographic region CAc that surrounds the whole dental arch region X including the positions Kh near the right and left ends of the jawbone and the anterior tooth group T1. Particularly, in the substantially triangular CT photographic region CAc, three corner portions are formed into arc shapes, and a side connecting the corner portions is formed into the arc shape that is convex outward. In the substantially triangular CT photographic region CAc, the arc portion along the dentition of the anterior tooth group T1 is set to the vertex portion, and a curvature of an arc base portion, which connects the positions Kh near the right and left ends of the jawbone when viewed from above, is larger than a curvature of a side portion connecting the base portion and the vertex portion. In other words, the shape of the substantially triangular CT photographic region CAc is a substantial Reuleaux triangular shape in which three vertices of what is called a Reuleaux triangle are connected by the arcs that are convex outward. The shape of the CT photographic region CA can be set as a substantially semicircular shape not illustrated which connects an outer periphery of the dental arch region while a vertex portion is located near an anterior tooth. The condition that to connect an outer periphery of the dental arch region while a vertex portion is located near an anterior tooth can be applied to the substantially triangular CT photographic region CAc.

Figure 23:
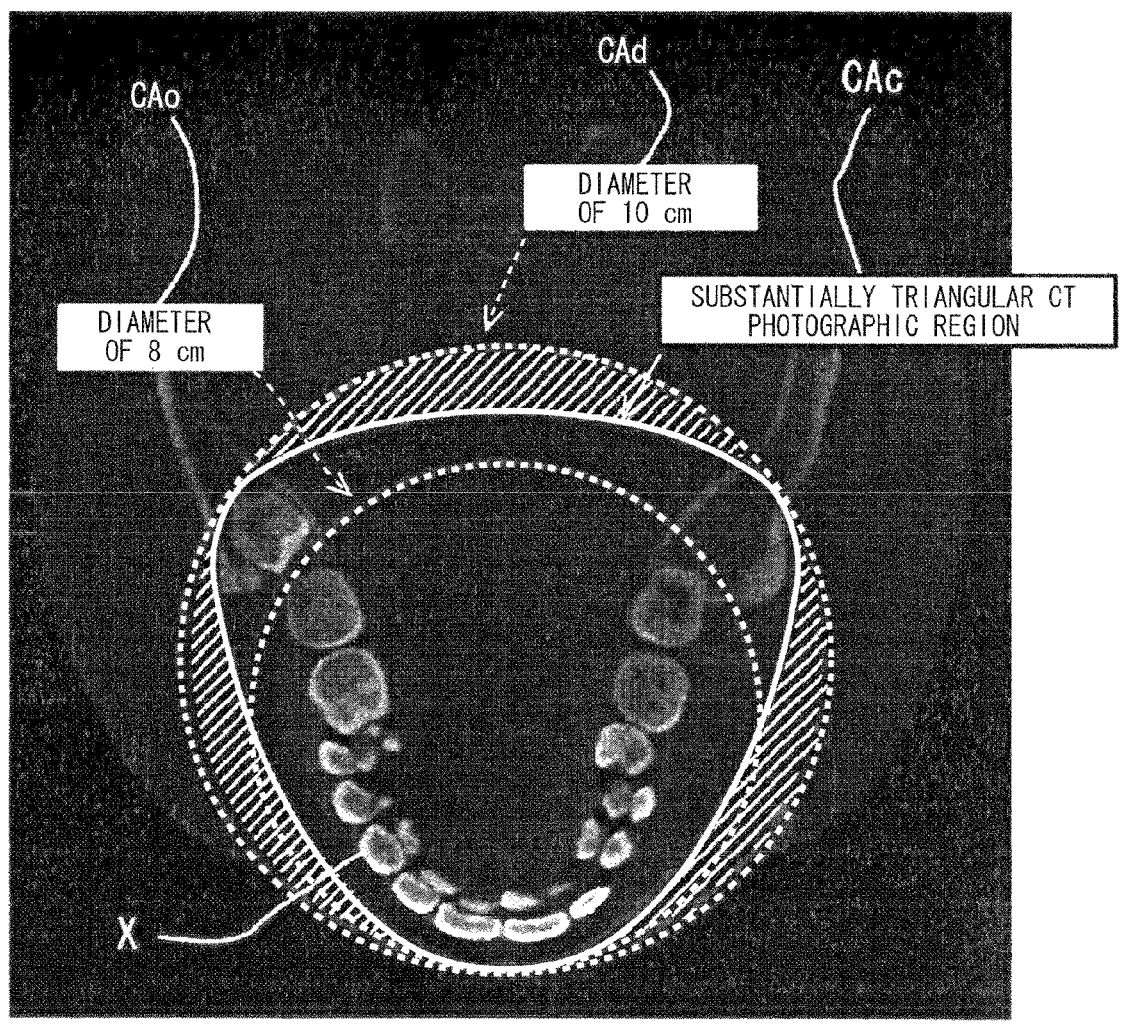
FIG. 23 is a plan view illustrating various CT photographic regions CA.

As shown in FIGS. 23 and 24, in the conventional X-ray CT photography, the CT photographic region CA is formed into the circular CT photographic region CAo, where the CT photographic region is the perfect circle, in order to perform the X-ray CT photography of the whole dental arch region X. In order to perform the CT photography of the wide region including all the tooth arrangement and the jaw joint, it is necessary to set the large perfect-circle CT photographic region CAj. The jaw joint is out of the region in the CT photographic region CAo, and the X-ray exposure dose is increased in the perfect-circle CT photographic region CAj. On the other hand, in the case of the substantially triangular CT photography region CAc, the CT photographic region CA can be approximated to the form of the dental arch region X. Therefore, the X-ray exposure dose of the subject M1 can be reduced outside the dental arch region X while the CT photography is performed to the wide region of the target jawbone.

The CT photographic region CA in FIG. 19D is a substantially triangular CT photographic region CAc1 in which the substantially triangular CT photographic region CAc is contracted such that only the tooth is included. The shape of the whole dental arch region X including the right and left ends of the jawbone is similar to the shape of the region of only the teeth portion in the dental arch region X. For this reason, the X-ray CT photographic apparatus 1 can perform the X-ray CT photography while the substantially triangular CT photographic region CAc is contracted to the whole dental arch region X or the region including all the teeth.

It is clear that, compared with the perfect-circular CT photographic region CAo in FIG. 23, the substantially triangular CT photographic region CAc1 is maintained in a requisite minimum range while the comparable tooth arrangement region falls within the CT photographic region.

The CT photographic region CA in FIG. 19E is a substantially triangular CT photographic region CAc2 having a reverse triangular shape when viewed from above in which the curved line along the arrangement of the anterior tooth group T1 becomes the base portion. The substantially triangular CT photographic region CAc2 becomes flat compared with the substantially triangular CT photographic regions CAc and CAc1. Both end portions (the portion in which the curvature changes) of the base portion are connected by a single arc to form the substantially triangular CT photographic region CAc2.

In the case that the X-ray CT photography is performed to the substantially triangular CT photographic region CAc in FIG. 19C, like the X-ray CT photography of the oval CT photographic region CAa in FIG. 9, the left-hand transverse shield plate 15a and the right-hand transverse shield plate 15b adjust the irradiation range of the X-ray cone beam BX according to the turning position (the turning angle) of the turning arm 30 such that the irradiation range is matched with the horizontal width of the substantially triangular CT photographic region CAc when viewed from the X-ray generation unit 10.

The CT photographic regions CA in FIGS. 19F and 19G are a substantially egg-shaped CT photographic region CAa3 having a long circular shape and a substantially rectangular CT photographic region CAa4 having round corners, respectively. Each of the substantially egg-shaped CT photographic region CAa3 and substantially rectangular CT photographic region CAa4 is constructed by a pair of parallel lines and a pair of arcs connecting end portions of the pair of parallel lines.

The oval CT photographic regions CAa in FIGS. 9 and 14, the elliptical CT photographic region CAb in FIG. 18, the oval CT photographic regions CAa1 and CAa2 in FIGS. 19A and 19B, and the substantially egg-shaped CT photographic region CAa3 and substantially rectangular CT photographic region CAa4 in FIGS. 19F and 19G are summarized as the substantially rectangular CT photographic region CA having the longer direction along the dental arch region X. The long circular shape includes substantially rectangular shapes with the substantial egg shape.

In the case that the X-ray CT photography is performed to each CT photographic region CA in FIG. 19, the shield plate transversely moving mechanism 16b adjusts the transverse positions of the left-hand transverse shield plate 15a and right-hand transverse shield plate 15b with respect to the outgoing port 12 during the X-ray CT photography, whereby the irradiation range in the transverse direction of the X-ray cone beam BX is adjusted according to the horizontal width of the CT photographic region CA. Therefore, the irradiation direction of the X-ray cone beam BX is properly changed in the transverse direction during the X-ray CT photography.

In the oval CT photographic regions CAa, CAa1, and CAa2, the elliptical CT photographic region CAb, the substantially egg-shaped CT photographic region CAa3, and the substantially rectangular CT photographic region CAa4, preferably the longer direction is set so as to extend along the dental arch region X, and more preferably the longer direction is set so as to be substantially parallel to a tangent at a require place on the curved line in the dental arch region X.

Thus, in the first preferred embodiment, with respect to the size, the range, and the position in the dental arch region X of the interest region (for example, the right-hand dentition photographic object OB1), the CT photographic region CA can be set as the oval, elliptical, substantially triangular, or long-circular-shape CT photographic region CA having the portion along the curved line of the dental arch region X. The interest region is surely irradiated with the X-ray from each direction while the excess X-ray exposure dose is reduced, thereby acquiring the projection data.

Figure 20:
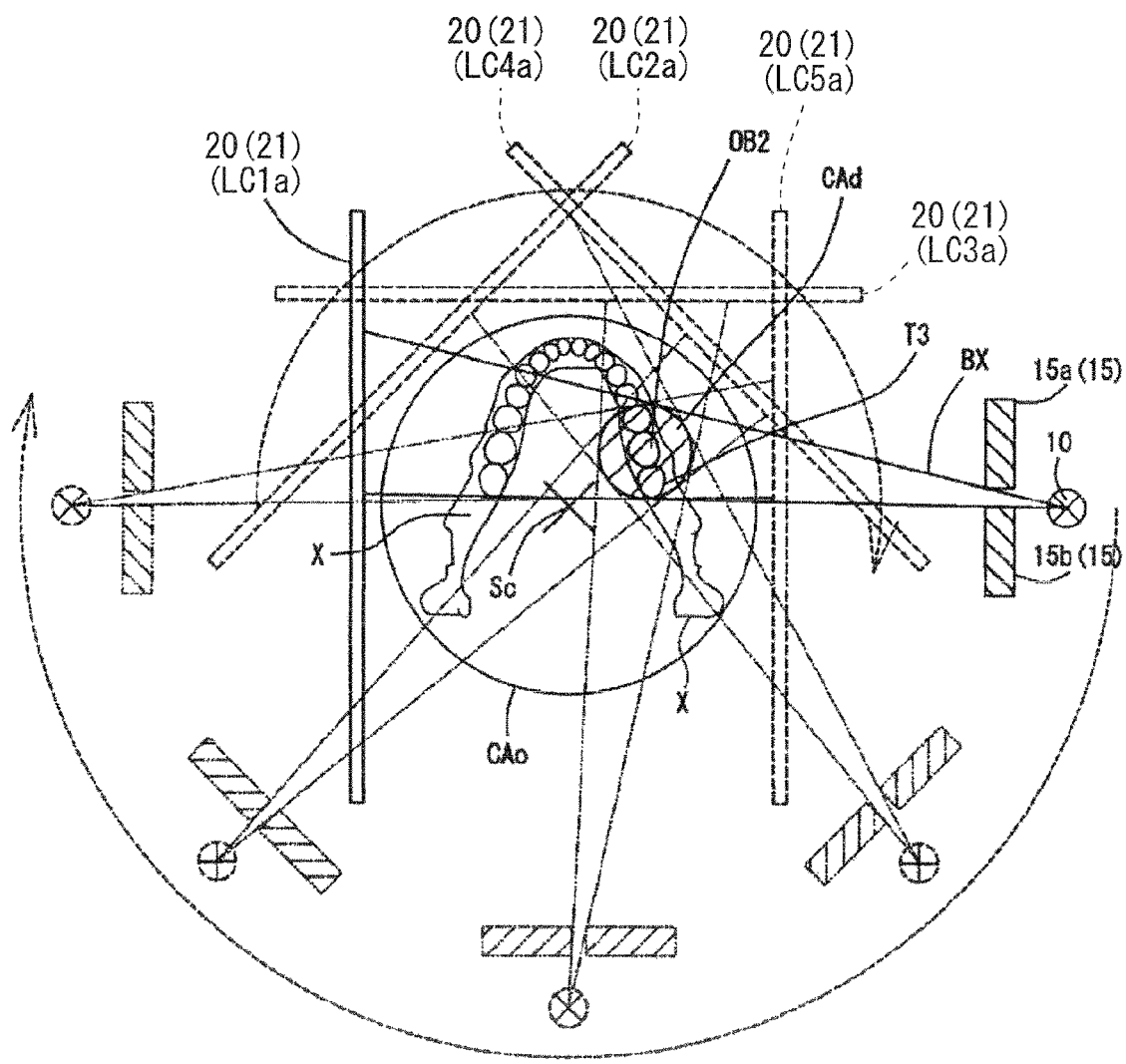
FIG. 20 is a schematic plan view illustrating a situation in which the X-ray CT photography of a local photographic object OB2 is performed.

FIG. 20 is a schematic plan view illustrating a situation in which the X-ray CT photography of a local photographic object OB2 is performed. For example, a diagnosis whether a wisdom tooth is in an overturned state in a buried wisdom tooth region, a diagnosis whether various tumors are widened, or a diagnosis of part of the dental arch region X or a surrounding portion (a tongue side portion or a cheek portion) of the dental arch region X is occasionally made in the dental clinic. In such cases, as illustrated in FIG. 20, the perfect-circle CT photographic region CAd is set with the right-hand molar group T3 of a couple of teeth as the local photographic object OB2.

In the case that the X-ray CT photography is performed to the perfect-circle CT photographic region CAd surrounding the local photographic object OB2, the shield plate transversely moving mechanism 16b adjusts the transverse positions of the left-hand transverse shield plate 15a and right-hand transverse shield plate 15b with respect to the outgoing port 12 according to the turning position (the turning angle) of the turning arm 30. Therefore, during the X-ray CT photography, the irradiation range and irradiation direction of the X-ray cone beam BX are adjusted according to the horizontal width of the perfect-circle CT photographic region CAd, which is viewed from the front side of the X-ray generation unit 10.

Figure 21:
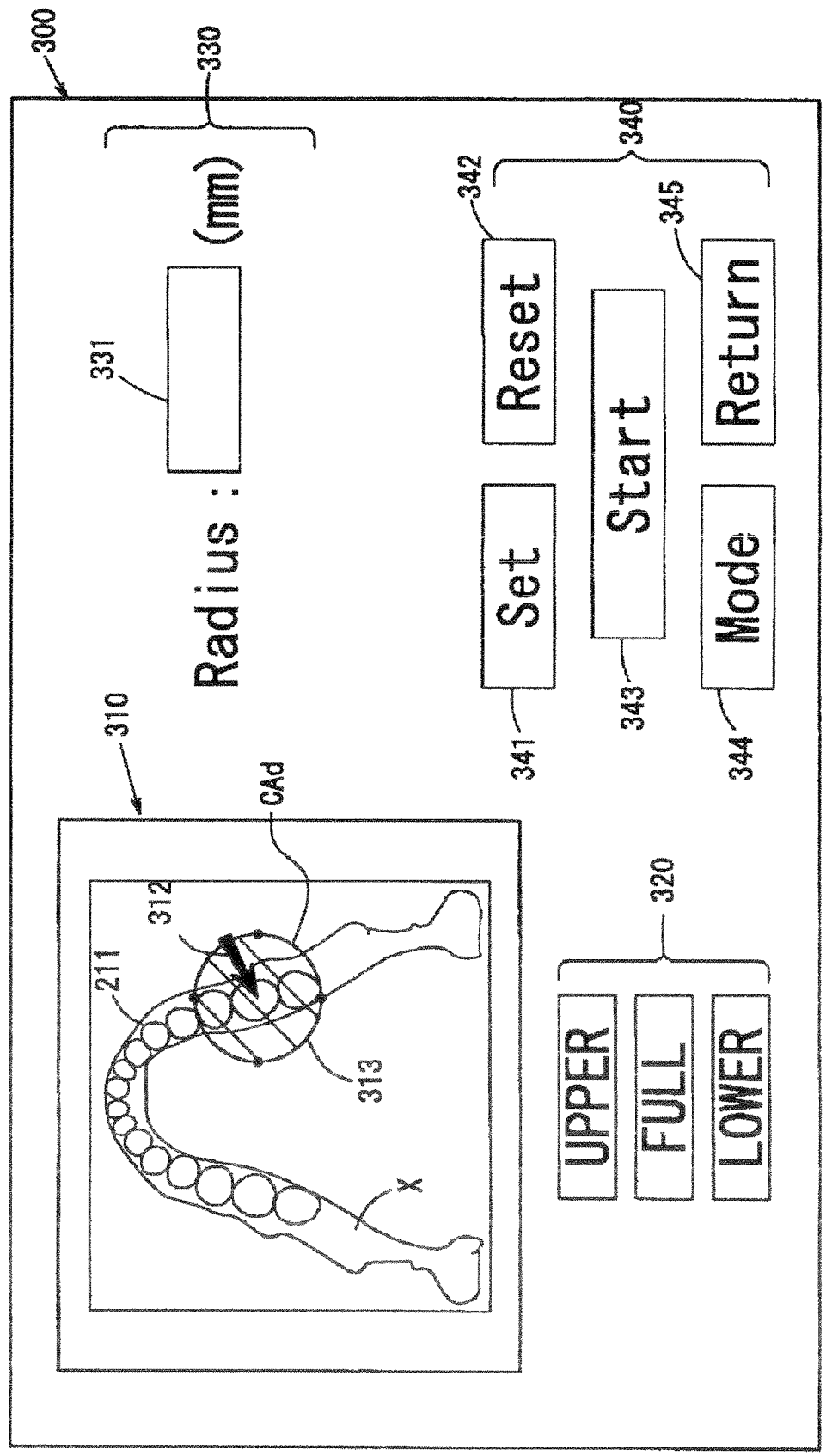
FIG. 21 is a view illustrating the CT photographic region setting screen that is used to set a perfect-circle CT photographic region CAd.

FIG. 21 is a view illustrating a CT photographic region setting screen 300 that is used to set a perfect-circle CT photographic region CAd. The CT photographic region setting screen 300 includes an image display unit 310, an upper-and-lower-jaw selection unit 320, a selection range setting unit 330, and a condition setting unit 340. The condition setting unit 340 includes a set button 341, a reset button 342, a start button 343, a mode button 344, and a return button 345. The functions of the upper-and-lower-jaw selection unit 320 and condition setting unit 340 are similar to those of the upper-and-lower-jaw selection unit 220 and condition setting unit 240 shown in FIG. 8.

The dental arch image 211, an assigning cursor 312 that assigns each point, the center assigned by the assigning cursor 312, and a perfect-circle CT photographic region line 313 corresponding to a radius assigned by the selection range setting unit 330 described later are displayed on the image display unit 310 while overlapping with one another.

The selection range setting unit 330 includes a text box 331 to which the radius (or the diameter) of the perfect-circle CT photographic region line 313 is input. Alternatively, the radius (or the diameter) of the perfect-circle CT photographic region line 313 may be set by moving the slider along the scale bar to which a scale mark of the radius (or the diameter) is previously added. The perfect-circle CT photographic region line 313 is selected on the image display unit 310 using the assigning cursor 312, and the perfect-circle CT photographic region line 313 may be enlarged or contracted by the drag manipulation to assign the size thereof.

In order to set the perfect-circle CT photographic region CAd, the perfect-circle CT photographic region line 313 is set in the CT photographic region setting screen 300 displayed on the manipulation display unit 61 so as to surround the local photographic object OB2. Particularly, one of the upper jaw, the lower jaw, and the upper and lower jaws is selected by the upper-and-lower-jaw selection unit 320 according to the position of the local photographic object OB2. Then, in the dental arch image 211 displayed on the image display unit 310, the center of the perfect-circle CT photographic region line 313 is assigned by the assigning cursor 312, and the radius (or the diameter) of the perfect-circle CT photographic region line 313 is input to the text box 331. Accordingly, the position and size of the perfect-circle CT photographic region line 313 are set such that the local photographic object OB2 is surrounded by the perfect-circle CT photographic region line 313.

The assignment information (the positional information on the center of the perfect-circle CT photographic region CAd and the information on the radius (or the diameter)) input on the CT photographic region setting screen 300 is transmitted to the information processing device 8. The information processing device 8 that receives the assignment information transmits the information on the perfect-circle CT photographic region line 313 to the manipulation display unit 61. The manipulation display unit 61 that receives the information on the perfect-circle CT photographic region line 313 displays the dental arch image 211 and the perfect-circle CT photographic region line 313 on the image display unit 310 while the dental arch image 211 and the perfect-circle CT photographic region line 313 overlap with each other.

In the case that the perfect-circle CT photographic region line 313 is properly set to the desired position and range on the dental arch image 211, the operator (for example, the practitioner) presses the set button 341. Therefore, the information on the perfect-circle CT photographic region CAd corresponding to the perfect-circle CT photographic region line 313 is transmitted to the information processing device 8. When the start button 343 is pressed, the main body 2 starts the X-ray CT photography of the local photographic object OB2 as described later.

Thus, the X-ray CT photography can be properly performed to the right-hand dentition photographic object OB2, which is of the interest region, by setting the perfect-circle CT photographic region CAd surrounding the local photographic object OB2.

In the X-ray CT photographic apparatus 1, the panoramic photography can be performed while a shaft center of the turning shaft 31 is fixed to a specific position on the horizontal plane.

FIG. 22 is a schematic plan view illustrating a situation in which the panoramic photography is performed. In the case that the panoramic photography is performed, the beam shaping mechanism 13 regulates the X-ray cone beam BX to adjust the X-ray slit beam BXP for the panoramic photography. The left-hand transverse shield plate 15a and the right-hand transverse shield plate 15b adjust the irradiation direction of the X-ray slit beam BXP according to the turning position (the turning angle) of the turning arm 30.

The X-ray slit beam BXP is formed by a panoramic photography opening 17c constructed by the beam shaping mechanism 13 as illustrated in FIG. 6C. As illustrated in FIG. 22, the X-ray generation unit 10, the left-hand transverse shield plate 15a, the right-hand transverse shield plate 15b, and the X-ray detection unit 20 (particularly, X-ray detector 21) turn by 180 degrees together with the turning arm 30 (not illustrated) from a turning starting position LC1 that is of the initial position, and turn to a turning ending position.

In FIG. 22, the initial position LC1 of the X-ray generation unit 10 is located right beside the dental arch region X, and then the X-ray generation unit 10 turns on a rear side of the head portion. The turning center Sc is located on the center of the subject M1, and set to the neighborhood between the right and left back teeth.

FIG. 22 illustrates the state in which the turning arm 30 rotates every 30 degrees to move the X-ray generation unit 10 to the initial position LC1 and turning positions LC2, LC3, and LC4. The state in which the turning angle ranges from 90 degrees to 180 degrees is not illustrated in FIG. 22. In the case that the turning angle of the turning arm 30 changes from 90 degrees to 180 degrees, the X-ray generation unit 10 moves sequentially to the symmetric positions of the turning positions LC3 and LC2 and initial position LC1.

During the panoramic photography, the dental arch region X is continuously irradiated with the X-ray slit beam BXP. In the initial position LC1, the positions of the left-hand transverse shield plate 15a and right-hand transverse shield plate 15b are adjusted such that the irradiation direction of the X-ray slit beam BXP is biased along the x-axis direction with respect to the horizontal direction reference center line SCL connecting an X-ray tube focal point of the X-ray generation unit 10 and the center of the detection surface 21' of the X-ray detector 21. Particularly, the irradiation direction of the X-ray slit beam BXP is adjusted such that a direction of a normal to the curved line along the dental arch region X is irradiated with the X-ray slit beam BXP.

Specifically, although the irradiation direction of the X-ray slit beam BXP is slightly biased onto the −x side with respect to the horizontal direction reference center line SCL at the initial position LC1, as the X-ray generation unit 10 moves from the initial position LC1 to the turning position LC2, the irradiation direction of the X-ray slit beam BXP is slightly biased onto the +x side with respect to the horizontal direction reference center line SCL. In other words, the bias amount onto the −x side in the turning position LC2 is smaller than the bias amount onto the −x side in the initial position LC1, and therefore the bias onto the +x side is adjusted. As the X-ray generation unit 10 moves from the turning position LC2 to the turning position LC3, the irradiation direction of the X-ray slit beam BXP is further biased onto the +x side with respect to the horizontal direction reference center line SCL.

As the X-ray generation unit 10 moves from the turning position LC3 to the turning position LC4, the irradiation direction of the X-ray slit beam BXP is returned to the −x side with respect to the horizontal direction reference center line SCL. When the X-ray generation unit 10 reaches the turning position LC4, the irradiation direction of the X-ray slit beam BXP is adjusted so as to be aligned with the horizontal direction reference center line SCL.

By controlling the irradiation direction of the X-ray slit beam BXP, the X-ray slit beam BXP moves so as to form an envelope EM.

FIG. 23 is a plan view illustrating various CT photographic regions CA. As illustrated in FIG. 23, for example, the relatively large perfect-circle CT photographic region CAd (the large perfect-circle CT photographic region CAj including part of the jawbone and the wisdom tooth), which includes part of the jawbone and the wisdom tooth and has the diameter of 100 mm, may be set compared with relatively small perfect-circle CT photographic region CAo having the conventional diameter of 80 mm.

In the case that the CT photographic region CA is set to the substantially triangular CT photographic region CAc, the X-ray exposure dose can be reduced with respect to the region hatched by diagonal lines in FIG. 23 compared with the perfect-circle CT photographic region CAj. Therefore, in the case that the substantially triangular CT photographic region CAc can cover the interest region, advantageously the X-ray exposure dose can be reduced compared with the case that the CT photographic region CA is set to the perfect-circle CT photographic region CAj having the diameter of 100 mm.

FIG. 25 is a view illustrating a situation in which a read region is changed in a detection surface 21' of the X-ray detector 21. FIG. 25 illustrates the detection surface 21' of the X-ray detector 21 when the X-ray detector 21 moves to turning positions LC1a, LC2a, LC3a, LC4a, and LC5a while the X-ray CT photography of the perfect-circle CT photographic region CAd is performed as illustrated in FIG. 20.

As illustrated in FIG. 25, the detection surface 21' of the X-ray detector 21 is constructed by many pixels, and the pixel is divided into segments, namely, 10 detection segments 22a to 22j in the x-axis direction. In the X-ray detector 21, the X-ray detection signal is transmitted to the information processing device 8 in units of detection segments 22a to 22j. The X-ray detection controller included in the main body controller 60 in FIG. 3 performs read control of the X-ray detection signal to the detection segments 22a to 22j. The X-ray detection controller thus acts as a read region controller.

A MOS sensor, a CCD sensor, and a TFT can be cited as an example of the X-ray detector 21. Additionally, for example, a Flat Panel Detector (FPD) such as a CMOS sensor, an X-ray fluorescence intensifier tube (XII), other solid-state imaging elements and the like can be used as the X-ray detector 21.

During the X-ray CT photography, the X-ray detection controller changes the read region where the X-ray detection signal is read in the X-ray detector 21 according to the irradiation range of the X-ray cone beam BX. More specifically, the X-ray detection controller controls the X-ray detector 21 such that the X-ray detection signal is read only from a portion (an irradiated region XA1) irradiated with the X-ray cone beam BX in the detection surface 21'.

For example, in the case that the X-ray detector 21 is located in the turning position LC1a (see FIG. 20), the irradiated region XA1 overlaps with the detection segments 22f, 22g, and 22h in the detection segments 22a to 22j as illustrated in FIG. 25. Therefore, the X-ray detection controller activates only the detection segments 22f, 22g, and 22h and acquires the detection signal from the detection segments 22f, 22g, and 22h at a required frame rate. As used herein, the term of activation means that the detection segment is activated so as to be able to generate the detection signal. Similarly, in the case that the X-ray detector 21 is located in the turning position LC2a, the X-ray detection controller activates the detection segments 22g, 22h, and 22i to acquire the detection signal. In the case that the X-ray detector 21 is located in the turning position LC3a, the X-ray detection controller activates the detection segments 22f, 22g, and 22h to acquire the detection signal. In the case that the X-ray detector 21 is located in the turning position LC4a, the X-ray detection controller activates the detection segments 22e, 22f, and 22g to acquire the detection signal. In the case that the X-ray detector 21 is located in the turning position LC5a, the X-ray detection controller activates the detection segments 22c, 22d, and 22e to acquire the detection signal. Thus, the read region of the X-ray detection signal is changed according to the position of the irradiated region XA1 irradiated with the X-ray cone beam BX in the detection surface 21'.

As described above, in the first preferred embodiment, based on the turning position (the turning angle) of the turning arm 30, the irradiation range of the X-ray cone beam BX is changed in the x-axis direction according to the shape of the CT photographic region CA. For this reason, the irradiated region XA1 is also changed in the x-axis direction of the irradiation range. Accordingly, as illustrated in FIG. 25, the read region (that is, the activated detection segment) is also changed in the x-axis direction during the X-ray CT photography.

The X-ray detection signal can be efficiently read from the X-ray detector 21 by changing the read region. When the CT photographic region CA is set through the CT photographic region setting screen 200, the irradiation range of the X-ray cone beam BX is also fixed according to the turning position (the turning angle) of the turning arm 30. Therefore, the irradiated region XA1 is inevitably fixed. Accordingly, the detection segment that should be activated in the detection segments 22*a* to 22*j* can easily be determined according to the turning position (the turning angle) of the turning arm 30. Specifically, the activated detection segment is determined by the calculation processing in which a predetermined program is executed by the main body controller 60 or calculation processor 801*b*.

During the panoramic photography (see FIG. 22), the irradiated region of the X-ray slit beam BXP in the detection surface 21' of the X-ray detector 21 is displaced in the x-axis direction according to the turning position (the turning angle) of the turning arm 30. The activated detection segment in the detection segments 22*a* to 22*j* in FIG. 25 is changed in the x-axis direction, which allows the detection signal to be efficiently read.

FIG. 26 is a view illustrating the detection surface 21*a*' of another X-ray detector 21*a*. The X-ray detector 21*a* includes 20 detection segments in total. The 20 detection segments are obtained by vertically dividing each of the detection segments 22*a* to 22*j* in FIG. 25 into two. In this case, for example, it is assumed that the CT photographic region CA is set to part of the upper jaw (or part of the lower jaw), that the irradiation range of the X-ray cone beam BX is regulated in the z-axis direction (see FIG. 13), and that only the upper-side (or the lower-side) of the detection surface 21*a*' is irradiated with the X-ray cone beam BX as illustrated in FIG. 26. At this point, some upper-stage-side detection segments are selectively activated according to the irradiated region XA2 of the X-ray cone beam BX, which allows the X-ray detection signal to be more efficiently read.

The X-ray detection controller (the read region controller) may be configured to change the frame rate, at which the X-ray detection signal is read from the read region (that is, the activated detection segment), according to the turning position (the turning angle) about the turning shaft 31 of the turning arm 30. The image quality can be improved by raising the frame rate. Particularly, in the small read region (that is, in the small number of activated detection segments), a data amount of the X-ray detection signal that should be transferred becomes relatively small. For this reason, even if the frame rate is enhanced, there is a relatively small influence on the transfer efficiency of the X-ray detection signal. On the other hand, the image signal can efficiently be transferred from the X-ray detector by lowering the frame rate. Particularly, in the large read region (that is, in the large number of activated detection segments), the data amount of the X-ray detection signal that should be transferred becomes relatively large. In this case, the X-ray detection signal can be efficiently transferred by lowering the frame rate.

The size of the read region depends on the size of the CT photographic region, and the size of the CT photographic region can be set by a CT photographic region setting means such as the CT photographic region setting screen 200. Accordingly, the CT photographic region setting means can be recognized as a frame rate setting unit.

The frame rate may be changed according to a kind of photographic area (the CT photographic region), a position of the photographic target area and a photographic purpose. For example, photographic target area selection means (not illustrated) for selecting the frame rate according to the area may be provided based on the selection or input of the area such that a high-priority area where fine observation is required is photographed at a high frame rate, and such that other areas are photographed at a low frame rate. Alternatively, a photographic purpose selection means (not illustrated) for selecting the frame rate may be provided according to the photographic purpose when the photographic purpose is selected or input.

The photographic target area selection means or the photographic purpose selection means is an example of the frame rate setting unit from the viewpoint of changing the frame rate.

The frame rate may be changed according to the position of the photographic target area (the CT photographic region). For example, it is assumed that the photographic target area is located near the area such as a cervical vertebrae where the X-ray scattering is easily generated. In this case, a period (a period T1) during which the X-ray cone beam BX is transmitted through not the cervical vertebrae but the photographic target area and a period (a period T2) during which the X-ray cone beam BX is transmitted through both the cervical vertebrae and the photographic target area are conceivable during the X-ray CT photography. Because the relatively clear projection image data (projection data) is obtained in the period T1, the photography is performed at the high frame rate, and the photography is performed at the lower frame rate in the period T2 than that in the period T1. The photographic target area is set by the CT photographic region setting means such as the CT photographic region setting screen 200. Accordingly, the CT photographic region setting means can be recognized as the frame rate setting unit.

In the X-ray CT photographic apparatus 1, the X ray CT photographic in which the CT photographic region CA is set may be performed such that the whole detection surface 21' of the X-ray detector 21 is irradiated with the X-ray cone beam BX during the X-ray CT photography. In this case, the X-ray generation unit 10 emits the X-ray cone beam BX1 for large irradiation field CT in FIG. 5A. The X-ray cone beam BX1 for large irradiation field CT is set such that the whole detection surface 21' of the X-ray detector 21 is irradiated with the X-ray cone beam BX1 for large irradiation field CT. In the irradiation of the X-ray cone beam BX1 for large irradiation field CT, the whole detection surface 21' in FIG. 25, namely all the detection segments, are activated during the X-ray CT photography. The photography mode performed by the X-ray CT photographic apparatus 1 may be switched between the X-ray CT photography mode in which the whole detection surface 21' is used and the X-ray CT photography mode in which the read region is controlled through a photography mode switching unit such as the mode button 244.

The X-ray CT photography mode in which the whole detection surface 21' is used is a whole region CT photography mode in which the X-ray CT photography is performed in the whole region of the detection surface 21', and the X-ray CT photography mode in which the read region is controlled is a partial region CT photography mode in which the X-ray CT photography is performed in the partial region of the detection surface 21'.

In the X-ray CT photography mode in which the whole detection surface 21' is used, the whole detection surface 21' is used in the x-axis direction. However, sometimes the X-ray CT photography mode in which the whole detection surface 21' is used is further divided into a mode in which the X-ray irradiation is performed while restricted in the z-axis direction and a mode in which the X-ray irradiation is performed while not restricted in the x-axis direction and z-axis direction. In the mode in which the X-ray irradiation is performed while restricted in the z-axis direction, for example, as illustrated in FIG. 26, the CT photographic region CA is set to the whole upper jaw (or the whole lower jaw), the irradiation range of the X-ray cone beam BX is regulated in the z-axis direction, and only the upper side (or the lower side) of the detection surface 21a' is irradiated with the X-ray cone beam BX. All the detection segments only on the upper-stage side (or the lower-stage-side) are activated according to an irradiated region XA2 of the X-ray cone beam BX.

At this point, elements (the detection segments) arrayed in the x-axis direction are referred to as a "row", and elements arrayed in the z-axis direction are referred to as a "column". In FIG. 25, the detection segments are arrayed in 10 columns. It is conceivable that the number of columns of the detection segments can be increased by thinning the horizontal width of one detection segment. On the other hand, it is also conceivable that the number of columns of the detection segments can be decreased by increasing the horizontal width of one detection segment. For example, the detection segments are disposed in three columns that are disposed in right, left and center, respectively, or two columns that are in right and left.

The same holds true for the number of divided pieces of the detection surface 21' in FIG. 26 in the z-axis direction. In other words, the detection surface 21' may be constructed by the detection segments disposed in at least three rows.

The read region may be controlled in units of pixels. In this case, the detection surface 21' is controlled such that only the pixel corresponding to the irradiated region XA2 of the X-ray cone beam BX is activated as the read region. A region that is wider than the irradiated region XA2 (where the irradiated region XA2 is matched with the read region) by one pixel (or at least two pixels) may be activated as the read region.

In the case that the detection surface 21' is controlled such that only the pixel of the irradiated region XA2 of the X-ray cone beam BX is activated as the read region, the read region of the detection surface 21' may be changed in the z-axis direction during the X-ray CT photography. For example, in the first preferred embodiment in FIG. 13, the range where the detection surface 21' is irradiated with the X-ray cone beam BX is displaced in the z-axis direction in FIGS. 13A and 13B. The read region may be changed according to the displacement of the range where the detection surface 21' is irradiated with the X-ray cone beam BX.

Figure 27:
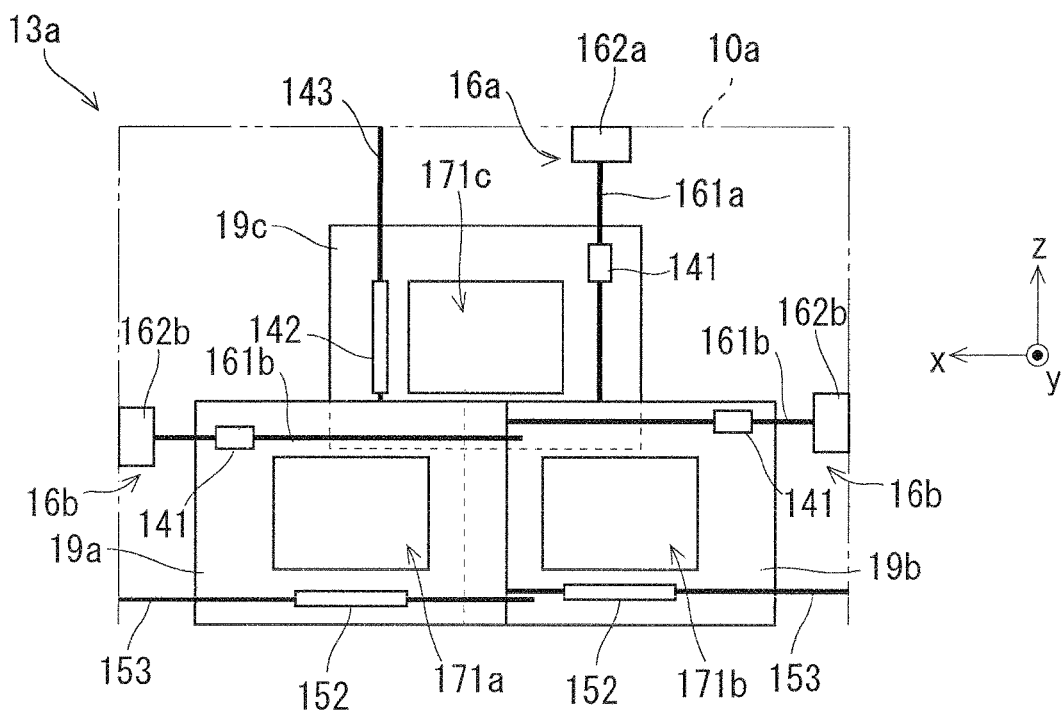
FIG. 27 is a schematic front view of another beam shaping mechanism.

FIG. 27 is a schematic front view of another beam shaping mechanism 13a. In FIG. 27, the element identical or similar to that in FIG. 4 is designated by the identical numeral, and the description is omitted. The beam shaping mechanism 13a mainly includes shield plates 19a, 19b, and 19c. The shield plates 19a, 19b, and 19c are sequentially disposed in the y-axis direction. Rectangular openings 171a, 171b, and 171c are formed in the central portions of the shield plates 19a, 19b, and 19c, respectively. The shield plate transversely moving mechanism 16b is connected to the shield plates 19a and 19b, and the shield plate longitudinally moving mechanism 16a is connected to the shield plate 19c. Therefore, the shield plate 19a and 19b can be moved in the transverse direction, and the shield plate 19c can be moved in the longitudinal direction.

FIG. 28 is an explanatory view of the positioning of the shield plates 19a, 19b, and 19c. In FIGS. 28A to 28D, the shield plate 19c is disposed on the backside of the shield plate 19a (or the shield plate 19b) so as to overlap with the shield plate 19a (or the shield plate 19b). A subject N1 in FIG. 28 is a body that is virtually disposed on the +y side of the beam shaping mechanism 13a. As illustrated in FIGS. 28A to 28D, the shield plates 19a and 19b are deviated in the transverse direction by a required length, whereby the opening 17 can be formed such that a +x-side portion (FIG. 28A) of the subject N1, a central portion (FIG. 28B) in the x-axis direction of the subject N1, a −x-side portion (FIG. 28C) of a subject M2, and a whole portion (FIG. 28D) of the subject N1 are irradiated with the X-ray cone beam BX.

Figure 28A:
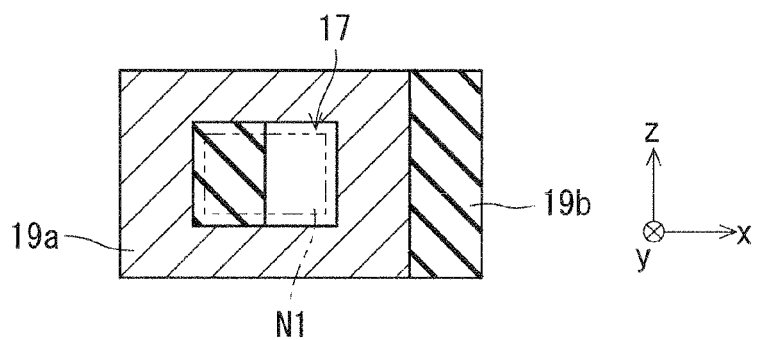
FIG. 28 (FIGS. 28A through 28E) is an explanatory view of the positioning of three shield plates.
Figure 28C:
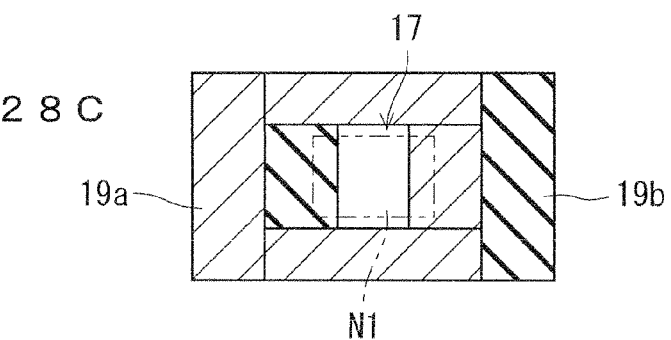
Figure 28B:
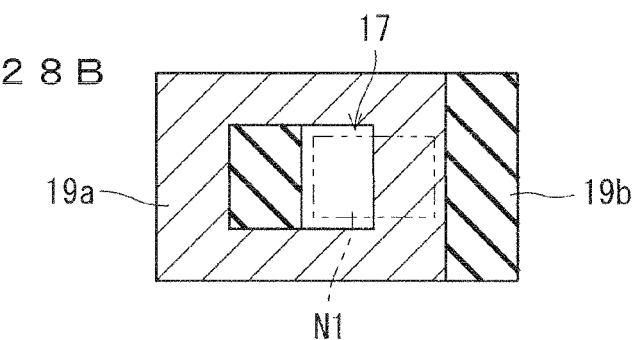
Figure 28D:
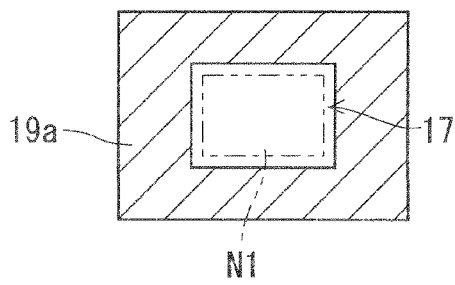
Figure 28E:
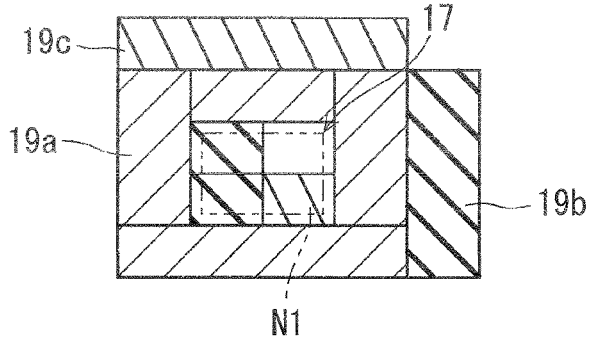

The longitudinal position of the shield plate 19c is changed while the transverse positions of the shield plates 19a and 19b are adjusted, which allows the opening 17 to be formed such that only the +x-side portion and +z-side portion of the subject N1 are irradiated with the X-ray cone beam BX as illustrated in FIG. 28E.

The beam shaping mechanism 13a in FIG. 27 includes the shield plates 19a, 19b, and 19c. However, in the case that the irradiation range of the X-ray cone beam BX is controlled only in the transverse direction, the beam shaping mechanism 13a may only include the shield plates 19a and 19b moving in the transverse direction as illustrated in FIGS. 28A to 28D.

FIG. 29 is an explanatory view of the positioning of the shield plates 19a and 19c. As illustrated in FIG. 29, the shield plate 19c is configured to be able to move in not only the longitudinal direction but also the transverse direction, which allows the elimination of the shield plate 19b. Although the specific configuration to move the shield plate 19c is not illustrated, for example, the shield plate 19c in FIG. 27 and the shield plate longitudinally moving mechanism 16a are provided on a base stage (not illustrated), and the base stage is moved in the transverse direction by a moving mechanism similar to the shield plate transversely moving mechanism 16b. More specifically, the shield plates 19a and 19c are deviated in the transverse direction by the required length, whereby the opening 17 is formed such that the +x-side portion of the subject N1 is irradiated with the X-ray cone beam BX as illustrated in FIG. 29A or such that the −x-side portion of the subject N1 is irradiated with the X-ray cone beam BX as illustrated in FIG. 29B.

Figure 29A:
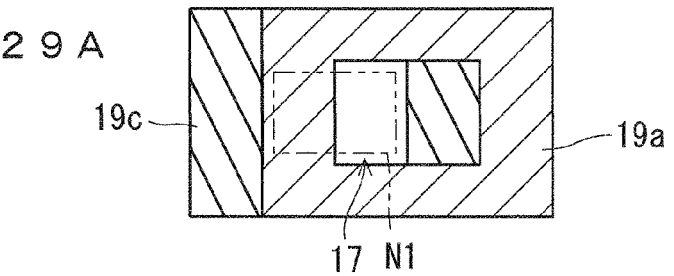
FIG. 29 (FIGS. 29A through 29E) is an explanatory view of the positioning of two shield plates.
Figure 29B:
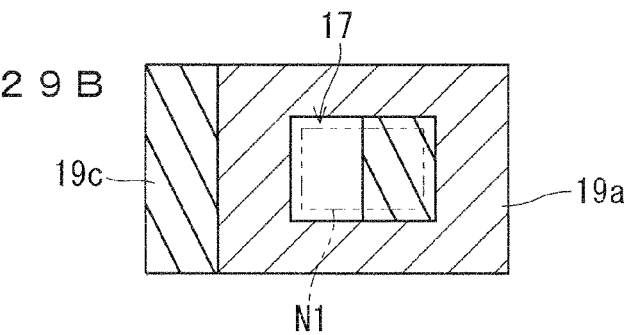
Figure 29C:
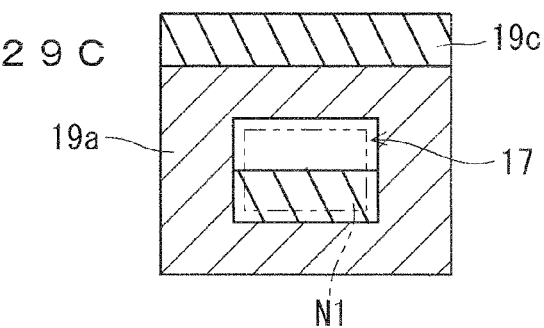
Figure 29D:
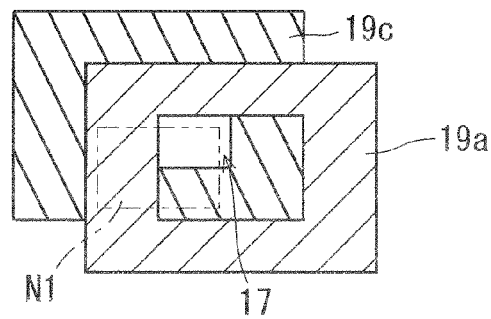
Figure 29E:
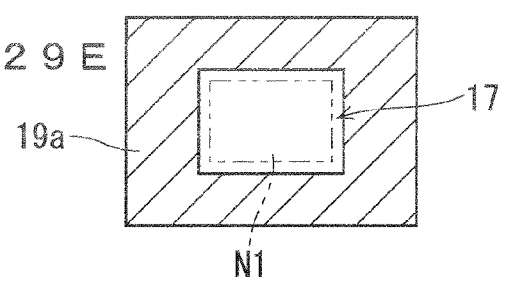

As illustrated in FIG. 29C, the shield plate 19c is deviated in the longitudinal direction by the required length with respect to the shield plate 19a, which allows the opening 17 to be formed such that only the +z-side portion of the subject N1 is irradiated with the X-ray cone beam BX. As illustrated in FIG. 29D, the shield plate 19a is deviated by the required length with respect to the shield plate 19c, which allows the opening 17 to be formed such that only the +z-side portion and the −x-side portion of the subject N1 is irradiated with the X-ray cone beam BX. As illustrated in FIG. 29E, the shield plates 19a and 19c overlap with each other in the same position, which allows the opening 17 to be formed such that the whole subject N1 is irradiated with the X-ray cone beam BX.

2. Second Preferred Embodiment

In the first preferred embodiment, the turning arm 30 is configured to be able to move in the X-axis direction and the Y-axis direction with respect to the subject M1. Alternatively, the turning arm 30 may be fixed while the turning shaft is fixed. In the first preferred embodiment, the turning shaft 31 of the turning arm 30 extends in the vertical direction. Alternatively, the turning arm may not have a structure in which the turning shaft extends vertically.

Figure 31:
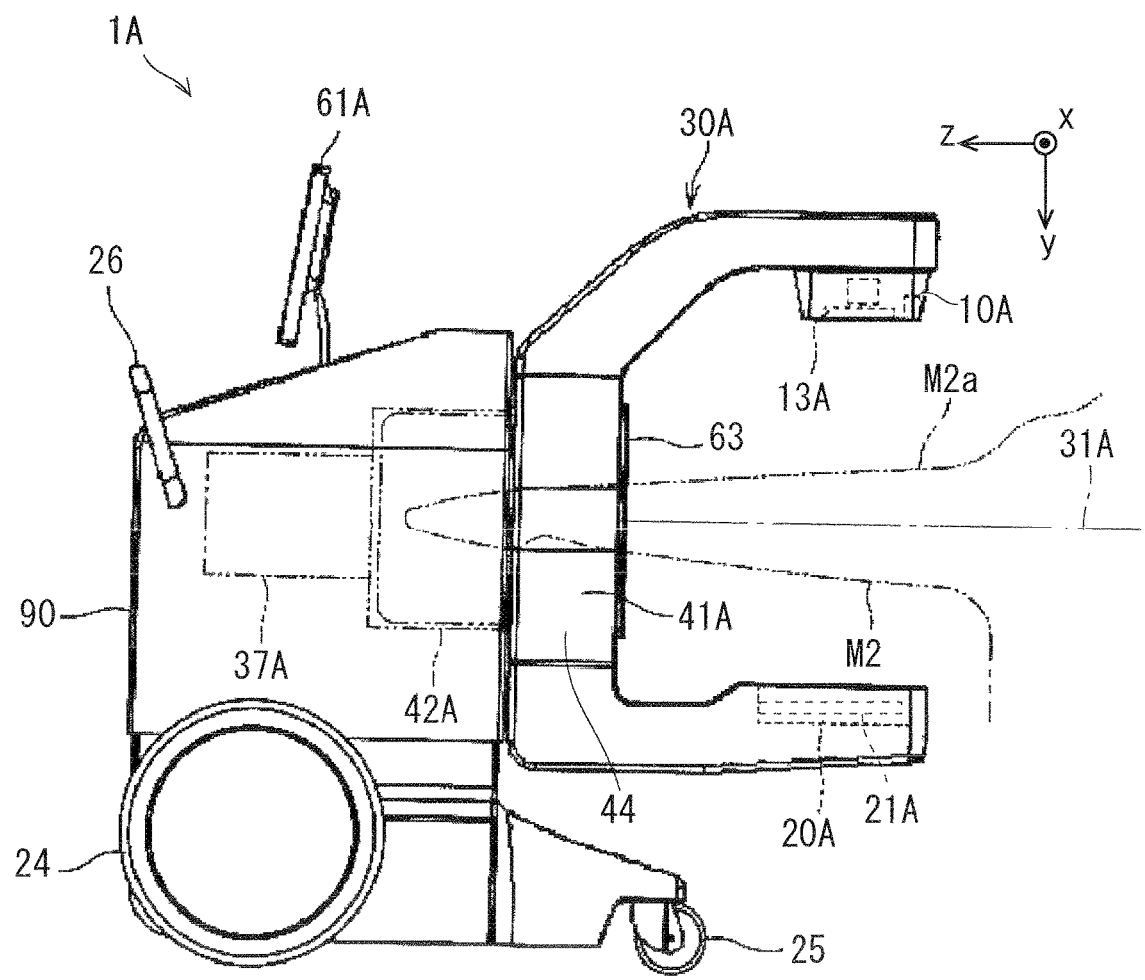
FIG. 31 is a side view of the X-ray CT photographic apparatus of the second preferred embodiment.

FIG. 30 is an overall perspective view of an X-ray CT photographic apparatus 1A according to a second preferred embodiment. In the second preferred embodiment, a rotating shaft (a shaft 31A) of a rotation support unit 41A (described later) extends horizontally. FIG. 31 is a side view of the X-ray CT photographic apparatus 1A of the second preferred embodiment. The X-ray CT photographic apparatus 1A performs the X-ray CT photography of a local portions of the patient, such as the head portion, the cervical vertebrae, an arm joint, a hand finger, a lumbus, a hip joint, a knee, and a leg. Japanese Patent Application Laid-Open No. 2011-25012 discloses a detailed configuration of the X-ray CT photographic apparatus 1A.

The X-ray CT photographic apparatus 1A includes a base body 90, a turning arm 30A, a turning motor 37A, and a cylindrical body 63.

The turning arm 30A is attached to the base body 90. In FIG. 30, the turning arm 30A is attached to a principal surface along the vertical direction of the base body 90. In the description described later, for the sake of convenience, in the base body 90, the side on which the turning arm 30A is provided is referred to as a front side, and the opposite side to the front side is referred to as a rear side.

A pair of wheels 24 and an auxiliary wheel 25 are provided in a lower portion of the base body 90. The pair of wheels 24 and the auxiliary wheel 25 can roll on a floor, and the auxiliary wheel 25 can turn around. A handle 26 is provided in a rear portion of the upper-side portion of the base body 90. A user or the like pushes the base body 90 while manipulating the traveling direction by the handle 26, thereby moving and transferring the X-ray CT photographic apparatus 1A on the floor. In other words, the X-ray CT photographic apparatus 1A is constructed as a portable X-ray CT photographic apparatus for which the installation place can be changed. The configuration in which the X-ray CT photographic apparatus 1A can be moved is not limited to the second preferred embodiment.

A manipulation display unit 61A is provided in the rear portion of the upper-side portion of the base body 90. Like the manipulation display unit 61 in FIG. 1, the CT photographic region setting screen 200 and the like are displayed on the manipulation display unit 61A, and the operator (the practitioner or the like) uses the manipulation display unit 61A to set the CT photographic region CA.

A CT photography processing unit (not illustrated) is included in the base body 90. The CT photography processing unit is a processing control unit constructed by a general computer including a CPU and a RAM. The CT photography processing unit has a function similar to that of the main body controller 60 or information processing device 8 of FIG. 1.

An attaching hole 90h is made in the principal surface of the base body 90, and the turning arm 30 is attached to the base body 90 using the attaching hole 90h.

The turning motor 37A is constructed by a motor in which the rotation speed and the rotation angle and the like can be controlled. While the drive shaft portion of the turning motor 37A is oriented toward the substantial center of the attaching hole 90h with its drive shaft portion being in a substantially horizontal state, the turning motor 37A is supported in the base body 90 in a fixed position or a variable position. An example in which the turning motor 37A is supported while the position of the turning motor 37A is variable in the base body 90 is described later as a modification. The rotation support unit 41A (described later) is coupled to the turning motor 37A, thereby rotatably supporting the turning arm 30A.

The turning arm 30A is formed into a U-shape, and the turning arm 30A supports the X-ray generation unit 10A and the X-ray detection unit 20A at their respective ends while the X-ray generation unit 10A and the X-ray detection unit 20A are opposed to each other. The turning arm 30A also includes the rotation support unit 41A, which supports the turning arm 30A while the turning arm 30A is rotatable with respect to the base body 90.

The rotation support unit 41A includes an inside rotation support unit 42A (the second support body retention unit) and an outside rotation support unit 44. The inside rotation support unit 42A is formed into a cylindrical shape with a bottom, and provided in the base body 90 through the attaching hole 90h. The outside rotation support unit 44 is constructed by a member larger than the inside rotation support unit 42A, and provided on the outside of the base body 90 in the attaching hole 90h.

A ball bearing unit (not illustrated) is provided in a bottom portion of the inside rotation support unit 42A. The ball bearing unit includes an outer ring member and an inner ring member, which are coupled to each other so as to be relatively rotatable with a rolling body, such as a ball, interposed therebetween. The turning motor 37A rotates the inner ring member through a power transmission mechanism such as a rotating body (not illustrated), thereby rotating the rotation support unit 41A.

The X-ray generation unit 10A includes the X-ray generator, such as the X-ray tube, which generates the X-ray cone beam BX. The X-ray generation unit 10A emits the X-ray cone beam BX toward the X-ray detection unit 20A attached to the other end portion of the turning arm 30A. Like the X-ray generation unit 10, the X-ray generation unit 10A includes a beam shaping mechanism 13A that adjusts the irradiation range of the X-ray cone beam. The beam shaping mechanism 13A has the a configuration similar to that of the beam shaping mechanism 13 in FIG. 4.

The X-ray detection unit 20A includes an X-ray detector 21A. Like the X-ray detectors 21 and 21a in FIGS. 25 and 26, in the X-ray detector 21A, the detection surface that detects the X-ray is divided into plural detection segments. The X-ray detection controller that is included in the CT photography processing unit incorporated in the base body 90 changes the read region of the X-ray detection signal in the detection surface of the X-ray detector 21A.

The turning arm 30A turns about the shaft 31A when the rotation support unit 41A rotates about the shaft 31A extending in the horizontal direction by the drive of the turning motor 37A. Therefore, the X-ray generation unit 10A and X-ray detection unit 20A, which are attached to the turning arm 30A, turn about the shaft 31A.

In the rotation support unit 41A, a hollow portion (not illustrated) is provided around the turning shaft 31A, and the cylindrical body 63 is fitted in the hollow portion. However, the cylindrical body 63 can be fixed to not the rotation support unit 41A but the base body 90. For this reason, the cylindrical body 63 does not turn together with the rotation support unit 41A. Accordingly, even if the turning arm 30A turns, the cylindrical body 63 does not turn together with the turning arm 30A. The cylindrical body 63 is configured in the above manner, which allows the patient to safely place part of the body in the cylindrical body 63. In order to achieve the same purpose, a bearing mechanism such as a bearing can be interposed between the cylindrical body 63 and the rotation support unit 41A, and the cylindrical body 63 may be fixed while being rotatable with respect to the rotation support unit 41A.

In the case that the X-ray CT photographic apparatus 1A photographs the local portion of the patient, for example, an upper arm M2a, the upper arm M2a of the patient is disposed along the shaft 31A in the position between the X-ray generation unit 10A and the X-ray detection unit 20A (see FIG. 31). At this point, the X-ray generation unit 10A and the X-ray detection unit 20A turn about the shaft 31A by the drive of the turning motor 37A. The irradiation range of the X-ray cone beam BX is adjusted according to the turning position (the turning angle) of the turning arm 30A so as to be suitable to the position in the z-axis direction and the width in the x-axis direction of the CT photographic region CA when the CT photographic region CA is viewed from the side of the X-ray generation unit 10. In the X-ray detector 21A, the read region of the X-ray detection signal is changed according to the irradiation range of the X-ray cone beam BX.

Even if the shaft 31A extends in the horizontal direction during the X-ray CT photography like the X-ray CT photographic apparatus 1A, the irradiation range of the X-ray cone beam BX can be adjusted by the beam shaping mechanism 13A. Therefore, the X-ray exposure dose of the subject M2 can be reduced outside the CT photographic region CA. Additionally, the read region of the X-ray detection signal in the X-ray detector 21A is changed according to the irradiation range of the X-ray cone beam BX, so that the X-ray detection signal can efficiently be transferred.

3. Modifications

Although the first and second preferred embodiments are described above, the present invention is not limited to these preferred embodiments, and various modifications can be made.

For example, in the X-ray CT photographic apparatus 1 of the first preferred embodiment, the dental arch image 211 is displayed on the image display unit 210. Alternatively, the X-ray projection image of the subject M1 or a schematic diagram (such as an illustration) of the subject M1 may be displayed instead of the dental arch image 211.

As illustrated in FIG. 1, in the X-ray CT photographic apparatus 1, the patient is fixed in the upright attitude, and the X-ray generation unit 10 and the X-ray detection unit 20 turn about the subject M1. Alternatively, a seat on which the subject M1 (patient) can sit may be provided to fix the subject M1 in a seating attitude. Alternatively, a stage on which the patient is supported in a supine attitude (or a prone attitude) may be provided to turn the X-ray generation unit 10 and the X-ray detection unit 20 about the patient.

In the X-ray CT photographic apparatus 1 of the above preferred embodiments, as illustrated in FIGS. 9, 18, and 20, the normal scan CT photography in which the whole CT photographic region CA is irradiated with the X-ray cone beam BX is performed during the X-ray CT photography. Alternatively, in the X-ray CT photographic apparatus 1, offset scan CT photography in which only part of the CT photographic region CA is irradiated with the X-ray cone beam BX may be performed during the X-ray CT photography. In the offset scan CT photography, the irradiation range of the X-ray cone beam BX is restricted with respect to the x-axis direction. For example, FIGS. 3A to 4D of Japanese Patent No. 4516626, FIGS. 16 to 20 of Japanese Patent Application Laid-Open No. 2008-114056, and FIGS. 2A to 12 of PCT Application International Publication No. WO 2009/063974 disclose specific offset scan CT photography methods.

As used herein, the CT photography in which the whole CT photographic region CA is irradiated with the X-ray cone beam BX during the CT photography is referred to as the normal scan CT photography. As illustrated in FIG. 20, a typical example of the normal scan CT photography is the CT photography in which the CT photographic region has the perfect-circle shape when viewed from the axis direction of the turning shaft.

In the offset scan CT photography, in the case that the X-ray CT photography of the same CT photographic region CA is performed, the X-ray cone beam BX is narrowed in the x-axis direction compared with the normal scan CT photography. Advantageously, an apparatus cost can be reduced because the X-ray detector 21 can be downsized. In the offset scan CT photography, in the case that X-ray CT photography is performed with the X-ray detector 21 having the same size, the wider CT photographic region CA can be set compared with the normal scan CT photography.

Each configuration of the preferred embodiments and modifications can be properly combined as long as the configurations are consistent with each other.

While the invention has been shown and described in detail, the foregoing description is in all aspects illustrative and not restrictive. It should be, therefore, understood that numerous modifications and variations can be devised without departing from the scope of the invention.

What is claimed is:

1. An X-ray CT photographic apparatus comprising:
   an X-ray generator;
   an X-ray detector arranged opposite the X-ray generator;
   a support body that supports the X-ray generator and the X-ray detector;
   a turning shaft;
   a support body turning drive unit that turns the support body about the turning shaft such that the X-ray generator and said X-ray detector turn about a subject during X-ray photography;
   the X-ray generator generating an X-ray for the subject positioned between the X-ray generator and the X-ray detector wherein the X-ray has an irradiation range;
   the X-ray detector having a detection surface receiving the X-ray;
   the X-ray detector reading an X-ray detection signal of the X-ray received by the detection surface;
   an X-ray regulating unit that regulates the irradiation range of said X-ray with shaping said X-ray into an X-ray cone beam;
   the X-ray detector detecting the X-ray cone beam after the X-ray cone beam is transmitted through the subject;
   an X-ray regulating controller that controls said irradiation range of said X-ray by controlling said X-ray regulating unit;
   a CT photographic region setting unit that receives a setting manipulation and sets a CT photographic region,
   wherein, a z-axis direction is an axis direction of said turning shaft, an x-axis direction and a y-axis direction are two directions orthogonal to each other in a two-dimensional plane orthogonal to said z-axis direction, and that the y-axis direction is a direction in which said X-ray generator and said X-ray detector are opposed, and
   in accordance with the setting manipulation, the X-ray regulating controller changes the irradiation range of said X-ray cone beam in said x-axis direction during X-ray CT photography wherein only a set CT photographic region is irradiated, and
   a read region controller changes a read region with respect to said x-axis direction in said detection surface according to said irradiation range of said X-ray cone beam.

2. The X-ray CT photographic apparatus according to claim 1, wherein said X-ray regulating controller changes the irradiation range of said X-ray cone beam to said z-axis direction according to said CT photographic region input through said CT photographic region setting unit before said X-ray photography, and said read region controller changes said read region with respect to said z-axis direction in said detection surface.

3. The X-ray CT photographic apparatus according to claim 1,
further comprising a display unit, and
wherein said CT photographic region setting unit displays an image relating to said subject on said display unit as a region assigning image, and receives a setting input of said CT photographic region on said region assigning image.

4. The X-ray CT photographic apparatus according to claim 3, wherein said CT photographic region setting unit displays said region assigning image and a setting region image indicating said CT photographic region while said region assigning image and the setting region image overlap with each other.

5. The X-ray CT photographic apparatus according to claim 3, wherein said CT photographic region setting unit displays said region assigning image to include a dental arch image that expresses a dental arch region.

6. The X-ray CT photographic apparatus according to claim 5, wherein
said dental arch image includes a curved line that expresses said dental arch region being curved, and
said CT photographic region setting unit receives an assignment manipulation to assign one end and the other end of said CT photographic region on said curved line.

7. The X-ray CT photographic apparatus according to claim 5, wherein said CT photographic region setting unit causes a user to select one of an upper jaw and a lower jaw of said subject as a target of said CT photographic region.

8. The X-ray CT photographic apparatus according to claim 5, wherein, when viewed from the axis direction of said turning shaft, said CT photographic region is set so as to become a substantially oval shape in which a longer direction extends along said dental arch region.

9. The X-ray CT photographic apparatus according to claim 5, wherein, when viewed from the axis direction of said turning shaft, said CT photographic region is set so as to become a substantially semicircular shape or a substantially triangular shape, which connects an outer periphery of the dental arch region while a vertex portion is located near an anterior tooth.

10. The X-ray CT photographic apparatus according to claim 1, wherein said X-ray regulating unit includes an X-ray shield member that regulates a shielding amount of the X-ray, which is generated from said X-ray generator, according to said CT photographic region.

11. The X-ray CT photographic apparatus according to claim 1, further comprising a first support body retention unit that retains said support body while the z-axis direction is fixed to a vertical direction.

12. The X-ray CT photographic apparatus according to claim 1, further comprising a second support body retention unit that retains said support body while the z-axis direction is fixed to a horizontal direction.

13. The X-ray CT photographic apparatus according to claim 1, wherein, when viewed from the axis direction of said turning shaft, said CT photographic region is set so as to become a circular shape.

14. The X-ray CT photographic apparatus according to claim 1, further comprising a photography mode switching unit that switches between a whole region CT photography mode in which the X-ray CT photography is performed in a whole region of said detection surface and a partial region CT photography mode in which the X-ray CT photography is performed in a partial region of the whole region of said detection surface, wherein,
during the X-ray CT photography in said whole region CT photography mode,
said X-ray regulating controller sets the irradiation range of said X-ray cone beam to the whole region of said detection surface, and
said read region controller sets the whole region of said detection surface to the read region, and
during the X-ray CT photography in said partial region CT photography mode,
said X-ray regulating controller changes the irradiation range of said X-ray cone beam to said x-axis direction such that only said CT photographic region is irradiated with said X-ray cone beam, and
said read region controller changes said read region in said detection surface to said x-axis direction.

15. The X-ray CT photographic apparatus according to claim 1, wherein
said subject includes a dental arch,
said X-ray regulating unit forms said X-ray in an X-ray slit beam that extends in the axis direction of said turning shaft,
while said support body turning drive unit turns said support body, said X-ray regulating controller changes the irradiation range of said X-ray slit beam to said x-axis direction to perform panoramic photography such that said X-ray slit beam forms an envelope to irradiate the irradiation range of said X-ray slit beam therewith, and
said read region controller changes said read region to said x-axis direction in said detection surface while correlating said read region with the irradiation range of said X-ray slit beam.

16. The X-ray CT photographic apparatus according to claim 1, wherein said read region controller changes a frame rate, at which data is read from said read region, according to a turning angle about said turning shaft of said support body.

17. The X-ray CT photographic apparatus according to claim 1, wherein said read region controller includes a frame rate setting unit that changes a frame rate, at which data is read from said read region, according to a size of the CT photographic region, a kind of a photographic target area, a photographing purpose, or a position of the photographic target area.

18. The X-ray CT photographic apparatus according to claim 1, wherein the read region controller changes said read region by selectively activating detection segments.

19. The X-ray CT photographic apparatus according to claim 1, wherein a turning center of the turning shaft is fixed in the two-dimensional plane.

* * * * *